(12) United States Patent
Durocher et al.

(10) Patent No.: US 11,897,925 B2
(45) Date of Patent: Feb. 13, 2024

(54) TREATMENT OF HOMOLOGOUS RECOMBINATION DEFICIENT CANCERS

(71) Applicant: Sinai Health System, Toronto (CA)

(72) Inventors: Daniel Durocher, Toronto (CA); Salomé Adam, Toronto (CA); Silvia Emma Rossi, Toronto (CA); Yibo Xue, Toronto (CA)

(73) Assignee: Sinai Health System, Toronto (CA)

( * ) Notice: Subject to any disclaimer, the term of this patent is extended or adjusted under 35 U.S.C. 154(b) by 0 days.

(21) Appl. No.: 17/520,638

(22) Filed: Nov. 6, 2021

(65) Prior Publication Data
US 2022/0153793 A1    May 19, 2022

Related U.S. Application Data

(60) Provisional application No. 63/114,838, filed on Nov. 17, 2020.

(51) Int. Cl.
| | | |
|---|---|---|
| C07K 14/47 | (2006.01) | |
| A61P 35/00 | (2006.01) | |
| A61K 38/00 | (2006.01) | |

(52) U.S. Cl.
CPC .......... *C07K 14/4703* (2013.01); *A61P 35/00* (2018.01); *A61K 38/00* (2013.01)

(58) Field of Classification Search
CPC ...... C07K 14/4703; A61P 35/00; A61K 38/00
See application file for complete search history.

(56) References Cited

U.S. PATENT DOCUMENTS

| | | | | |
|---|---|---|---|---|
| 7,745,391 B2 * | 6/2010 | Mintz | ...................... | A61P 37/00 514/19.3 |
| 8,080,531 B2 * | 12/2011 | Kumagai | ........... | G01N 33/5011 536/23.1 |
| 2007/0083334 A1 * | 4/2007 | Mintz | ...................... | G16B 40/00 702/19 |

OTHER PUBLICATIONS

Forma et al., 2012, Molecular basis of gynecological oncology—TopBP1 protein and its participation in the transcription process, Ginekol Pol, 83: 363-367.*
Forma et al., 2013, Molecular basis of gynecological oncology—TopBP1 protein as the guardian of genome integrity, Ginekoi Pol, 84: 373-376.*
Wardlaw et al., 2014, TopBP1: A BRCT-scaffold protein functioning in multiple cellular pathways, DNA Repair, 22: 165-174.*
De et al., 2014, Oncogenic nexus of cancerous inhibitor of protein phosphatase 2A (CIP2A): an oncoprotein with many hands, Oncotarget, 5(13): 4581-4602.*
Soofiyani et al., 2017, The role of CIP2A in cancer: A review and update, Biomedicine & Pharmacotherapy, 96: 626-633.*
Alvarez-Quilon et al., Endogenous DNA 3' Blocks Are Vulnerabilities for BRCA1 and BRCA2 Deficiency and Are Reversed by the APE2 Nuclease. Mol Cell. Jun. 1, 20208;78(6):1152-1165.e8. Epub Jun. 8, 2020.
Bagge et al., Functions of TopBP1 in preserving genome integrity during mitosis. Semin Cell Dev Biol. May 2021; 113:57-64. Epub Sep. 8, 2020.
Banasik et al., Inhibitors and activators of ADP-ribosylation reactions. Mol Cell Biochem. Sep. 1994; 138(1-2):185-97.
Banasik et al., Specific inhibitors of poly(ADP-ribose) synthetase and mono(ADP-ribosyl)transferase. J Biol Chem. Jan. 25, 1992;267(3):1569-75.
Banaszynski et al., A rapid, reversible, and tunable method to regulate protein function in living cells using synthetic small molecules. Cell. Sep. 8, 2006;126(5):995-1004.
Bang et al., Human TopBP1 localization to the mitotic centrosome mediates mitotic progression. Exp Cell Res. Apr. 15, 2011;317(7):994-1004.
Becker et al., BARD1 reads H2A lysine 15 ubiquitination to direct homologous recombination. Nature. Aug. 2021;596(7872):433-437. Epub Jul. 28, 2021.
Behan et al., Prioritization of cancer therapeutic targets using CRISPR-Cas9 screens. Nature. Apr. 2019;568(7753):511-516.
Bhowmick et al., RAD52 Facilitates Mitotic DNA Synthesis Following Replication Stress. Mol Cell. Dec. 15, 2016;64(6):1117-1126.
Blackford et al., How Cells Respond to DNA Breaks in Mitosis. Trends Biochem Sci. Apr. 2020;45(4):321-331. Epub Jan. 27, 2020.
Blessing et al., The Oncogenic Helicase ALC1 Regulates PARP Inhibitor Potency by Trapping PARP2 at DNA Breaks. Mol Cell. Dec. 3, 2020;80(5):862- 875.e6.
Bouwman et al., 53BP1 loss rescues BRCA1 deficiency and is associated with triple-negative and BRCA-mutated breast cancers. Nat Struct Mol Biol. Jun. 2010;17(6):688-95.
Broderick et al., TOPBP1 recruits TOP2A to ultra-fine anaphase bridges to aid in their resolution. Nat Commun. Mar. 12, 2015;6:6572.
Bryant et al., Specific killing of BRCA2-deficient tumours with inhibitors of poly(ADP-ribose) polymerase. Nature. Apr. 14, 2005;434(7035):913-7.
Bunting et al., 53BP1 inhibits homologous recombination in Brca1-deficient cells by blocking resection of DNA breaks. Cell. Apr. 16, 2010;141(2):243-54.
Ceccaldi et al., Homologous-recombination-deficient tumours are dependent on Polθ-mediated repair. Nature. Feb. 12, 2015;518(7538):258-62.
Demarco et al., The CIP2A-TOPBP1 complex safeguards chromosomal stability during mitosis. bioRxiv 2021.02.08.430274; Posted Feb. 8, 2021.
Dempster et al., Extracting Biological Insights from the Project Achilles Genome-Scale CRISPR Screens in Cancer Cell Lines. bioRxiv 720243; doi: https://doi.org/10.1101/720243. Posted Jul. 31, 2019.
Elstrodt et al., BRCA1 mutation analysis of 41 human breast cancer cell lines reveals three new deleterious mutants. Cancer Res. Jan. 1, 2006;66(1):41-5.
England et al., HaloTag technology: a versatile platform for biomedical applications. Bioconjug Chem. Jun. 17, 2015;26(6):975-86.

(Continued)

*Primary Examiner* — Amber D Steele
(74) *Attorney, Agent, or Firm* — Howson & Howson LLP; Colleen M. Schaller

(57) ABSTRACT

Disclosed are compounds, compositions, uses and methods using inhibitors of the CIP2A-TOPBP1 complex or agents that inhibit phosphopeptide recognition of TOPBP1 BRCT7/8, for treatment of a cancer associated with or characterized by a homologous recombination (HR) deficiency or treatment of cancer cells having HR deficiency.

5 Claims, 12 Drawing Sheets

Specification includes a Sequence Listing.

(56) References Cited

OTHER PUBLICATIONS

Farmer et al., Targeting the DNA repair defect in BRCA mutant cells as a therapeutic strategy. Nature. Apr. 14, 2005;434(7035):917-21.
Fellman et al., Cornerstones of CRISPR-Cas in drug discovery and therapy. Nat Rev Drug Discov. Feb. 2017; 16(2):89-100.
Feng et al., BRCA2 suppresses replication stress-induced mitotic and G1 abnormalities through homologous recombination. Nat Commun. Sep. 13, 2017;8(1):525.
Garcia et al., Identification and functional analysis of TopBP1 and its homologs. DNA Repair (Amst). Nov. 21, 2005;4(11):1227-39.
Giepmans et al., The fluorescent toolbox for assessing protein location and function. Science. Apr. 14, 2006;312(5771):217-24.
Gong et al., BACH1/FANCJ acts with TopBP1 and participates early in DNA replication checkpoint control. Mol Cell. Feb. 12, 2010;37(3):438-46.
Gowen et al., Brca1 deficiency results in early embryonic lethality characterized by neuroepithelial abnormalities. Nat Genet. Feb. 1996; 12(2):191-4.
Hakem et al., Partial rescue of Brca1 (5-6) early embryonic lethality by p53 or p21 null mutation. Nat Genet. Jul. 1997;16(3):298-302.
Hakem et al., The tumor suppressor gene Brca1 is required for embryonic cellular proliferation in the mouse. Cell. Jun. 28, 1996;85(7):1009-23.
Hart et al., BAGEL: a computational framework for identifying essential genes from pooled library screens. BMC Bioinformatics. Apr. 16, 2016;17:164.
Hart et al., Evaluation and Design of Genome-Wide CRISPR/SpCas9 Knockout Screens. G3 (Bethesda). Aug. 7, 2017;7(8):2719-2727.
Hart et al., High-Resolution CRISPR Screens Reveal Fitness Genes and Genotype-Specific Cancer Liabilities., Cell. Dec. 3, 2015;163(6):1515-26.
Hustedt et al., A consensus set of genetic vulnerabilities to ATR inhibition. Open Biol. Sep. 27, 2019;9(9):190156. Epub Sep. 11, 2019.
Ito et al. PARP Inhibitors in Clinical Use Induce Genomic Instability in Normal Human Cells. PLoS One. Jul. 18, 2016;11(7):e0159341.
Janysek et al., Clinical use and mechanisms of resistance for PARP inhibitors in homologous recombination-deficient cancers. Transl Oncol. Mar. 2021;14(3):101012. Epub Jan. 27, 2021.
Jeong et al., Cancerous inhibitor of protein phosphatase 2A (CIP2A) protein is involved in centrosome separation through the regulation of NIMA (never in mitosis gene A)-related kinase 2 (NEK2) protein activity. J Biol Chem. Jan. 3, 2014;289(1):28-40.
Junttila et al., CIP2A inhibits PP2A in human malignancies. Cell. Jul. 13, 2007;130(1):51-62.
Khanna et al., Cancerous inhibitor of protein phosphatase 2A, an emerging human oncoprotein and a potential cancer therapy target. Cancer Res. Nov. 15, 2013;73(22):6548-53.
Kim et al., CIP2A modulates cell-cycle progression in human cancer cells by regulating the stability and activity of Plk1. Cancer Res. Nov. 15, 2013;73(22):6667-78.
Kim et al., Improved analysis of CRISPR fitness screens and reduced off-target effects with the BAGEL2 gene essentiality classifier. Genome Med. Jan. 6, 2021;13(1):2.
Konstantinopoulous et al., Homologous Recombination Deficiency: Exploiting the Fundamental Vulnerability of Ovarian Cancer, Cancer Discov. Nov. 2015;5(11):1137-54.
Laine et al., CIP2A Interacts with TopBP1 and Drives Basal-Like Breast Cancer Tumorigenesis. Cancer Res. Aug. 15, 2021;81(16):4319-4331. Epub Jun. 18, 2021.
Leimbacher et al., MDC1 Interacts with TOPBP1 to Maintain Chromosomal Stability during Mitosis. Mol Cell. May 2, 2019;74(3):571-583.e8. Epub Mar. 18, 2019.
Leung et al., Molecular basis of BACH1/FANCJ recognition by TopBP1 in DNA replication checkpoint control. J Biol Chem. Feb. 11, 2011;286(6):4292-301.
Lezaja et al., Dealing with DNA lesions: When one cell cycle is not enough. Curr Opin Cell Biol. Jun. 2021;70:27-36. Epub Dec. 10, 2020.
Li et al., Proteolysis-targeting chimera (PROTAC) for targeted protein degradation and cancer therapy. J Hematol Oncol. May 13, 2020;13(1):50.
Lin et al., Protein-Protein Interactions: Yeast Two-Hybrid System. Methods Mol Biol. 2017;1615:177-187. [First Online: Jul. 1, 2017].
Liu et al., Cancerous inhibitor of PP2A is targeted by natural compound celastrol for degradation in non-small-cell lung cancer. Carcinogenesis. Apr. 2014;35(4):905-14.
Lord et al., BRCAness revisited. Nat Rev Cancer. Feb. 2016;16(2):110-20.
Lord et al., PARP inhibitors: Synthetic lethality in the clinic. Science. Mar. 17, 2017;355(6330):1152-1158.
Ludwig et al., Targeted mutations of breast cancer susceptibility gene homologs in mice: lethal phenotypes of Brca1, Brca2, Brca1/Brca2, Brca1/p53, and Brca2/p53 nullizygous embryos. Genes Dev. May 15, 1997;11(10):1226-41.
Lundin et al., Oligonucleotide Therapies: The Past and the Present. Hum Gene Ther. Aug. 2015;26(8):475-85.
Manke et al., BRCT Repeats As Phosphopeptide-Binding Modules Involved in Protein Targeting. Science. Oct. 24, 2003;302(5645):636-9.
Mateos-Gomez et al., Mammalian polymerase θ promotes alternative NHEJ and suppresses recombination. Nature. Feb. 12, 2015;518(7538):254-7.
Mengwasser et al., Genetic Screens Reveal FEN1 and APEX2 as BRCA2 Synthetic Lethal Targets. Mol Cell. Mar. 7, 2019;73(5):885-899.e6. Epub Jan. 24, 2019.
Moynahan et al., Mitotic homologous recombination maintains genomic stability and suppresses tumorigenesis. Nat Rev Mol Cell Biol. Mar. 2010;11(3):196-207.
Nik-Zainal et al., Landscape of somatic mutations in 560 breast cancer whole-genome sequences. Nature. Jun. 2, 2016;534(7605):47-54.
Noordermeer et al., The shieldin complex mediates 53BP1-dependent DNA repair. Nature. Aug. 2018;560(7716):117-121.
Ohsumi et al., MolBioLib: a C++11 framework for rapid development and deployment of bioinformatics tasks. Bioinformatics. Oct. 1, 2012;28(19):2412-6.
Olivieri et al., A Genetic Map of the Response to DNA Damage in Human Cells. Cell. Jul. 23, 2020;182(2):481-496.e21. Epub Jul. 9, 2020.
Olivieri et al., Genome-scale chemogenomic CRISPR screens in human cells using the TKOv3 library. STAR Protoc. Feb. 5, 2021;2(1):100321. eCollection Mar. 19, 2021.
Ozer et al., Pathways for maintenance of telomeres and common fragile sites during DNA replication stress. Open Biol. Apr. 2018;8(4):180018.
Qiu et al., ATR/CHK1 inhibitors and cancer therapy. Radiother Oncol. Mar. 2018;126(3):450-464.
Rizk et al., Segmentation and quantification of subcellular structures in fluorescence microscopy images using Squassh, Nat Protoc. Mar. 2014;9(3):586-96.
Rodriguez-Negrete et al., Using the yeast two-hybrid system to identify protein-protein interactions. Methods Mol Biol. 2014;1072:241-58. [First Online: Aug. 22, 2013].
Roy et al., BRCA1 and BRCA2: different roles in a common pathway of genome protection. Nat Rev Cancer. Dec. 23, 2011;12(1):68-78.
Setton et al., Synthetic Lethality in Cancer Therapeutics: The Next Generation. Cancer Discov. Jul. 2021;11(7):1626-1635. Epub Apr. 1, 2021.
Shanbhag et al., ATM-dependent chromatin changes silence transcription in cis to DNA double-strand breaks. Cell. Jun. 11, 2010;141(6):970-81.
Tang et al., Acetylation limits 53BP1 association with damaged chromatin to promote homologous recombination. Nat Struct Mol Biol. Mar. 2013;20(3):317-25.
Terpe, Overview of tag protein fusions: from molecular and biochemical fundamentals to commercial systems. Appl Microbiol Biotechnol. Jan. 2003;60(5):523-33.

(56) References Cited

OTHER PUBLICATIONS

Timms et al., Association of BRCA1/2defects with genomic scores predictive of DNA damage repair deficiency among breast cancer subtypes. Breast Cancer Res. Dec. 5, 2014;16(6):475.
Turner et al., Hallmarks of 'BRCAness' in sporadic cancers. Nat Rev Cancer. Oct. 2004;4(10):814-9.
Van Der Weegen et al., ELOF1 is a transcription-coupled DNA repair factor that directs RNA polymerase II ubiquitylation. Nat Cell Biol. Jun. 2021;23(6):595-607. Epub Jun. 9, 2021.
Ventela et al., CIP2A promotes proliferation of spermatogonial progenitor cells and spermatogenesis in mice. PLoS One. Mar. 26, 2012;7(3):e33209.
Verma et al., ALC1 links chromatin accessibility to PARP inhibitor response in homologous recombination-deficient cells. Nat Cell Biol. Feb. 2021;23(2):160-171. Epub Jan. 18, 2021.
Wang et al., Oncoprotein CIP2A is stabilized via interaction with tumor suppressor PP2A/B56. EMBO Rep. Mar. 2017;18(3):437-450.
Waugh, Making the most of affinity tags. Trends Biotechnol. Jun. 2005;23(6):316-20.
Wilson et al., Molecular mechanisms of sister-chromatid exchange. Mutat Res. Mar. 1, 2007;616(1-2):11-23.
Wittrup et al., Knocking down disease: a progress report on siRNA therapeutics. Nat Rev Genet. Sep. 2015;16(9):543-52.
Yamane et al., A DNA-topoisomerase-II-binding protein with eight repeating regions similar to DNA-repair enzymes and to a cell-cycle regulator. Eur J Biochem. Dec. 15, 1997;250(3):794-9.
Yu et al., Erlotinib derivative inhibits hepatocellular carcinoma by targeting CIP2A to reactivate protein phosphatase 2A. Cell Death Dis. Jul. 31, 2014;5(7):e1359.
Yu et al., The BRCT domain is a phospho-protein binding domain. Science. Oct. 24, 2003;302(5645):639-42.
Zhou et al., PROTAC: A promising technology for cancer treatment. Eur J Med Chem. Oct. 1, 2020;203:112539. Epub Jul. 15, 2020.
Zimmerman et al., CRISPR screens identify genomic ribonucleotides as a source of PARP-trapping lesions. Nature. Jul. 2018;559(7713):285-289.

\* cited by examiner

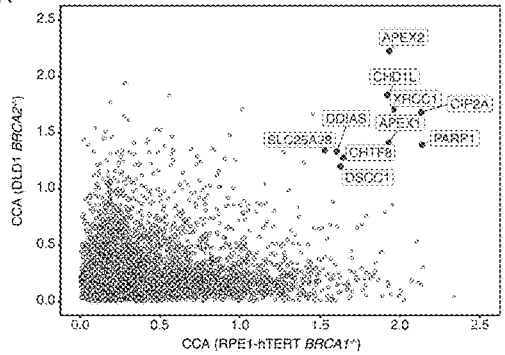
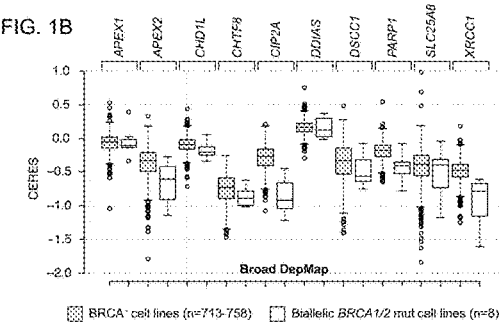
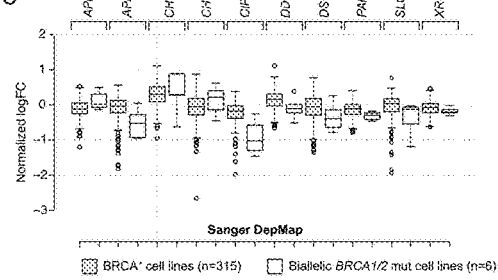
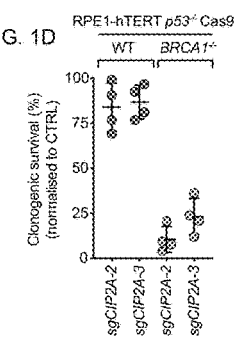
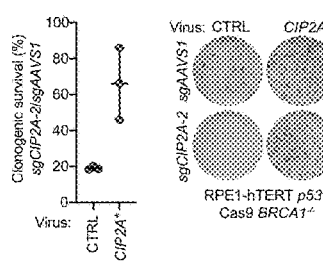
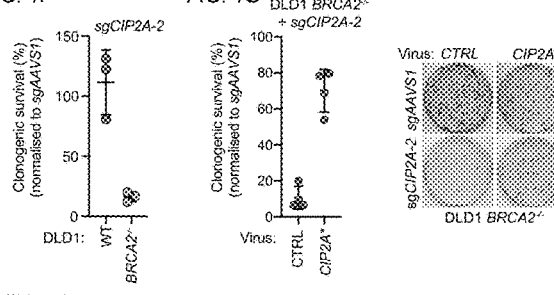
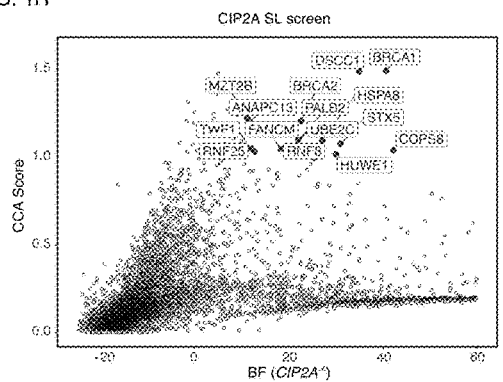

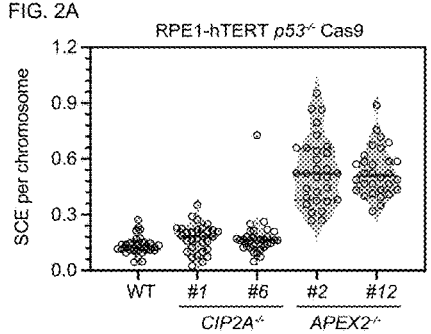
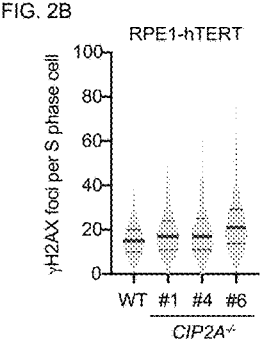
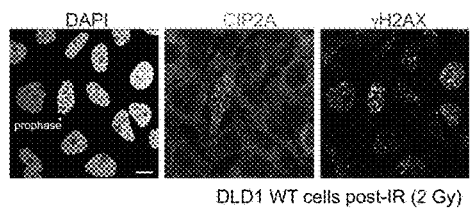
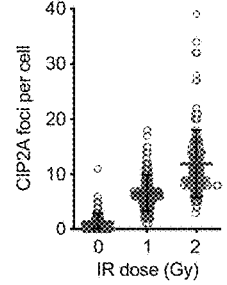
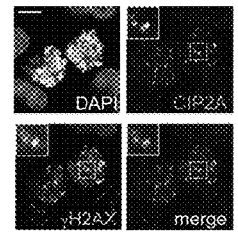
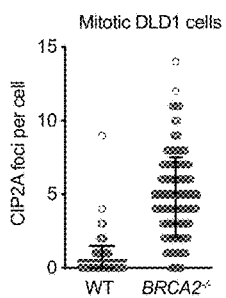
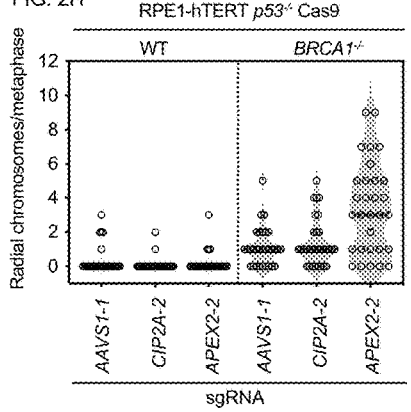
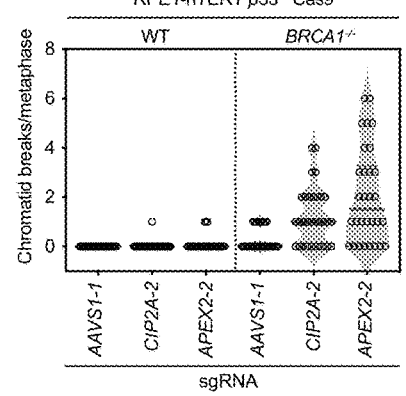
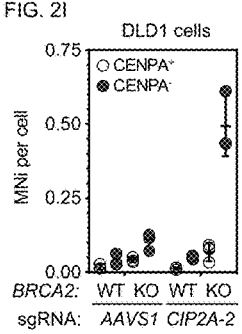
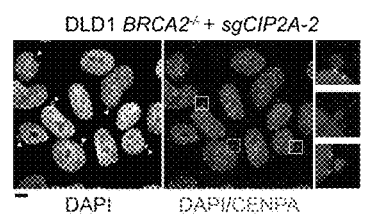

FIG. 3A
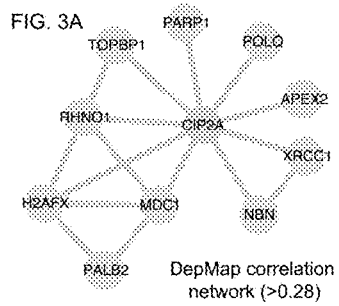
DepMap correlation network (>0.28)
FIG. 3B
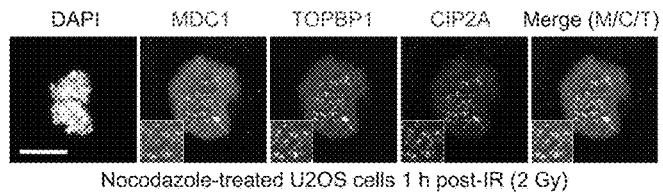
Nocodazole-treated U2OS cells 1 h post-IR (2 Gy)
FIG. 3C
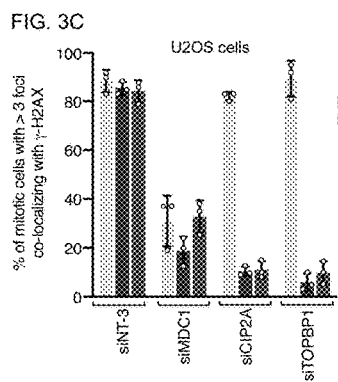
FIG. 3D  Frequently observed structures containing CIP2A and TOPBP1
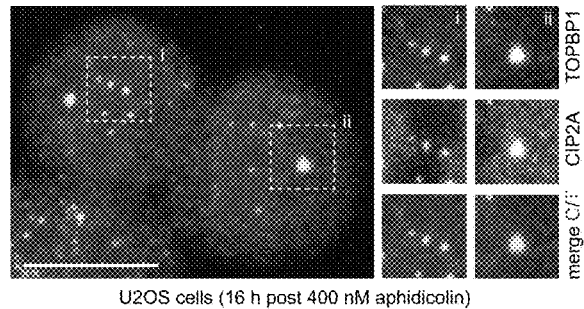
U2OS cells (16 h post 400 nM aphidicolin)
FIG. 3E  Example of filament-like localization
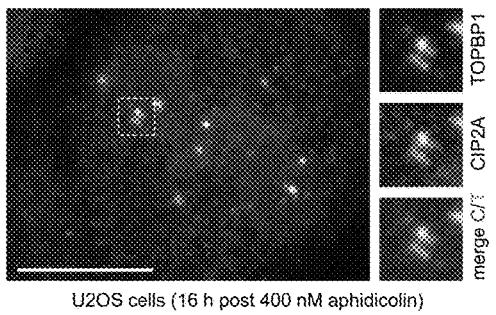
U2OS cells (16 h post 400 nM aphidicolin)
FIG. 3F
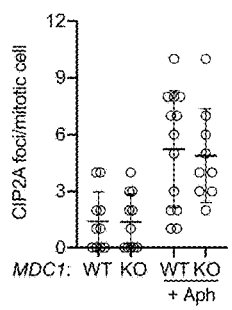
FIG. 3G
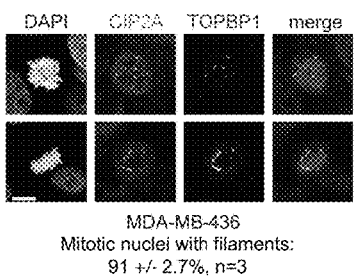
MDA-MB-436
Mitotic nuclei with filaments:
91 +/- 2.7%, n=3

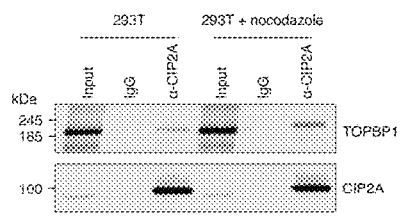
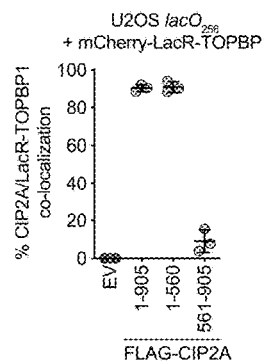
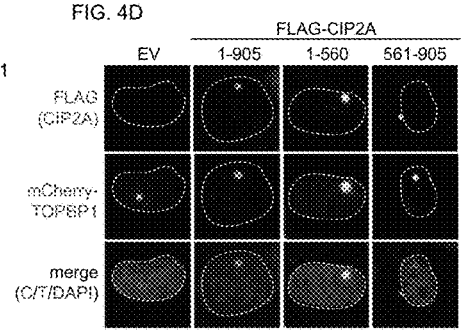
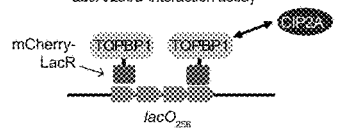
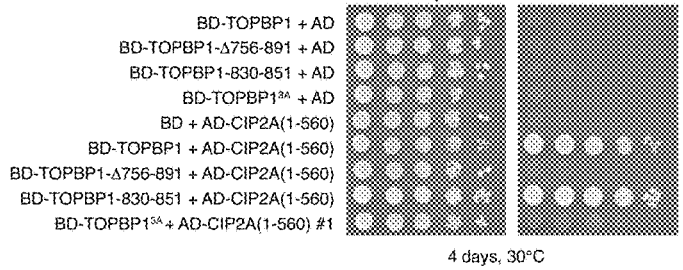
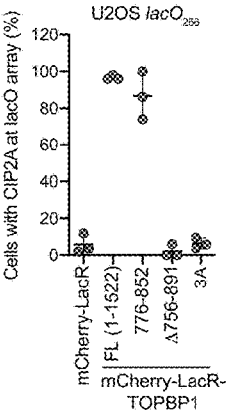
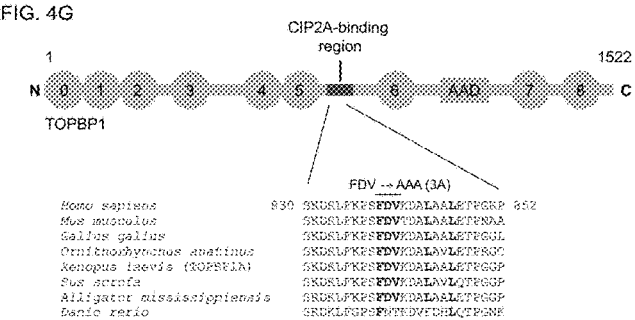
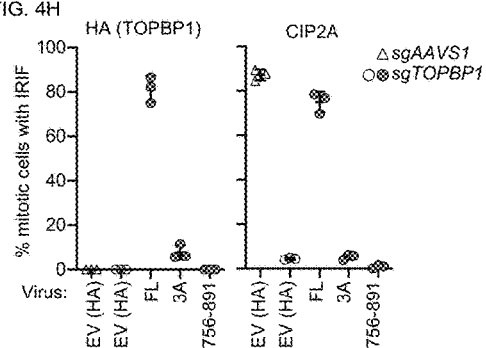
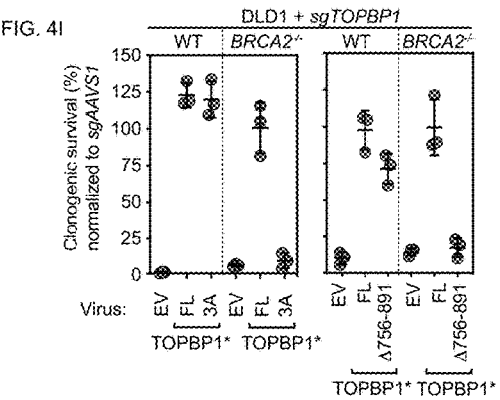
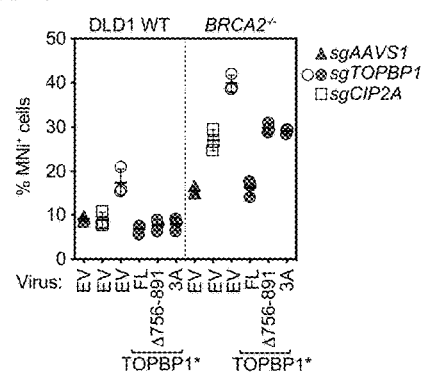

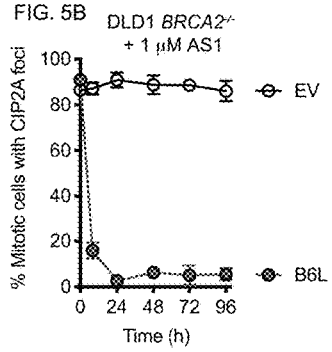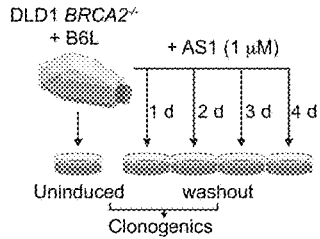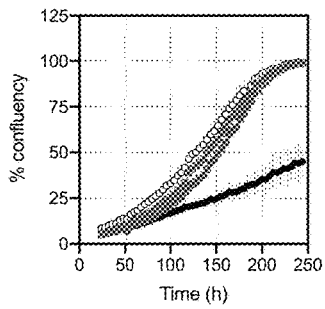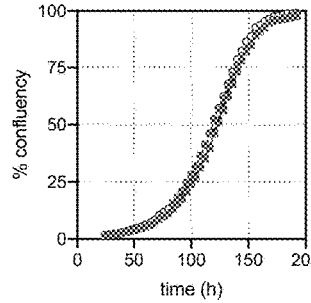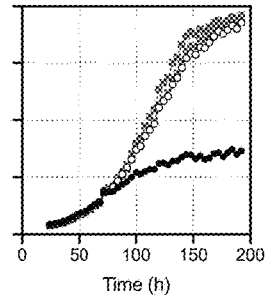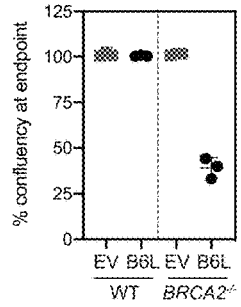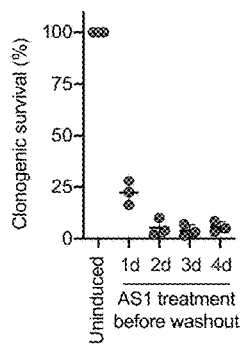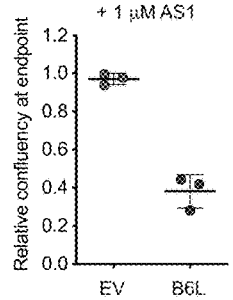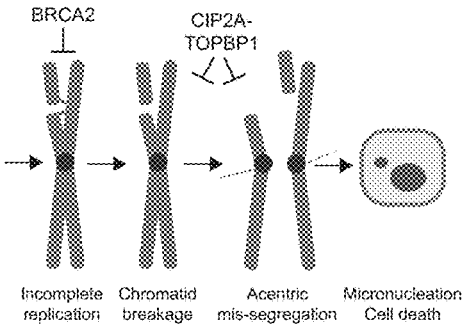

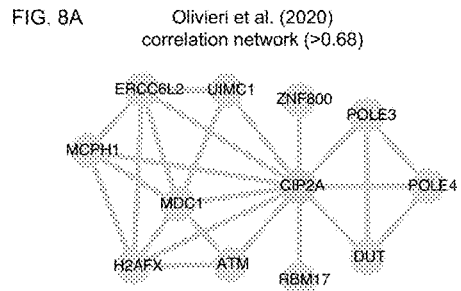
FIG. 8A Olivieri et al. (2020) correlation network (>0.68)
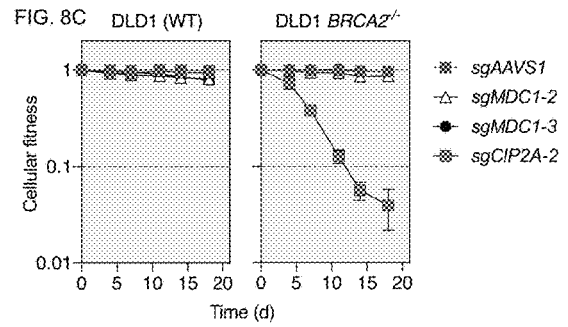
FIG. 8C
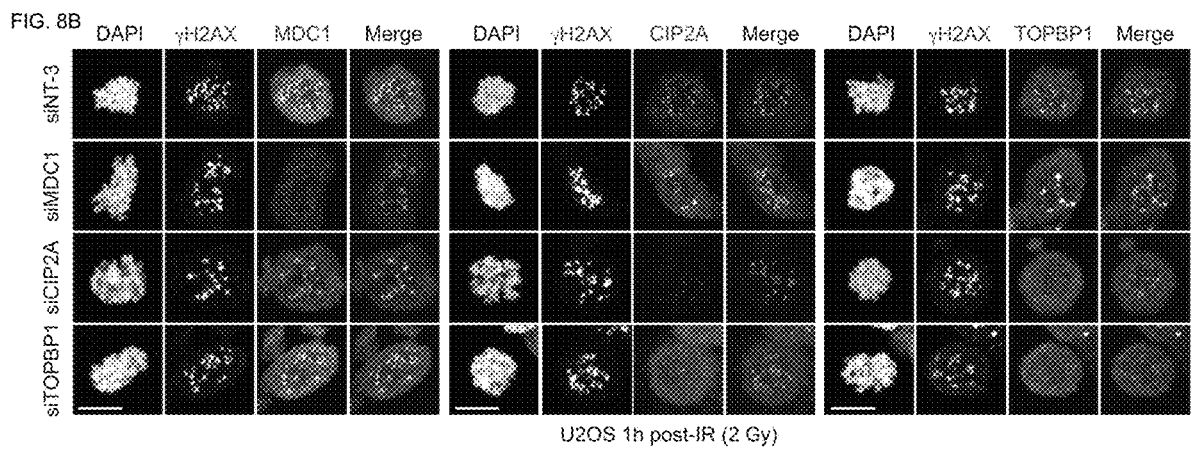
FIG. 8B
U2OS 1h post-IR (2 Gy)
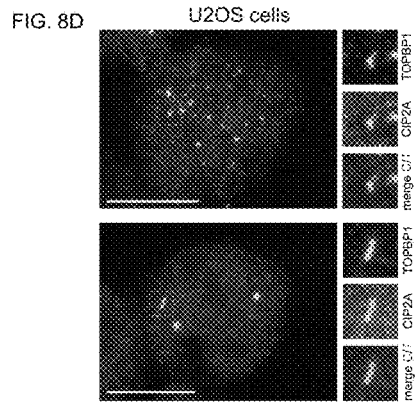
FIG. 8D U2OS cells
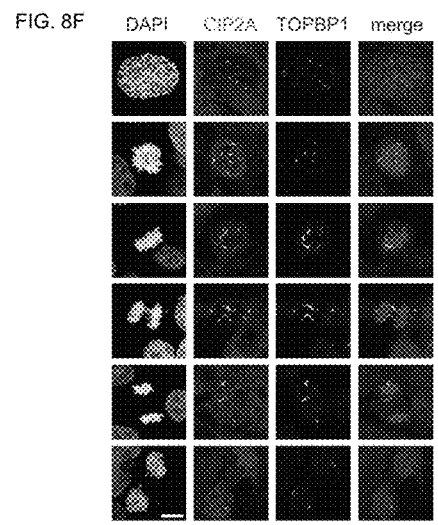
FIG. 8F
Untreated MDA-MB-436 cells
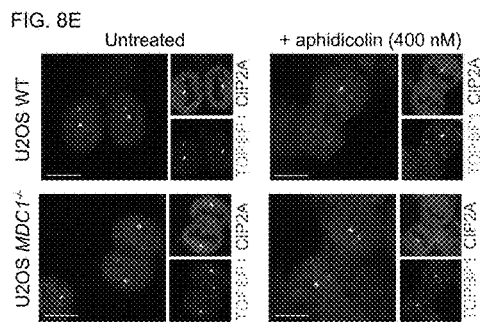
FIG. 8E

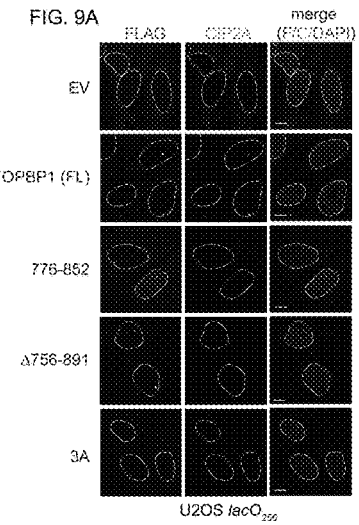
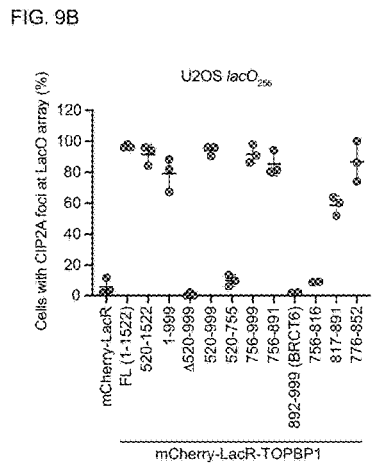
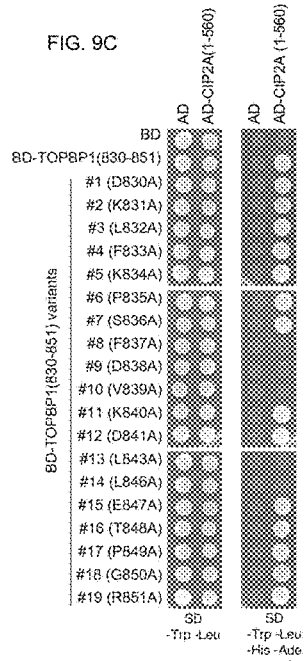
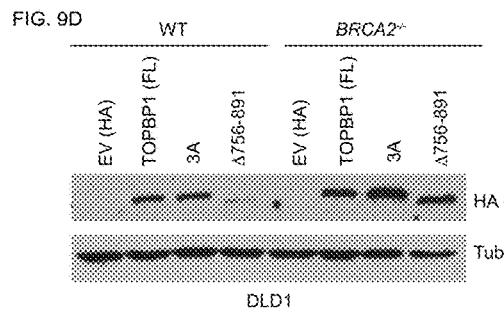
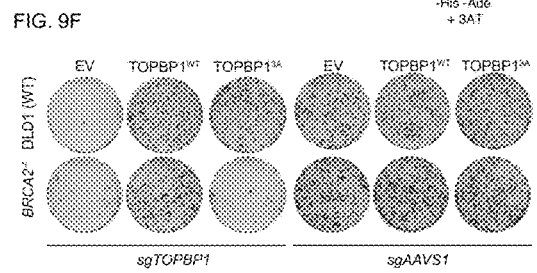
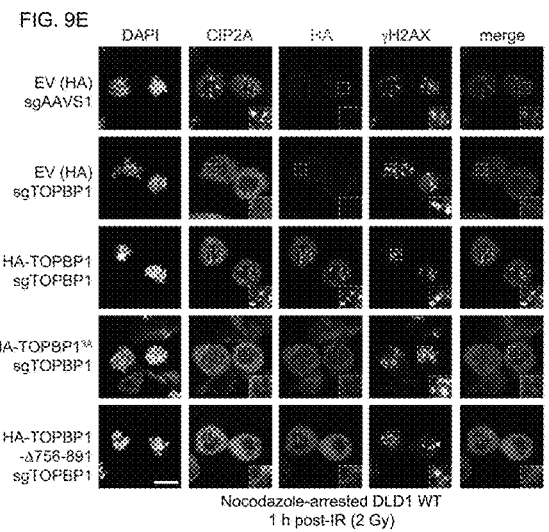
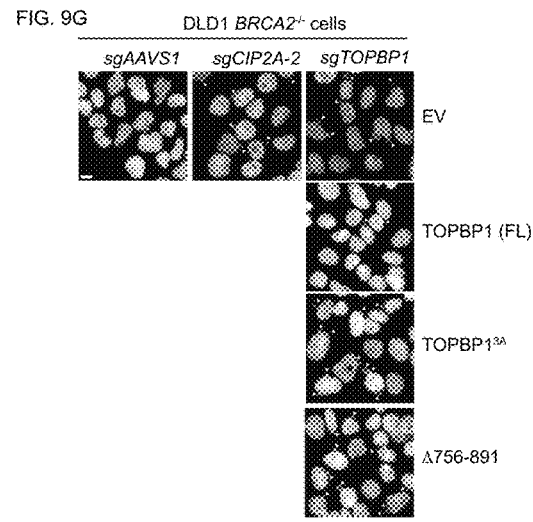

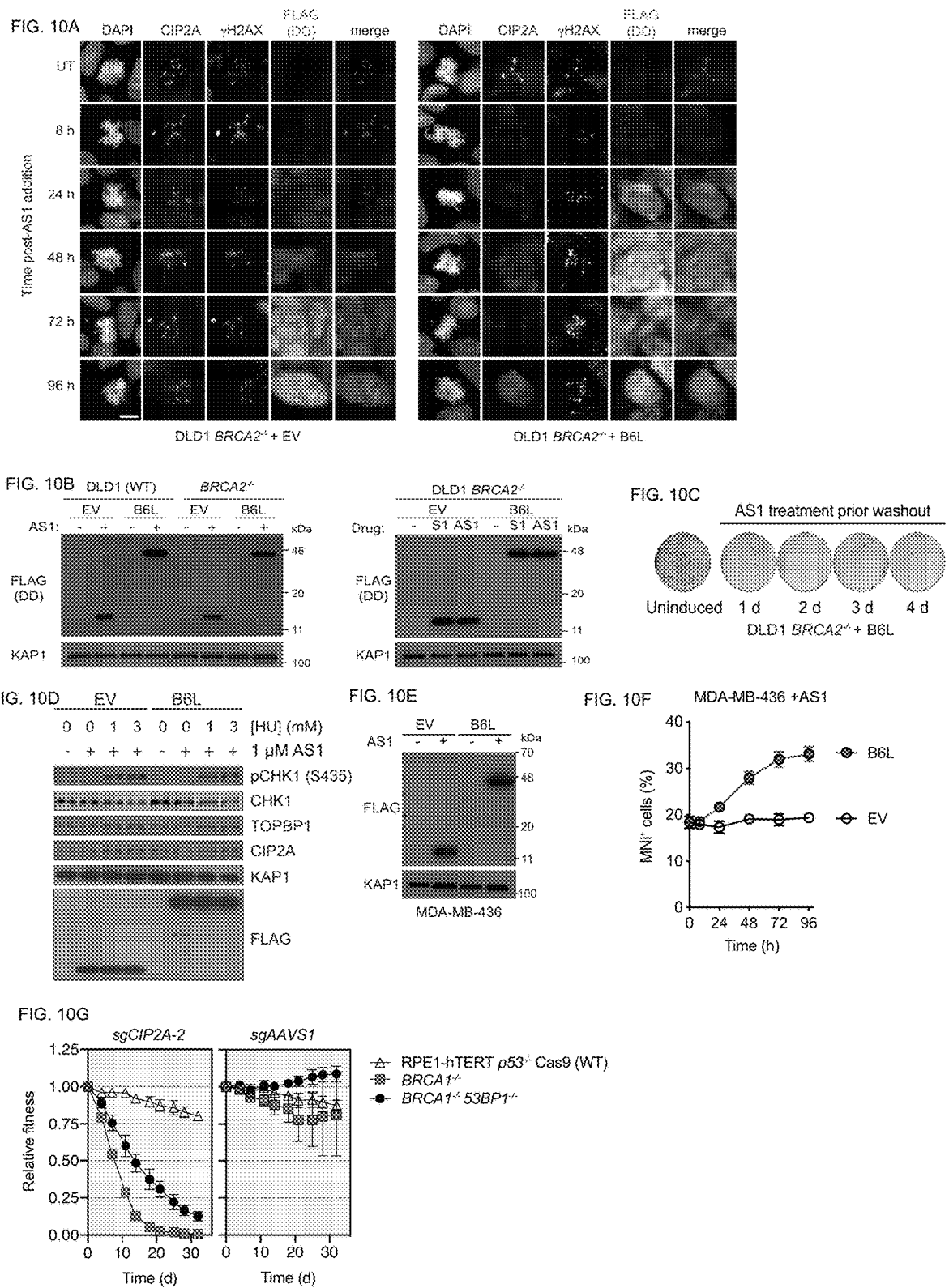

SEQUENCE LISTING

<160> NUMBER OF SEQ ID NOS: 13

<210> SEQ ID NO 1
<211> LENGTH: 25
<212> TYPE: PRT
<213> ORGANISM: Homo sapiens

<400> SEQUENCE: 1

Ser Lys Asp Lys Leu Phe Lys Pro Ser Phe Asp Val Lys Asp Ala Leu
1               5                   10                  15

Ala Ala Leu Glu Thr Pro Gly Arg Pro
            20                  25

<210> SEQ ID NO 2
<211> LENGTH: 25
<212> TYPE: PRT
<213> ORGANISM: Mus musculus

<400> SEQUENCE: 2

```
Ser Lys Asp Lys Leu Phe Lys Pro Ser Phe Asp Val Thr Asp Ala Leu
1               5                   10                  15

Ala Ala Leu Glu Thr Pro Asn Ala Ala
            20                  25
```

<210> SEQ ID NO 3
<211> LENGTH: 25
<212> TYPE: PRT
<213> ORGANISM: Gallus gallus

<400> SEQUENCE: 3

```
Ser Lys Asp Lys Leu Phe Lys Pro Ser Phe Asp Val Lys Asp Ala Leu
1               5                   10                  15

Ala Ala Leu Glu Thr Pro Gly Gly Leu
            20                  25
```

<210> SEQ ID NO 4
<211> LENGTH: 25
<212> TYPE: PRT
<213> ORGANISM: Ornithorhynchus anatinus

<400> SEQUENCE: 4

```
Ser Lys Asp Lys Leu Phe Lys Pro Ser Phe Asp Val Lys Asp Ala Leu
1               5                   10                  15

Ala Val Leu Glu Thr Pro Arg Gly Cys
            20                  25
```

<210> SEQ ID NO 5
<211> LENGTH: 26
<212> TYPE: PRT
<213> ORGANISM: Xenopus laevis

<400> SEQUENCE: 5

```
Ser Lys Asp Lys Leu Phe Lys Pro Ser Phe Asp Val Lys Asp Ala Leu
1               5                   10                  15

Ala Ala Leu Glu Thr Pro Gly Gly Pro Ser
            20                  25
```

<210> SEQ ID NO 6
<211> LENGTH: 25
<212> TYPE: PRT
<213> ORGANISM: Sus scrofa

<400> SEQUENCE: 6

```
Ser Lys Asp Lys Leu Phe Lys Pro Ser Phe Asp Val Lys Asp Ala Leu
1               5                   10                  15

Ala Val Leu Gln Thr Pro Gly Gly Pro
            20                  25
```

<210> SEQ ID NO 7
<211> LENGTH: 25
<212> TYPE: PRT
<213> ORGANISM: Alligator mississippiensis

<400> SEQUENCE: 7

```
Ser Arg Asp Lys Leu Phe Lys Pro Ser Phe Asp Val Lys Asp Ala Leu
1               5                   10                  15

Ala Ala Leu Glu Thr Pro Gly Gly Pro
            20                  25
```

<210> SEQ ID NO 8

<211> LENGTH: 25
<212> TYPE: PRT
<213> ORGANISM: Danio rerio

<400> SEQUENCE: 8

Ser Arg Asp Lys Leu Phe Gly Pro Ser Phe Asn Thr Lys Asp Val Phe
1               5                   10                  15

Asp His Leu Gln Thr Pro Gly Asn Lys
            20                  25

<210> SEQ ID NO 9
<211> LENGTH: 10
<212> TYPE: PRT
<213> ORGANISM: Homo sapiens

<400> SEQUENCE: 9

Phe Asp Val Lys Asp Ala Leu Ala Ala Leu
1               5                   10

<210> SEQ ID NO 10
<211> LENGTH: 905
<212> TYPE: PRT
<213> ORGANISM: Homo sapiens

<400> SEQUENCE: 10

Met Asp Ser Thr Ala Cys Leu Lys Ser Leu Leu Leu Thr Val Ser Gln
1               5                   10                  15

Tyr Lys Ala Val Lys Ser Glu Ala Asn Ala Thr Gln Leu Leu Arg His
            20                  25                  30

Leu Glu Val Ile Ser Gly Gln Lys Leu Thr Arg Leu Phe Thr Ser Asn
        35                  40                  45

Gln Ile Leu Thr Ser Glu Cys Leu Ser Cys Leu Val Glu Leu Leu Glu
    50                  55                  60

Asp Pro Asn Ile Ser Ala Ser Leu Ile Leu Ser Ile Ile Gly Leu Leu
65                  70                  75                  80

Ser Gln Leu Ala Val Asp Ile Glu Thr Arg Asp Cys Leu Gln Asn Thr
                85                  90                  95

Tyr Asn Leu Asn Ser Val Leu Ala Gly Val Val Cys Arg Ser Ser His
            100                 105                 110

Thr Asp Ser Val Phe Leu Gln Cys Ile Gln Leu Leu Gln Lys Leu Thr
        115                 120                 125

Tyr Asn Val Lys Ile Phe Tyr Ser Gly Ala Asn Ile Asp Glu Leu Ile
    130                 135                 140

Thr Phe Leu Ile Asp His Ile Gln Ser Ser Glu Asp Glu Leu Lys Met
145                 150                 155                 160

Pro Cys Leu Gly Leu Leu Ala Asn Leu Cys Arg His Asn Leu Ser Val
                165                 170                 175

Gln Thr His Ile Lys Thr Leu Ser Asn Val Lys Ser Phe Tyr Arg Thr
            180                 185                 190

Leu Ile Thr Leu Leu Ala His Ser Ser Leu Thr Val Val Phe Ala
        195                 200                 205

Leu Ser Ile Leu Ser Ser Leu Thr Leu Asn Glu Glu Val Gly Glu Lys
    210                 215                 220

Leu Phe His Ala Arg Asn Ile His Gln Thr Phe Gln Leu Ile Phe Asn
225                 230                 235                 240

Ile Leu Ile Asn Gly Asp Gly Thr Leu Thr Arg Lys Tyr Ser Val Asp
                245                 250                 255

```
Leu Leu Met Asp Leu Leu Lys Asn Pro Lys Ile Ala Asp Tyr Leu Thr
            260                 265                 270

Arg Tyr Glu His Phe Ser Ser Cys Leu His Gln Val Leu Gly Leu Leu
        275                 280                 285

Asn Gly Lys Asp Pro Asp Ser Ser Lys Val Leu Glu Leu Leu Leu
    290                 295                 300

Ala Phe Cys Ser Val Thr Gln Leu Arg His Met Leu Thr Gln Met Met
305                 310                 315                 320

Phe Glu Gln Ser Pro Pro Gly Ser Ala Thr Leu Gly Ser His Thr Lys
                325                 330                 335

Cys Leu Glu Pro Thr Val Ala Leu Leu Arg Trp Leu Ser Gln Pro Leu
            340                 345                 350

Asp Gly Ser Glu Asn Cys Ser Val Leu Ala Leu Glu Leu Phe Lys Glu
                355                 360                 365

Ile Phe Glu Asp Val Ile Asp Ala Ala Asn Cys Ser Ser Ala Asp Arg
    370                 375                 380

Phe Val Thr Leu Leu Pro Thr Ile Leu Asp Gln Leu Gln Phe Thr
385                 390                 395                 400

Glu Gln Asn Leu Asp Glu Ala Leu Thr Arg Lys Lys Cys Glu Arg Ile
                405                 410                 415

Ala Lys Ala Ile Glu Val Leu Leu Thr Leu Cys Gly Asp Asp Thr Leu
            420                 425                 430

Lys Met His Ile Ala Lys Ile Leu Thr Thr Val Lys Cys Thr Thr Leu
        435                 440                 445

Ile Glu Gln Gln Phe Thr Tyr Gly Lys Ile Asp Leu Gly Phe Gly Thr
    450                 455                 460

Lys Val Ala Asp Ser Glu Leu Cys Lys Leu Ala Ala Asp Val Ile Leu
465                 470                 475                 480

Lys Thr Leu Asp Leu Ile Asn Lys Leu Lys Pro Leu Val Pro Gly Met
                485                 490                 495

Glu Val Ser Phe Tyr Lys Ile Leu Gln Asp Pro Arg Leu Ile Thr Pro
            500                 505                 510

Leu Ala Phe Ala Leu Thr Ser Asp Asn Arg Glu Gln Val Gln Ser Gly
                515                 520                 525

Leu Arg Ile Leu Leu Glu Ala Ala Pro Leu Pro Asp Phe Pro Ala Leu
    530                 535                 540

Val Leu Gly Glu Ser Ile Ala Ala Asn Asn Ala Tyr Arg Gln Gln Glu
545                 550                 555                 560

Thr Glu His Ile Pro Arg Lys Met Pro Trp Gln Ser Ser Asn His Ser
                565                 570                 575

Phe Pro Thr Ser Ile Lys Cys Leu Thr Pro His Leu Lys Asp Gly Val
            580                 585                 590

Pro Gly Leu Asn Ile Glu Glu Leu Ile Glu Lys Leu Gln Ser Gly Met
        595                 600                 605

Val Val Lys Asp Gln Ile Cys Asp Val Arg Ile Ser Asp Ile Met Asp
    610                 615                 620

Val Tyr Glu Met Lys Leu Ser Thr Leu Ala Ser Lys Glu Ser Arg Leu
625                 630                 635                 640

Gln Asp Leu Leu Glu Thr Lys Ala Leu Ala Leu Ala Gln Ala Asp Arg
                645                 650                 655

Leu Ile Ala Gln His Arg Cys Gln Arg Thr Gln Ala Glu Thr Glu Ala
            660                 665                 670

Arg Thr Leu Ala Ser Met Leu Arg Glu Val Glu Arg Lys Asn Glu Glu
```

```
                675                 680                 685
Leu Ser Val Leu Leu Lys Ala Gln Gln Val Glu Ser Glu Arg Ala Gln
        690                 695                 700
Ser Asp Ile Glu His Leu Phe Gln His Asn Arg Lys Leu Glu Ser Val
705                 710                 715                 720
Ala Glu Glu His Glu Ile Leu Thr Lys Ser Tyr Met Glu Leu Leu Gln
                725                 730                 735
Arg Asn Glu Ser Thr Glu Lys Lys Asn Lys Asp Leu Gln Ile Thr Cys
            740                 745                 750
Asp Ser Leu Asn Lys Gln Ile Glu Thr Val Lys Lys Leu Asn Glu Ser
        755                 760                 765
Leu Lys Glu Gln Asn Glu Lys Ser Ile Ala Gln Leu Ile Glu Lys Glu
    770                 775                 780
Glu Gln Arg Lys Glu Val Gln Asn Gln Leu Val Asp Arg Glu His Lys
785                 790                 795                 800
Leu Ala Asn Leu His Gln Lys Thr Lys Val Gln Glu Glu Lys Ile Lys
                805                 810                 815
Thr Leu Gln Lys Glu Arg Glu Asp Lys Glu Thr Ile Asp Ile Leu
            820                 825                 830
Arg Lys Glu Leu Ser Arg Thr Glu Gln Ile Arg Lys Glu Leu Ser Ile
        835                 840                 845
Lys Ala Ser Ser Leu Glu Val Gln Lys Ala Gln Leu Glu Gly Arg Leu
    850                 855                 860
Glu Glu Lys Glu Ser Leu Val Lys Leu Gln Gln Glu Glu Leu Asn Lys
865                 870                 875                 880
His Ser His Met Ile Ala Met Ile His Ser Leu Ser Gly Gly Lys Ile
                885                 890                 895
Asn Pro Glu Thr Val Asn Leu Ser Ile
            900                 905

<210> SEQ ID NO 11
<211> LENGTH: 1520
<212> TYPE: PRT
<213> ORGANISM: Homo sapiens

<400> SEQUENCE: 11

Met Ser Arg Asn Asp Lys Glu Pro Phe Phe Val Lys Phe Leu Lys Ser
1               5                   10                  15
Ser Asp Asn Ser Lys Cys Phe Phe Lys Ala Leu Glu Ser Ile Lys Glu
                20                  25                  30
Phe Gln Ser Glu Glu Tyr Leu Gln Ile Ile Thr Glu Glu Ala Leu
            35                  40                  45
Lys Ile Lys Glu Asn Asp Arg Ser Leu Tyr Ile Cys Asp Pro Phe Ser
    50                  55                  60
Gly Val Val Phe Asp His Leu Lys Lys Leu Gly Cys Arg Ile Val Gly
65                  70                  75                  80
Pro Gln Val Val Ile Phe Cys Met His His Gln Arg Cys Val Pro Arg
                85                  90                  95
Ala Glu His Pro Val Tyr Asn Met Val Met Ser Asp Val Thr Ile Ser
            100                 105                 110
Cys Thr Ser Leu Glu Lys Glu Lys Arg Glu Glu Val His Lys Tyr Val
        115                 120                 125
Gln Met Met Gly Gly Arg Val Tyr Arg Asp Leu Asn Val Ser Val Thr
    130                 135                 140
```

```
His Leu Ile Ala Gly Glu Val Gly Ser Lys Lys Tyr Leu Val Ala Ala
145                 150                 155                 160

Asn Leu Lys Lys Pro Ile Leu Leu Pro Ser Trp Ile Lys Thr Leu Trp
            165                 170                 175

Glu Lys Ser Gln Glu Lys Lys Ile Thr Arg Tyr Thr Asp Ile Asn Met
        180                 185                 190

Glu Asp Phe Lys Cys Pro Ile Phe Leu Gly Cys Ile Ile Cys Val Thr
    195                 200                 205

Gly Leu Cys Gly Leu Asp Arg Lys Glu Val Gln Gln Leu Thr Val Lys
210                 215                 220

His Gly Gly Gln Tyr Met Gly Gln Leu Lys Met Asn Glu Cys Thr His
225                 230                 235                 240

Leu Ile Val Gln Glu Pro Lys Gly Gln Lys Tyr Glu Cys Ala Lys Arg
            245                 250                 255

Trp Asn Val His Cys Val Thr Thr Gln Trp Phe Phe Asp Ser Ile Glu
        260                 265                 270

Lys Gly Phe Cys Gln Asp Glu Ser Ile Tyr Lys Thr Glu Pro Arg Pro
    275                 280                 285

Glu Ala Lys Thr Met Pro Asn Ser Ser Thr Pro Thr Gln Ile Asn Thr
290                 295                 300

Ile Asp Ser Arg Thr Leu Ser Asp Val Ser Asn Ile Ser Asn Ile Asn
305                 310                 315                 320

Ala Ser Cys Val Ser Glu Ser Ile Cys Asn Ser Leu Asn Ser Lys Leu
            325                 330                 335

Glu Pro Thr Leu Glu Asn Leu Glu Asn Leu Asp Val Ser Ala Phe Gln
        340                 345                 350

Ala Pro Glu Asp Leu Leu Asp Gly Cys Arg Ile Tyr Leu Cys Gly Phe
    355                 360                 365

Ser Gly Arg Lys Leu Asp Lys Leu Arg Arg Leu Ile Asn Ser Gly Gly
370                 375                 380

Gly Val Arg Phe Asn Gln Leu Asn Glu Asp Val Thr His Val Ile Val
385                 390                 395                 400

Gly Asp Tyr Asp Asp Glu Leu Lys Gln Phe Trp Asn Lys Ser Ala His
            405                 410                 415

Arg Pro His Val Val Gly Ala Lys Trp Leu Leu Glu Cys Phe Ser Lys
        420                 425                 430

Gly Tyr Met Leu Ser Glu Glu Pro Tyr Ile His Ala Asn Tyr Gln Pro
    435                 440                 445

Val Ile Pro Val Ser His Lys Pro Glu Ser Lys Ala Ala Leu Leu Lys
450                 455                 460

Lys Lys Asn Ser Ser Phe Ser Lys Lys Asp Phe Ala Pro Ser Glu Lys
465                 470                 475                 480

His Glu Gln Ala Asp Glu Asp Leu Leu Ser Gln Tyr Glu Asn Gly Ser
            485                 490                 495

Ser Thr Val Val Glu Ala Lys Ser Glu Ala Arg Pro Phe Asn Asp
        500                 505                 510

Ser Thr His Ala Glu Pro Leu Asn Asp Ser Thr His Ile Ser Leu Gln
    515                 520                 525

Glu Glu Asn Gln Ser Ser Val Ser His Cys Val Pro Asp Val Ser Thr
530                 535                 540

Ile Thr Glu Glu Gly Leu Phe Ser Gln Lys Ser Phe Leu Val Leu Gly
545                 550                 555                 560

Phe Ser Asn Glu Asn Glu Ser Asn Ile Ala Asn Ile Ile Lys Glu Asn
```

-continued

```
                565                 570                 575
Ala Gly Lys Ile Met Ser Leu Leu Ser Arg Thr Val Ala Asp Tyr Ala
                580                 585                 590

Val Val Pro Leu Leu Gly Cys Glu Val Glu Ala Thr Val Gly Glu Val
                595                 600                 605

Val Thr Asn Thr Trp Leu Val Thr Cys Ile Asp Tyr Gln Thr Leu Phe
                610                 615                 620

Asp Pro Lys Ser Asn Pro Leu Phe Thr Pro Val Pro Val Met Thr Gly
625                 630                 635                 640

Met Thr Pro Leu Glu Asp Cys Val Ile Ser Phe Ser Gln Cys Ala Gly
                645                 650                 655

Ala Glu Lys Glu Ser Leu Thr Phe Leu Ala Asn Leu Leu Gly Ala Ser
                660                 665                 670

Val Gln Glu Tyr Phe Val Arg Lys Ser Asn Ala Lys Lys Gly Met Phe
                675                 680                 685

Ala Ser Thr His Leu Ile Leu Lys Glu Arg Gly Gly Ser Lys Tyr Glu
                690                 695                 700

Ala Ala Lys Lys Trp Asn Leu Pro Ala Val Thr Ile Ala Trp Leu Leu
705                 710                 715                 720

Glu Thr Ala Arg Thr Gly Lys Arg Ala Asp Glu Ser His Phe Leu Ile
                725                 730                 735

Glu Asn Ser Thr Lys Glu Arg Ser Leu Glu Thr Glu Ile Thr Asn
                740                 745                 750

Gly Ile Asn Leu Asn Ser Asp Thr Ala Glu His Pro Gly Thr Arg Leu
                755                 760                 765

Gln Thr His Arg Lys Thr Val Val Thr Pro Leu Asp Met Asn Arg Phe
                770                 775                 780

Gln Ser Lys Ala Phe Arg Ala Val Val Ser Gln His Ala Arg Gln Val
785                 790                 795                 800

Ala Ala Ser Pro Ala Val Gly Gln Pro Leu Gln Lys Glu Pro Ser Leu
                805                 810                 815

His Leu Asp Thr Pro Ser Lys Phe Leu Ser Lys Asp Lys Leu Phe Lys
                820                 825                 830

Pro Ser Phe Asp Val Lys Asp Ala Leu Ala Ala Leu Glu Thr Pro Gly
                835                 840                 845

Arg Pro Ser Gln Gln Lys Arg Lys Pro Ser Thr Pro Leu Ser Glu Val
                850                 855                 860

Ile Val Lys Asn Leu Gln Leu Ala Leu Ala Asn Ser Ser Arg Asn Ala
865                 870                 875                 880

Val Ala Leu Ser Ala Ser Pro Gln Leu Lys Glu Ala Gln Ser Glu Lys
                885                 890                 895

Glu Glu Ala Pro Lys Pro Leu His Lys Val Val Cys Val Ser Lys
                900                 905                 910

Lys Leu Ser Lys Lys Gln Ser Glu Leu Asn Gly Ile Ala Ala Ser Leu
                915                 920                 925

Gly Ala Asp Tyr Arg Trp Ser Phe Asp Glu Thr Val Thr His Phe Ile
                930                 935                 940

Tyr Gln Gly Arg Pro Asn Asp Thr Asn Arg Glu Tyr Lys Ser Val Lys
945                 950                 955                 960

Glu Arg Gly Val His Ile Val Ser Glu His Trp Leu Leu Asp Cys Ala
                965                 970                 975

Gln Glu Cys Lys His Leu Pro Glu Ser Leu Tyr Pro His Thr Tyr Asn
                980                 985                 990
```

-continued

```
Pro Lys Met Ser Leu Asp Ile Ser Ala Val Gln Asp Gly Arg Leu Cys
        995                 1000                1005

Asn Ser Arg Leu Leu Ser Ala Val Ser Thr Lys Asp Asp Glu
   1010                1015                1020

Pro Asp Pro Leu Ile Leu Glu Glu Asn Asp Val Asp Asn Met Ala
   1025                1030                1035

Thr Asn Asn Lys Glu Ser Ala Pro Ser Asn Gly Ser Gly Lys Asn
   1040                1045                1050

Asp Ser Lys Gly Val Leu Thr Gln Thr Leu Glu Met Arg Glu Asn
   1055                1060                1065

Phe Gln Lys Gln Leu Gln Glu Ile Met Ser Ala Thr Ser Ile Val
   1070                1075                1080

Lys Pro Gln Gly Gln Arg Thr Ser Leu Ser Arg Ser Gly Cys Asn
   1085                1090                1095

Ser Ala Ser Ser Thr Pro Asp Ser Thr Arg Ser Ala Arg Ser Gly
   1100                1105                1110

Arg Ser Arg Val Leu Glu Ala Leu Arg Gln Ser Arg Gln Thr Val
   1115                1120                1125

Pro Asp Val Asn Thr Glu Pro Ser Gln Asn Glu Gln Ile Ile Trp
   1130                1135                1140

Asp Asp Pro Thr Ala Arg Glu Glu Arg Ala Arg Leu Ala Ser Asn
   1145                1150                1155

Leu Gln Trp Pro Ser Cys Pro Thr Gln Tyr Ser Glu Leu Gln Val
   1160                1165                1170

Asp Ile Gln Asn Leu Glu Asp Ser Pro Phe Gln Lys Pro Leu His
   1175                1180                1185

Asp Ser Glu Ile Ala Lys Gln Ala Val Cys Asp Pro Gly Asn Ile
   1190                1195                1200

Arg Val Thr Glu Ala Pro Lys His Pro Ile Ser Glu Glu Leu Glu
   1205                1210                1215

Thr Pro Ile Lys Asp Ser His Leu Ile Pro Thr Pro Gln Ala Pro
   1220                1225                1230

Ser Ile Ala Phe Pro Leu Ala Asn Pro Val Ala Pro His Pro
   1235                1240                1245

Arg Glu Lys Ile Ile Thr Ile Glu Glu Thr His Glu Glu Leu Lys
   1250                1255                1260

Lys Gln Tyr Ile Phe Gln Leu Ser Ser Leu Asn Pro Gln Glu Arg
   1265                1270                1275

Ile Asp Tyr Cys His Leu Ile Glu Lys Leu Gly Gly Leu Val Ile
   1280                1285                1290

Glu Lys Gln Cys Phe Asp Pro Thr Cys Thr His Ile Val Val Gly
   1295                1300                1305

His Pro Leu Arg Asn Glu Lys Tyr Leu Ala Ser Val Ala Ala Gly
   1310                1315                1320

Lys Trp Val Leu His Arg Ser Tyr Leu Glu Ala Cys Arg Thr Ala
   1325                1330                1335

Gly His Phe Val Gln Glu Glu Asp Tyr Glu Trp Gly Ser Ser Ser
   1340                1345                1350

Ile Leu Asp Val Leu Thr Gly Ile Asn Val Gln Gln Arg Arg Leu
   1355                1360                1365

Ala Leu Ala Ala Met Arg Trp Arg Lys Lys Ile Gln Gln Arg Gln
   1370                1375                1380
```

```
Glu Ser Gly Ile Val Glu Gly Ala Phe Ser Gly Trp Lys Val Ile
    1385                1390                1395

Leu His Val Asp Gln Ser Arg Glu Ala Gly Phe Lys Arg Leu Leu
    1400                1405                1410

Gln Ser Gly Gly Ala Lys Val Leu Pro Gly His Ser Val Pro Leu
    1415                1420                1425

Phe Lys Glu Ala Thr His Leu Phe Ser Asp Leu Asn Lys Leu Lys
    1430                1435                1440

Pro Asp Asp Ser Gly Val Asn Ile Ala Glu Ala Ala Ala Gln Asn
    1445                1450                1455

Val Tyr Cys Leu Arg Thr Glu Tyr Ile Ala Asp Tyr Leu Met Gln
    1460                1465                1470

Glu Ser Pro Pro His Val Glu Asn Tyr Cys Leu Pro Glu Ala Ile
    1475                1480                1485

Ser Phe Ile Gln Asn Asn Lys Glu Leu Gly Thr Gly Leu Ser Gln
    1490                1495                1500

Lys Arg Lys Ala Pro Thr Glu Lys Asn Lys Ile Lys Arg Pro Arg
    1505                1510                1515

Val His
    1520

<210> SEQ ID NO 12
<211> LENGTH: 18
<212> TYPE: PRT
<213> ORGANISM: Homo sapiens

<400> SEQUENCE: 12

Glu Ser Ile Tyr Phe Pro Thr Pro Glu Leu Tyr Asp Pro Glu Asp Thr
1               5                   10                  15

Lys Lys

<210> SEQ ID NO 13
<211> LENGTH: 18
<212> TYPE: PRT
<213> ORGANISM: Homo sapiens

<400> SEQUENCE: 13

Glu Ser Ile Tyr Phe Pro Ser Pro Glu Leu Tyr Asp Pro Glu Asp Thr
1               5                   10                  15

Lys Lys
```

TREATMENT OF HOMOLOGOUS RECOMBINATION DEFICIENT CANCERS

CROSS-REFERENCE TO RELATED APPLICATIONS

This application claims priority to U.S. Provisional Patent Application No. 63/114,838, filed on Nov. 17, 2020, the contents of which is herein incorporated by reference in its entirety.

FIELD OF THE INVENTION

The present application relates to compounds, compositions, and methods for treatment of homologous recombination deficient cancers.

BACKGROUND

The homologous recombination (HR) pathway is essential for high-fidelity DNA double strand break (DSB) repair. HR deficiency results in impaired DSB repair and is a frequent driver of tumorigenesis. The BRCA1 and BRCA2 proteins promote the repair of replication-associated DNA damage by homologous recombination (HR) [Roy, R., et al, Nat Rev Cancer 12, 68-78, 2011]. Acute inactivation of BRCA2 impedes completion of DNA replication [Feng, W. & Jasin, M., Nat Commun 8, 525, 2017], which is associated with rampant chromosome segregation defects and cell lethality. This phenotype is likely shared by BRCA1 since its loss also profoundly impairs cellular fitness [Gowen, L. C., et al, Nat Genet 12, 191-194, 1996]. The lethality of acute depletion of BRCA1/2 suggests that during their evolution towards the malignant phenotype, cells with inactivating mutations in BRCA1 and BRCA2 adapt to the replication-associated problems caused by HR deficiency. Thus, identifying the mechanisms that endow BRCA-deficient cells to complete chromosome duplication and segregation provides new opportunities for therapeutic intervention in HR deficient cancers.

SUMMARY

A method is provided for treating a cancer associated with or characterized by a homologous recombination deficiency ("HR Deficient Cancer"), comprising administering to an individual in need thereof an effective amount of a compound or agent that reduces the ability of TOPBP1 to interact with CIP2A and/or destabilizes or disrupts an existing CIP2A-TOPBP1 interaction ("CIPA2-TOPBP1 Inhibitor").

A method is also provided for inhibiting, reducing or suppressing the growth or survival of cancer cells having HR deficiency ("HR deficient cancer cells"), comprising contacting the cells with an effective amount of a compound or agent that reduces the ability of TOPBP1 to interact with CIP2A and/or destabilizes or disrupts an existing CIP2A-TOPBP1 interaction. In aspects, the cells have one or more of the following: BRCA1, BRCA2, dual BRCA1/BRCA2, PALB2, BARD1, BRIP1, RAD51C and RAD51D defects or mutations associated with HR deficiency ("HR mutant cells"). In aspects the cells have BRCA1, BRCA2, and/or dual BRCA1/BRCA2 defects or mutations ("BRCA mutant cells").

Also provided are CIP2A-TOPBP1 Inhibitors for use in the methods, compositions and uses described herein.

In an aspect, a non-natural, synthetic polypeptide is provided that mimics the protein-protein interface between CIP2A and TOPBP1, allowing it to bind to an endogenous CIP2A or TOPBP1 in physiological, or supraphysiological, conditions and to inhibit the CIP2A from binding to an endogenous TOPBP1.

In aspects, the CIP2A-TOPB1 Inhibitor comprises, is chosen from, or is selected from the group consisting of:
a) a modified peptide or mimetic based on or derived from the region of CIP2A that binds to TOPBP1;
b) a modified peptide or mimetic based on or derived from the region of TOPBP1 that binds to CIP2A;
c) a modified peptide or mimetic, wherein the modified peptide or mimetic comprises at least 6, 10, 20 or 50 amino acids in length and comprises a motif having the sequence: F-D-V or FDVKDALAAL (SEQ ID NO. 9);
d) a peptide or peptidomimetic of CIP2A which mutant comprises amino acids 1 to 560 of SEQ ID NO. 10 or a sequence substantially homologous thereto, and is capable of binding to TOPBP1, in particular amino acids 756-1000 of SEQ ID NO. 11; wherein binding of the peptide or peptidomimetic to TOPBP1 reduces the ability of CIP2A to interact with TOPBP1 and/or destabilizes or disrupts an existing CIP2A-TOPBP1 interaction, either directly or indirectly; and/or
e) a peptide or peptidomimetic of TOPBP1 which mutant: comprises amino acids 756 to 1000, 756-891, 776-851, or 830 to 851 of SEQ ID NO. 11, or a sequence substantially homologous thereto, and is capable of binding to CIP2A, in particular amino acids 1-560 of SEQ ID NO. 10; wherein binding of the peptide or peptidomimetic to CIP2A reduces the ability of TOPBP1 to interact with CIP2A and/or destabilizes or disrupts an existing CIP2A-TOPBP1 interaction, either directly or indirectly.

In an embodiment, the CIP2A-TOPBP1 Inhibitor is a peptide comprising amino acids 1-560 of SEQ ID NO. 10 or a sequence substantially homologous thereto, or fragments thereof, that disrupts the interaction between CIP2A and TOPBP1.

In an embodiment, the CIP2A-TOPBP1 Inhibitor is a peptide comprising amino acids 830-851 of SEQ ID NO. 11 or a sequence substantially homologous thereto, or fragments thereof, that disrupts the interaction between CIP2A and TOPBP1.

In an embodiment, the CIP2A-TOPBP1 Inhibitor is a peptide comprising amino acids 776-851 of SEQ ID NO. 11 or a sequence substantially homologous thereto, or fragments thereof, that disrupts the interaction between CIP2A and TOPBP1.

In an embodiment, the CIP2A-TOPBP1 Inhibitor is a peptide comprising amino acids 756-891 of SEQ ID NO. 11 or a sequence substantially homologous thereto, or fragments thereof, that disrupts the interaction between CIP2A and TOPBP1.

In an embodiment, the CIP2A-TOPBP1 Inhibitor is a peptide comprising amino acids 756-1000 of SEQ ID NO. 11 or a sequence substantially homologous thereto, or fragments thereof, that disrupt the interaction between CIP2A and TOPBP1.

In an embodiment, the CIP2A-TOPBP1 Inhibitor is a peptide comprising the amino acid sequence of SEQ ID NO. 1 or a sequence substantially homologous thereto, that disrupts the interaction between CIP2A and TOPBP1.

In an embodiment, the CIP2A-TOPBP1 Inhibitor is a peptide comprising the amino acid sequence of any one of SEQ ID NO. 1 to 8 or a sequence substantially homologous thereto, that disrupts the interaction between CIP2A and TOPBP1.

Also contemplated are pharmaceutically acceptable salts of the CIP2A-TOPBP1 Inhibitors.

CIP2A-TOPBP1 Inhibitors also include agents identified by screening assays or methods. In aspects, a screening assay or method is provided for identifying agents that disrupt the interaction of CIP2A and TOPBP1 or disrupt the CIP2A-TOPBP1 complex comprising detecting a negative effect of a candidate agent on the interaction or CIP2A-TOPBP1 complex activity, function or expression as compared with a control.

In an embodiment, a method is provided for screening for an inhibitor of the interaction of CIP2A and TOPBP1 comprising: (1) providing a mixture comprising TOPBP1 and CIP2A; (2) contacting the mixture with a candidate agent; (3) determining the binding of TOPBP1 to CIP2A; wherein a statistically significant reduction in the binding of TOPBP1 to CIP2A in the presence of the candidate agent compared to those in the absence of the candidate agent is indicative that the candidate agent is an inhibitor of the interaction of CIP2A and TOPBP1. The disclosure provides an agent or compound identified using a screening assay or method contemplated herein.

The disclosure provides a method for treating a HR Deficient Cancer comprising administering to an individual in need thereof an effective amount of a compound or agent that reduces or inhibits phosphopeptide recognition of TOPB1 BRCT7/8 domains ("BRCT7/8 Agent"). In an aspect, the BRCT7/8 Agent is a compound or agent that binds to TOPB1 BRCT7/8 domains.

A method is also provided for inhibiting, reducing, or suppressing the growth or survival of HR deficient cancer cells, comprising contacting the cells with an BRCT7/8 Agent, in particular a compound or agent that binds TOPB1 BRCT7/8 domains. The disclosure also provides compounds or agents that reduce or inhibit phosphopeptide recognition of TOPB1 BRCT7/8 domains (i.e., BRCT7/8 Agents) for use in methods, compositions and uses described herein. A BRCT7/8 Agent includes compounds and agents identified using an assay or method contemplated herein and/or known in the art.

The disclosure provides a pharmaceutical composition comprising an effective amount of a CIP2A-TOPBP1 Inhibitor or BRCT7/8 Agent for use in treating an HR Deficient Cancer. In an aspect a pharmaceutical composition is provided for inhibiting, reducing or suppressing the growth or survival of cancer cells with HR deficiencies comprising administering an effective amount of a CIP2A-TOPBP1 Inhibitor or BRCT7/8 Agent. In another aspect, a pharmaceutical composition of the disclosure is administered to cancer cells with HR deficiencies. In an embodiment, a pharmaceutical composition of the disclosure is administered to HR mutant cells, in particular BRCA mutant cells.

The disclosure also provides a method for inhibiting, reducing or suppressing the growth or survival of cancer cells with HR deficiencies comprising contacting the cells with an effective amount of a CIP2A-TOPBP1 Inhibitor, or composition of the disclosure. In an aspect, a method is provided for inhibiting, reducing or suppressing the growth or survival of HR mutant cells, in particular BRCA mutant cells, comprising contacting the cells with an effective amount of a CIP2A-TOPBP1 Inhibitor, or composition of the disclosure.

The disclosure also provides the following specific embodiments. 1. A method of treating a cancer associated with or characterized by a homologous recombination (HR) deficiency comprising administering to an individual in need thereof an effective amount of a compound that reduces the ability of TOPBP1 to interact with CIP2A and/or destabilizes or inhibits an existing CIP2A-TOPBP1 interaction.

2. A method for inhibiting, reducing or suppressing the growth or survival of cancer cells with HR deficiencies comprising contacting the cells with an effective amount of a compound that reduces the ability of TOPBP1 to interact with CIP2A and/or destabilizes or inhibits an existing CIP2A-TOPBP1 interaction.

3. A method for inhibiting, reducing or suppressing the growth or survival of cancer cells with HR deficiencies comprising contacting the cells with an effective amount of a compound or agent that reduces or inhibits phosphopeptide recognition of TOPB1 BRCT7/8 domains.

4. The method of embodiment 2 or 3 wherein the cells have BRCA1, BRCA2, dual BRCA1/BRCA2, PALB2, BARD1, BRIP1, RAD51C and/or RAD51D defects or mutations associated with HR deficiency.

5. The method of embodiment 2 or 3 wherein the cells have BRCA1, BRCA2, and/or dual BRCA1/BRCA2 defects or mutations.

6. A non-natural, synthetic polypeptide that mimics the protein-protein interface between CIP2A and TOPBP1 allowing it to bind to an endogenous CIP2A or TOPBP1 in physiological, or supraphysiological, conditions and to inhibit the CIP2A from binding to an endogenous TOPBP1.

7. A CIP2A-TOPBP1 inhibitor or composition comprising, chosen from, or selected from the group consisting of the following:
  a) a modified peptide or mimetic based on or derived from the region of CIP2A that binds to TOPBP1;
  b) a modified peptide or mimetic based on or derived from the region of TOPBP1 that binds to CIP2A;
  c) a modified peptide or mimetic, wherein the modified peptide or mimetic comprises at least 6, 10, 20 or 50 amino acids in length and comprises a motif having the sequence: F-D-V or FDVKDALAAL (SEQ ID NO: 9);
  d) a peptide or peptidomimetic of CIP2A which mutant comprises amino acids 1 to 560 of SEQ ID NO. 10 or a sequence substantially homologous thereto, and is capable of binding to TOPBP1, in particular, amino acids 756-891 of SEQ ID NO. 11; wherein binding of the peptide or peptidomimetic to TOPBP1 reduces the ability of CIP2A to interact with TOPBP1 and/or destabilizes or inhibits an existing CIP2A-TOPBP1 interaction, either directly or indirectly; or
  e) a peptide or peptidomimetic of TOPBP1 which mutant: comprises amino acids 756 to 1000, 756 to 891, 776-851, or 830 to 851 of SEQ ID NO. 11, or a sequence substantially homologous thereto, and is capable of binding to CIP2A, in particular amino acids 1-560 of SEQ ID NO. 10; wherein binding of the peptide or peptidomimetic to CIP2A reduces the ability of TOPBP1 to interact with CIP2A and/or destabilizes or inhibits an existing CIP2A-TOPBP1 interaction, either directly or indirectly;
  f) a peptide comprising amino acids 1-560 of SEQ ID NO. 10 or a sequence substantially homologous thereto, or fragments thereof, that disrupts the interaction between CIP2A and TOPBP1; and/or
  g) a peptide comprising amino acids 776-851, 830-851, 756 to 891, 756 to 1000 of SEQ ID NO. 11 or a sequence substantially homologous thereto, or fragments thereof, that disrupts the interaction between CIP2A and TOPBP1.

8. A method for screening for an inhibitor of the interaction of CIP2A and TOPBP1 comprising: (1) providing a mixture comprising TOPBP1 and CIP2A; (2) contacting the mixture with a candidate agent; (3) determining the binding of TOPBP1 to CIP2A; wherein a statistically significant reduction in the binding of TOPBP1 to CIP2A in the presence of the candidate agent compared to those in the absence of the candidate agent is indicative that the candidate agent is an inhibitor of the interaction of CIP2A and TOPBP1.

9. A CIP2A-TOPBP1 inhibitor comprising a modified polypeptide or compound that interacts or binds with CIP2A or TOPBP1 linked to a moiety that recruits the cellular enzyme E3 ubiquitin ligase.

10. A method of treating a cancer associated with or characterized by a homologous recombination deficiency comprising administering to an individual in need thereof an effective amount of a CIP2A-TOPBP1 Inhibitor of embodiment 7, or 9, or an inhibitor identified by the method of embodiment 8.

11. A pharmaceutical composition comprising an effective amount of a CIP2A-TOPBP1 inhibitor of embodiment 7 or 9, or an inhibitor identified by the method of embodiment 8 and a pharmaceutically acceptable carrier.

12. A method for treating a HR Deficient Cancer comprising administering to an individual in need thereof an effective amount of a compound that reduces or inhibits phosphopeptide recognition of TOPB1 BRCT7/8 domains.

13. A method of embodiment 12 wherein the compound is a phosphopeptide based on or derived from the region of a phosphopeptide that binds to TOPB1 BRCT7/8.

14. A method of embodiment 13 wherein the phosphopeptide that binds to TOPB1 BRCT7/8 is derived from the region of BACH1 that binds to TOPB1 BRCT7/8

15. A method of embodiment 14 wherein the phosphopeptide is Ac-ESIYFpTPELYDPEDTKK-NH$_2$ (SEQ ID NO: 12) or Ac-ESIYFpSPELYDPEDTKK-NH$_2$ (SEQ ID NO: 13).

Other objects features and advantages of the present disclosure will become apparent from the following detailed description. It should be understood, however, that the detailed description and the specific examples while indicating preferred embodiments are given by way of illustration only, since various changes and modifications within the spirit and scope of the disclosure will become apparent to those skilled in the art from this detailed description.

DESCRIPTION OF THE DRAWINGS

FIG. 1A-FIG. 1I show CIP2A loss is synthetic-lethal with BRCA1- or BRCA2-deficiency. (FIG. 1A) Scatter plot of CCA scores for the CRISPR synthetic lethality screens in BRCA1$^{-/-}$ and BRCA2$^{-/-}$ cells. Highlighted in blue are the top 10 genes common to both screens. (FIG. 1B and FIG. 1C) Boxplots of essentiality scores for the indicated genes derived from the Broad (b) and Sanger (c) DepMap projects. Cell lines were grouped according to whether or not they harbored biallelic inactivating mutations in BRCA1 or BRCA2. See FIG. 6B for statistical analysis of the results. (FIG. 1D) Clonogenic survival of RPE1-hTERT p53$^{-/-}$ Cas9 wild-type (WT) and BRCA1$^{-/-}$ cells expressing the indicated CIP2A-targeting sgRNAs or transduced with control lentivirus (CTRL: either empty virus or virus with sgRNA targeting AAVS1). Data was normalized to the plating efficiency of the control virus. Data are shown as mean±S.D. (n=4). (FIG. 1E) Reintroduction of a sgRNA-resistant CIP2A transgene (CIP2A*) rescues lethality of RPE1-hTERT p53$^{-/-}$ Cas9 BRCA1$^{-/-}$ cells caused by sgCIP2A-2. Data are shown as mean±S.D. (n=3). (FIG. 1F) Clonogenic survival of DLD1 wild-type (WT) and BRCA2$^{-/-}$ cells expressing CIP2A- or AAVS1-targeting sgRNAs. Data was normalized to the plating efficiency of cells expressing sgAAVS1. Data are shown as mean±S.D. (n=3). (FIG. 1G) Reintroduction of a sgRNA-resistant CIP2A transgene rescues lethality in DLD1 BRCA2$^{-/-}$ cells caused by sgCIP2A-2. Data are shown as mean±S.D. (n=3). (FIG. 1H) Scatter plot of CCA scores (y-axis) and Bayes Factor (BF) values derived from BAGEL2 (x-axis, for CIP2A$^{-/-}$ cell line) for the CIP2A isogenic synthetic lethal screen. (FIG. 1I) Schematic representation of the CIP2A protein.

FIG. 2A-FIG. 2I show CIP2A prevents acentric chromosome segregation. (FIG. 2A) Analysis of spontaneous sister chromatid exchanges (SCEs) in RPE1-hTERT p53$^{-/-}$ Cas9-derived cell lines of the indicated genotype. The violin plot summarizes data from 3 biological replicates. The blue line is the median and dashed lines are at $1^{st}$ and $3^{rd}$ quartiles. (FIG. 2B) Violin plot of the quantitation of γH2AX foci in S phase cells of RPE1-hTERT wild-type (WT) and indicated CIP2A$^{-/-}$ clones. N>700 cells per conditions. (FIG. 2C) Quantitation of γH2AX and CIP2A IR-induced foci, 1 h post-IR (2 Gy) in interphase DLD1 cells. Plot represents the aggregate of 3 independent experiments. The bar is at the median±S.D. (FIG. 2D) Representative micrographs of the experiment shown in FIG. 2C. (FIG. 2E) Quantitation of γH2AX and CIP2A IR-induced foci, 1 h post-IR (2 Gy) in mitotic DLD1 cells. Plot represents aggregate of 3 independent experiments. The bar is at the median±S.D. (FIG. 2F) Representative micrographs of the experiment shown in FIG. 2E. Scale bar=10 μm. (FIG. 2G) Quantitation of spontaneous CIP2A foci in mitotic DLD1 parental (WT) or BRCA2$^{-/-}$ cells. Plot represents aggregate of 3 independent experiments. The bar is at the median±S.D. (FIG. 2H) Quantitation of radial chromosomes (left) and chromatid breaks (right) in metaphase spreads from RPE1-hTERT p53$^{-/-}$ Cas9 cells upon transduction of virus expressing sgRNAs targeting AAVS1, APEX2 or CIP2A (10 metaphases scored from at least 2 biologically independent experiments). Representative images are shown in FIG. 7E. (FIG. 2I) Quantitation of micronuclei (MNi) staining positive (+) or negative (−) for CENPA in DLD1 cells, parental (WT) or BRCA2$^{-/-}$ (KO), 7 d post-transduction with indicated sgRNAs. Biological replicates are shown and the bars represent the mean±S.D. Representative micrographs are shown on the right. Arrowheads point at micronuclei. Scale bar=10 μm.

FIG. 3A-FIG. 3G show CIP2A co-localizes with TOPBP1 on mitotic structures. (FIG. 3A) Correlation network based on Pearson correlation of gene-level dependency scores (>0.28) derived from the Broad DepMap data. (FIG. 3B) Representative micrograph of an X-irradiated (2 Gy) mitotic U2OS cell treated with 100 ng/mL nocodazole for 16 h and stained with the indicated antibodies. DNA was stained with DAPI. Scale bar=10 μm. (FIG. 3C) Quantitation of MDC1, CIP2A and TOPBP1 IR-induced foci in mitotic U2OS cells treated with nocodazole and the indicated siRNAs (siNT-3 is a non-targeting control). Data is presented as the mean±S.D. (n=3). Representative micrographs are shown in FIG. 8B. (FIG. 3D and FIG. 3E) Types of CIP2A/TOPBP1 structures observed in mitotic cells after treatment with low dose aphidicolin. Maximum intensity projections of confocal z-stacks of U2OS wild type mitotic cells treated with 400 nM aphidicolin for 16 h. Scale bars=10 μm. Besides centrosomes (FIG. 3D, inset ii) that always stain for TOPBP1 and CIP2A regardless of the treatment, small round foci are the most frequently observed structures in response to aphidicolin treatment (FIG. 3D, inset i). Less frequently observed structures include curved and straight filamentous assemblies (FIG. 3E and FIG. 8D). (FIG. 3F) Quantitation of CIP2A and TOPBP1 colocalising foci in U2OS (WT) and MDC1$^{-/-}$ (KO) cells after treatment with 400 nM aphidicolin (16 h). The number of foci per mitotic cell are shown and the bars represent the mean±S.D. (FIG. 3G) Representative micrographs of MDA-MB-436 mitotic cells stained for CIP2A and TOPBP1. DNA was stained with DAPI. Scale bars=10 μm. Quantitation of the percentage of cells with filaments is indicated.

FIG. 4A-FIG. 4J show the CIP2A-TOPBP1 interaction is essential in BRCA2$^{-/-}$ cells. (FIG. 4A) Co-immunoprecipitation of CIP2A with TOPBP1. Whole-cell extracts from 293T cells, untreated or treated with nocodazole for 16 h, were subjected to immunoprecipitation with normal mouse IgG or a CIP2A antibody and were then immunoblotted with TOPBP1 (top) or CIP2A (bottom) antibodies. (FIG. 4B) Schematic of the LacR/LacO assay. (FIG. 4C and FIG. 4D) LacR/LacO assay assessing the interaction of Flag-tagged CIP2A and deletion mutants with LacR-TOPBP1 in U2OS lacO$_{256}$ cells. Quantitation of the assay is in FIG. 4C where 3 biological replicates are shown and the bars represent the mean±S.D. Representative micrographs are shown in FIG. 4D. Scale bar=10 μm. (FIG. 4E) Yeast two-hybrid assay for interaction between TOPBP1 variants and CIP2A (1-560). Expression of proteins was verified by immunoblotting but not shown. (FIG. 4F) LacR/LacO assay assessing the interaction between endogenous CIP2A and TOPBP1 variants fused to Flag-LacR. Data points represent biological replicates and data is presented as the mean±S.D. FL=full-length. (FIG. 4G) Schematic of TOPBP1 and sequence conservation of the minimal CIP2A-interaction motif (SEQ ID NOs 1-8). (FIG. 4H) Quantitation of CIP2A and HA-tagged TOPBP1 mitotic foci in DLD1 cells stably expressing full-length (FL) or the indicated mutants of sgRNA-resistant TOPBP1 (TOPBP1*) or empty virus encoding only the HA tag (EV(HA)) followed by transduction of viruses expressing both Cas9 and sgRNAs targeting TOPBP1 (sgTOPBP1) or AAVS1 (sgAAVS1). Data points represent biological replicates and the bars represent the mean±S.D. (n=3). (FIG. 4I) Clonogenic survival of DLD1 wild-type (WT) and BRCA2$^{-/-}$ cells stably expressing sgRNA-resistant TOPBP1 (TOPBP1*, FL), the indicating TOPBP1 mutants, or an empty virus (EV) followed by inactivation of the chromosomal copies of TOPBP1 with an sgRNA and Cas9 (sgTOPBP1). Quantitation of the data is shown in (i) where representative images of the crystal violet-stained colonies are shown FIG. 9F. Data points represent biological replicates and the error bars represent the mean±S.D. n=3. (FIG. 4J) Quantitation of micronuclei (MNi) in DLD1 wild-type (WT) and BRCA2$^{-/-}$ cells stably expressing sgRNA-resistant TOPBP1 (TOPBP1*), the indicated TOPBP1 mutants, or an empty virus (EV) followed by inactivation of TOPBP1, CIP2A or AAVS1 with the indicated sgRNAs and Cas9. Data points represent biological replicates and the bars represent the mean±S.D. n=3.

FIG. 5A-FIG. 5J show therapeutic proof-of-concept. (FIG. 5A) Schematic of B6L, a fragment derived from TOPBP1 residues 756-1000 fused to the destabilization domain (DD). (FIG. 5B) Quantitation of mitotic CIP2A foci in DLD1 BRCA2$^{-/-}$ upon B6L stabilization. Data is shown as mean±S.D. (n=3). (FIG. 5C) Representative proliferation curves for DLD1 parental (left) and BRCA2$^{-/-}$ (right) cells upon B6L stabilization by Shield-1 treatment (1 μM). Cells were transduced with an empty virus (EV) that expresses the DD domain as control. (FIG. 5D) Aggregate of 3 biological replicates of the experiment shown in FIG. 5C. Data is presented as mean±S.D. (FIG. 5D) Schematic of the experiment shown in FIG. 5F. (FIG. 5F) Clonogenic survival of DLD1 BRCA2$^{-/-}$ cells following expression of B6L for the indicated periods of time. Data is presented as mean±S.D. (n=3). (FIG. 5G) Quantitation of micronuclei (MNi)-positive cells in DLD1 WT or BRCA2$^{-/-}$ cells following addition of AS1. Data presented as mean±S.D. (n=3). (FIG. 5H) Representative proliferation curves for MDA-MB-436 cells upon B6L stabilization by AS1 treatment (1 μM). Cells were transduced with an empty virus (EV) that expresses the DD domain as control. (FIG. 5I) Aggregate of 3 biological replicates of the experiment shown in FIG. 5H. Data presented as the mean±S.D. (FIG. 5J) Model of the BRCA-CIP2A synthetic lethality.

(FIG. 6A) Schematic of the isogenic dropout CRISPR screens to identify synthetic-lethal interactions with BRCA1- and BRCA2-deficiency. (FIG. 6B) Statistical analyses for the data shown in FIG. 1B and FIG. 10. Shown are the results of a Mann-Whitney test comparing the values of the BRCA-proficient (BRCA$^+$) and -deficient (BRCA$^-$) gene depletion scores for the indicated genes. (FIG. 10) Immunoblotting of whole-cell extracts of RPE1-hTERT p53$^{-/-}$ Cas9 cells, parental (WT) or BRCA1$^{-/-}$, expressing the indicated sgRNAs and either a virus expressing an sgRNA-resistant CIP2A (CIP2A*) fused to a FLAG epitope-coding sequence or an empty virus (EV). Lysates were probed for FLAG (exogenous CIP2A), CIP2A and tubulin (loading control). (FIG. 6D and FIG. 6E) Representative images of the clonogenic survival assays shown in FIG. 1D (FIG. 6D) and the images for the DLD1 WT clonogenics relating to FIG. 1F (FIG. 6E).

(FIG. 7A) Clonogenic survival assay of RPE1-hTERT p53$^{-/-}$ Cas9 cells of the indicated genotype following treatment with camptothecin (CPT). Data points represent the mean±S.D. (n=3). WT=wild type. (FIG. 7B) Representative micrographs of metaphase spreads for SCE analysis, relates to FIG. 2A. Arrowheads indicate an SCE event. (FIG. 7C) Immunofluorescence analysis of isogenic RPE1-hTERT p53$^{-/-}$ Cas9-derived WT and CIP2A$^{-/-}$ cells with a CIP2A antibody. Scale bar=10 μm. (FIG. 7D) Representative micrographs of the experiment shown in FIG. 2G. Analysis of spontaneous CIP2A foci in DLD1 WT and BRCA2$^{-/-}$ mitotic cells. Scale bar=10 μm. (FIG. 7E) Representative micrographs of the experiment presented in FIG. 2H showing scored radial chromosomes and chromosomes with chromatid breaks. Arrowheads indicate chromosome aberrations. (FIG. 7F) Representative micrographs of the experiment shown in FIG. 2I. White triangles show cells with micronuclei.

FIG. 8A-FIG. 8F show CIP2A acts in mitosis with TOPBP1. (FIG. 8A) Correlation network based on Pearson correlation of gene-level NormZ derived from the genotoxic dataset shown in Olivieri, M. et al., [Cell 182, 481-496 e421, doi:10.1016/j.cell.2020.05.040 (2020)]. (FIG. 8B) Representative micrographs of the experiment quantitated in FIG. 3C. Nocodazole-treated U2OS cells previously transfected with either a non-targeting siRNA (siNT-3) or the indicated siRNAs were fixed 1 h post-X-irradiation (2 Gy) and processed for immunofluorescence with the indicated antibodies. Scale bar=10 μm. (FIG. 8C) Competitive growth assays in DLD1 Cas9 (WT) or an isogenic BRCA2$^{-/-}$ counterpart transduced with virus expressing the indicated sgRNAs. Data are shown as mean±S.D. (n=3 biologically independent experiments). (FIG. 8D) Additional micrographs of CIP2A/TOPBP1 structures observed in mitotic cells after treatment with low dose aphidicolin. Relates to FIG. 3E. Maximum intensity projections of confocal z-stacks. Scale bar=10 μm. Shown here are curved (upper panels) and straight (lower panels) filaments. (FIG. 8E) Maximum intensity projections of confocal z-stacks of U2OS wild type and MDC1$^{-/-}$ anaphase cells that were either treated with aphidicolin (400 nM) for 16 h or left untreated. Scale bars=10 μm. Quantitation of this experiment is shown in FIG. 3F. (FIG. 8F) Representative micrographs of the experiment shown in FIG. 3G with additional MDA-MB-436 cells showing elongation of CIP2A-TOPBP1 filaments during mitosis. Maximum intensity projections of confocal z-stacks are shown. Scale bar=10 μm.

FIG. 9A-FIG. 9H show CIP2A interacts with TOPBP1 to promote BRCA-deficient cell viability. (FIG. 9A) Representative micrographs of the LacR/LacO assay assessing the interaction between endogenous CIP2A and TOPBP1 variants fused to Flag-LacR shown in FIG. 4F. Representative of 3 independent immunostainings Scale bars=10 μm. (FIG. 9B) LacR/LacO assay assessing the interaction between endogenous CIP2A and TOPBP1 variants fused to Flag-LacR. Data presented as the mean values±S.D. n=3 independent immunostainings; analyzed with one-way ANOVA, followed by multiple comparisons Dunnet test, all compared to FLAG-LacR; ***p=1×10$^{-15}$. (FIG. 9C) Alanine scanning of TOPBP1 (830-851) residues by yeast two-hybrid assay with CIP2A (1-560). These studies identified 5 residues that abolish the TOPBP1-CIP2A interaction when mutated to alanine. AD=activation domain; BD=Gal4 DNA binding domain. Expression of proteins was verified by immunoblotting but not shown. Representative of n=2 independent sets of transformations (FIG. 9D) Immunoblot of whole-cell extracts derived from DLD1 cells transduced with the indicated HA-tagged TOPBP1-expressing lentivirus or an empty virus that expresses an HA epitope (EV(HA)). The lysates were probed with an HA antibody or tubulin (loading control). FL=full-length. (FIG. 9E) Representative micrographs of DLD1 cells transduced with the indicated virus that were arrested in mitosis with a 16 h treatment with nocodazole, exposed to a 2 Gy IR dose and processed for immunofluorescence with the indicated antibodies 1 h later. Relates to the experiment quantitated in FIG. 4h. (FIG. 9F) Representative images of the crystal violet stains of the clonogenic survival experiment presented in FIG. 4I. (FIG. 9G) Representative micrographs of the experiment presented in FIG. 4J showing DAPI-stained cells to monitor micronucleation (labeled with arrowheads). Scale bar=10 mm. (FIG. 9H) CIP2A and TOPBP1 interact directly. Upper: 1 μg of GST or GST-CIP2A (1-560) were separated by SDS-PAGE and stained with Coomassie. Lower blot: GST pull-down experiment with either GST or GST-CIP2A (1-560) incubated with either MBP, MBP-TOPBP1756-999 or MBP-TOPBP1756-999-3A. Bound proteins were processed for immunoblotting with an anti-MBP antibody. The CIP2A/TOPBP1 interaction has been observed >5 times; the loss of interaction by the 3 A mutation is representative of two independent pulldown assays.

FIG. 10A-FIG. 10G show disruption of the TOPBP1-CIP2A interaction is lethal in BRCA-deficient cells. (FIG. 10A) DLD1 BRCA2$^{-/-}$ cells transduced with either an empty virus containing only the destabilization domain (DD; EV, left) or a virus encoding B6L were treated with Shield-1 (1 μM) for the indicated periods or left untreated (UT). Shown are micrographs of mitotic cells stained for CIP2A, γH2AX or FLAG (labeling the DD). DNA was stained with DAPI. Scale bar=10 μm. Quantitation of the experiment is shown in FIG. 5B. (FIG. 10B) Anti-FLAG immunoblots of whole-cell extracts derived from DLD1 parental (WT) or BRCA2$^{-/-}$ cells treated with either Shield-1 (S1) or Aqua-Shield-1 (AS1) for 72 h. These blots show similar induction of DD (in the empty virus; EV) or B6L upon addition of compound. Anti-KAP1 immunoblotting is used as a loading control. (FIG. 10O) Representative images of the clonogenic survival experiment presented in FIG. 5F. (FIG. 10D) Immunoblots assessing ATR signaling (CHK1 S345 phosphorylation) in DLD1 cells transduced with either an empty virus (EV) that expresses the unfused DD domain or a virus expressing B6L following induction with AS1. Cells were treated with hydroxyurea (HU) for the indicated times prior to harvesting. (FIG. 10E) Anti-FLAG immunoblots of whole-cell extracts derived from MDA-MB-436 cells treated with Aqua-Shield-1 (AS1) for 72 h. Anti-KAP1 immunoblotting is used as loading control. (FIG. 10F) Quantitation of the of micronuclei (MNi)-positive cells in MDA-MB-436 transduced with an either empty virus (EV) or B6L-expressing virus following addition of AS1. Data is presented as mean±S.D. (n=3). (FIG. 10G) Competitive growth assays in wild-type or RPE1-hTERT p53$^{-/-}$ Cas9 (WT) or isogenic BRCA1$^{-/-}$ or BRCA1$^{-/-}$53 BP1$^{-/-}$ counterparts transduced with virus expressing the indicated sgRNAs. Data are shown as mean±S.E.M. (n=3 biologically independent experiments). Please note that the 53BP1$^{-/-}$ cell line was also subjected to transduction but is not shown for clarity.

(FIG. 11A) Clonogenic survival of DLD1 wild-type (WT) and BRCA2$^{-/-}$ (KO) cells stably expressing different variants of sgRNA-resistant TOPBP1 (TOPBP1*) or an empty virus (EV) followed by inactivation of endogenous TOPBP1 or AAVS1 with the indicated sgRNAs and Cas9. Data points represent biological replicates (n=3). (FIG. 11B) Representative images of the crystal violet stained colonies.

DEFINITIONS

Figure 6A:
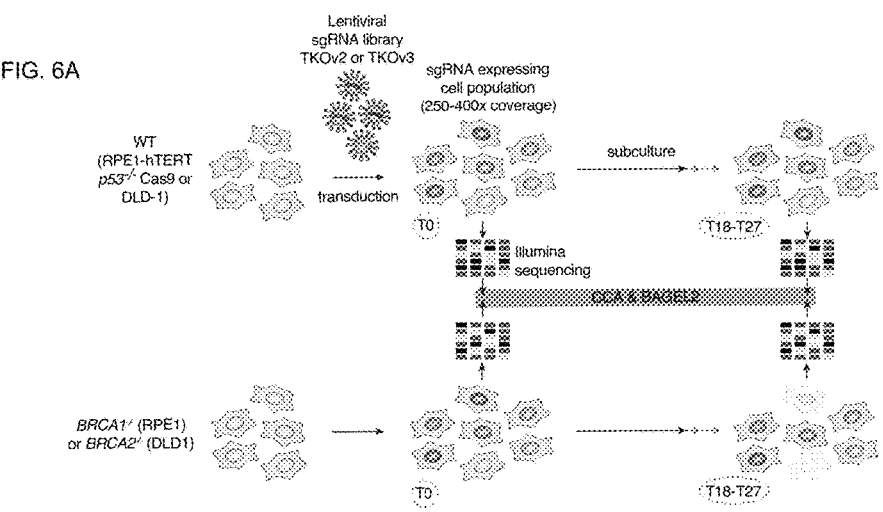
FIG. 6A-FIG. 6E show supporting data on the identification of CIP2A as synthetic lethal with BRCA1- and BRCA2-deficiency.

As used herein and in the appended claims, the singular forms "a", "an", and "the" include plural reference unless the context clearly dictates otherwise. As used herein, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The terms "administering" and "administration" refer to the process by which a therapeutically effective amount of a compound, agent or composition contemplated herein is delivered to a subject for treatment purposes. Compositions are administered in accordance with good medical practices taking into account the subject's clinical condition, the site and method of administration, dosage, patient age, sex, body weight, and other factors known to physicians.

The term "CIP2A" or "CIP2A polypeptide" is used in accordance with its customary meaning in the art and refers to a protein (including without limitation, fragments, isoforms, homologous proteins, oligopeptides, homodimers, heterodimers, protein variants, modified proteins, derivatives, analogs, and fusion proteins, among others) with CIP2A2 function and/or activity. The proteins include natural or naturally occurring proteins, recombinant proteins, synthetic proteins, or a combination thereof with CIP2A function and/or activity. CIP2A encodes a protein of 905 amino acid residues comprising a highly structured N-terminal region consisting of an armadillo (arm) repeat core (residues 1-560) [Wang, J. et al. EMBO Rep 18, 437-450, doi:10.15252/embr.201642788 (2017)] and a C-terminal region predicted to form a coiled-coil [Wang, J. et al. supra (2017); (FIG. 11)]. Exemplary human and mouse CIP2A proteins have the following accession numbers: UniProtKB—Q8TCG1 (CIP2A_HUMAN) (SEQ ID NO. 11); XP_006713779.1, XP_006713780.1, XP_011511358.1, XP_011511359.1, NP_065941.2 (all incorporated by reference). The term includes any recombinant or naturally occurring form of CIP2A or variants thereof that maintain CIP2A function or activity (e.g. within at least 30%, 40%, 50%, 60%, 70%, 80%, 90%, 95%, or 100% activity compared to wildtype protein). In embodiments, the CIP2A is a human CIP2A. In embodiments, the CIP2A has the amino acid sequence of SEQ ID NO. 10.

A "composition" refers to a mixture of at least one CIPA2-TOPBP1 Inhibitor or BRCT7/8 Agent, with other chemical components, such as carriers, stabilizers, diluents, dispersing agents, suspending agents, thickening agents, and/or excipients. A "composition" also includes at least one CIPA2-TOPBP1 Inhibitor and at least one chemotherapeutic agent, or at least one BRCT7/8 Agent and at least one chemotherapeutic agent. A composition facilitates administration of the compound to a cell or organism. Multiple techniques of administering a compound exist in the art including, but not limited to, intravenous, oral, aerosol, parenteral, ophthalmic, pulmonary and topical administration. Guidance for preparing pharmaceutical compositions may be found, for example, in Remington: The Science and Practice of Pharmacy, (20th ed.) ed. A. R. Gennaro A. R., 2000, Lippencott Williams & Wilkins.

"Decrease", "reduce", "reduction", "inhibit" are all used herein generally to refer to a decrease by a statistically significant amount. The decrease can be, for example, a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level or non-detectable level as compared to a reference level), or any decrease between 10-100% as compared to a reference level. The decrease or inhibition may be a decrease in activity, interaction, expression, function, response, condition, disease, or other biological parameter. This can include but is not limited to the complete ablation of the activity, interaction, expression, function, response, condition or disease.

An "effective amount" refers to an amount of a CIPA2-TOPBP1 Inhibitor, BRCT7/8 Agent, or composition, as disclosed herein, effective to achieve a particular biological result. Such results include, without limitation, the treatment of a disease or condition disclosed herein as determined by any means suitable in the art.

"HR Deficient Cancer" refers to any cancer associated with or characterized by a HR deficiency. A HR deficiency may be associated with genetic or epigenetic alterations in the FA-BRCA pathway. In embodiments, the HR Deficient Cancer is associated with a HR deficiency associated with germline mutations of the tumor suppressors BRCA1 and BRCA2 (Venkitaraman A R. Linking the cellular functions of BRCA genes to cancer pathogenesis and treatment. Annu Rev Pathol. 2009; 4:461-487). In embodiments, the HR Deficient Cancer is associated with a HR deficiency associated with genetic and epigenetic inactivation of homologous recombination components broadly termed BRCAness (Turner N, et al, Hallmarks of 'BRCAness' in sporadic cancers. Nat Rev Cancer. 2004; 4(10):814-819. 6; Lord C J, Ashworth A. BRCAness revisited. Nat Rev Cancer. 2016; 16(2):110-120. 7 and Konstantinopoulos P A, et al. Homologous recombination deficiency: Exploiting the fundamental vulnerability of ovarian cancer. Cancer Discov. 2015; 5(11): 1137-1154). An HR Deficient Cancer may be associated with sensitivity to platinum and PARP inhibitors (Panagiotis A. et al., Homologous Recombination Deficiency: Exploiting the Fundamental Vulnerability of Ovarian Cancer. Cancer Discov. 2015 November; 5(11): 1137-1154; Timms K M, et al., Association of BRCA1/2 defects with genomic scores predictive of DNA damage repair deficiency among breast cancer subtypes. Breast Cancer Res 2014; 16:4750).

In embodiments, the HR Deficient Cancer is associated with BRCA1, BRCA2, dual BRCA1/BRCA2, PALB2, BARD1, BRIP1, RAD51C and/or RAD51D defects or mutations. In embodiments, the HR Deficient Cancer is associated with PALB2, BARD1, BRIP1, RAD51C and/or RAD51D defects or mutations. In embodiments, the HR Deficient Cancer is associated with BRCA1, BRCA2, and/or dual BRCA1/BRCA2 defects or mutations.

HR deficiency may be determined, for example, by the following: clinical phenotype; gene expression profiles of BRCAness or DNA repair, evaluating BRCA1 protein expression by immunohistochemistry, assessing tumor genome nucleotide sequences and mutational spectrums, or "sequence scars" characteristic of defective DNA repair via HR; targeted mutational profiling of HR genes using next-generation sequencing; BROCA targeted capture and massively parallel sequencing assay that identifies all types of mutations of key HR genes, including single-base substitutions, small insertions and deletions, and large gene rearrangements; determining the following scores: whole-genome tumor LOH scores, telomeric allelic imbalance (TAI) score, and large-scale state transitions (LST) score, and sensitivity to platinum compounds such as cisplatin; and/or, direct assessment of RAD51 foci formation via immunofluorescence or by assessing other DNA repair complexes via immunohistochemistry [Panagiotis A. et al. supra, 2015].

Embodiments of the disclosure provide for treatment of various cancers including but not limited to carcinomas, melanomas, lymphomas, sarcomas, blastomas, leukemias, myelomas, osteosarcomas and neural tumors. In embodiments, the cancer is breast, ovarian, pancreatic or prostate cancer.

In aspects, treatment of cancer cells with one or more of the following: BRCA1, BRCA2, dual BRCA1/BRCA2, PALB2, BARD1, BRIP1, RAD51C and RAD51D defects or mutations associated with HR deficiency ("HR mutant cells") is provided. In embodiments, treatment of cancer cells with BRCA1 defects, BRCA2 defects, and/or dual BRCA1/BRCA2 defects or mutations ("BRCA mutant cells") is provided. In embodiments, treatment of resistant BRCA 1-deficient cancer cells is provided. In some embodiments, the cancer is breast cancer, in particular invasive ductal carcinoma and invasive lobular carcinoma. In some embodiments, the cancer is ovarian cancer, in particular epithelial ovarian tumors, germ cell ovarian tumors, and sex cord stromal tumors.

In aspects the HR Deficient Cancer is a cancer in a subject whose tumors or cancer progresses on PARP Inhibitor therapy.

In aspects, the HR Deficient Cancer is a BRCA 1-mutated cancer with loss of the 53BP1 pathway.

"Sample" refers to a biological sample, including without limitation a biopsy sample, blood-derived sample, urine sample, saliva, spinal fluid, pulmonary, nasal, vaginal, ocular, peritoneal, throat, urethral, cell or tissue sample, cell culture and/or fraction thereof. A sample may be previously collected from the individual for whom the efficiency of an agent must be determined, or from another individual, and/or a group of individuals. A sample may also comprise a non-biological sample depending on a method that is being performed.

"Mimetic" refers to compounds which mimic the activity of a peptide, and they may comprise amino acids linked by non-peptide bonds. (See U.S. Pat. No. 5,637,677 and its parent applications for detailed guidance on the production of mimetics.)

"PARP Inhibitor" refers to an inhibitor of the nuclear enzyme poly(adenosine 5'-diphospho-ribose) polymerase ["poly(ADP-ribose) polymerase" or "PARP", which is also referred to as ADPRT (NAD: protein (ADP-ribosyl transferase (polymerising)) and PARS (poly(ADP-ribose) synthetase). The term includes agents that target PARP1 and/or PARP2. PARP Inhibitors have been described in Banasik et al., "Specific Inhibitors of Poly(ADP-Ribose) Synthetase and Mono(ADP-Ribosyl)-Transferase", J. Biol. Chem., 267: 3, 1569-75 (1992), and in Banasik et al., "Inhibitors and Activators of ADP-Ribosylation Reactions", Molec. Cell. Biochem., 138, 185-97 (1994). PARP inhibitors have also been disclosed and described in many patents and patent applications including the following: WO 00/42040; WO 00/39070; WO 00/39104; WO 99/11623; WO 99/11628; WO 99/11622; WO 99/59975; WO 99/11644; WO 99/11945; WO 99/11649; and WO 99/59973; U.S. Pat. Nos. 8,894,989, 8,946,221; 8,778,966; 8,669,249; 8,623,884; 8,592,416; 8,546,368; 8,541,417; 8,541,403; 8,420,650; 8,362,030; 8,236,802; 8,217,070; 8,188,103; 8,188,084; 8,183,250; 8,173,682; 8,129,382; 8,088,760; 8,080,557; 8,071,623; 8,058,275; 8,012,976; 8,008,491; 7,999,117; 7,956,064; 7,875,621; 7,820,668; 7,750,008; 7,732,491; 7,728,026; 7,652,014; 7,601,719; 7,462,724; 7,087,637; 7,041,675; 6,977,298; 6,924,284; 6,737,421; 6,635,642; 6,495,541; 6,444,676; 6,395,749; 6,380,211; 6,380,193; 6,346,536; 6,197,785; 5,756,510; and Re. 36,397.

In aspects, the PARP inhibitor is an agent that targets PARP1 and/or PARP2. In an aspect, the PARP Inhibitor is veliparib, rucaparib, niraparib, olaparib, iniparib, talazoparib, JPI-289, CEP-9722, GPI 2016, and INO-1001, or other known PARP inhibitors.

In aspects, the PARP inhibitor is Olaparib (AstraZeneca). In aspects, the PARP inhibitor is Veliparib (AbbVie Inc, Chicago, IL). In aspects, the PARP inhibitor is Rucaparib (Clovis Oncology, Inc., Boulder, CO). In aspects, the PARP inhibitor is INO-1001 (Inotek Pharmaceuticals Corp, Lexington, MA). In aspects, the PARP inhibitor is niraparib (Tesaro, Waltham, MA, also see Montoni et al, Frontiers in Pharmacology, [4], Article 18, pages 1-7). In aspects, the PARP inhibitor is talazoparib (Medivation, Inc, San Francisco CA). In aspects, the PARP inhibitor is talazoparib (Pfizer).

"ATR Inhibitor" refers to an inhibitor of ataxia-telangiectasia-mutated-and-Rad3-related kinase. ATR Inhibitors have been described in the art (see for example, Zhaojun Qiu et al., Radiother Oncol. 2018 March; 126(3):450-464. doi: 10.1016/j.radonc.2017.09.043 and Hustedt, N. et al, *Open Biol* 9, 190156, doi:10.1098/rsob.190156 (2019).) Examples of ATR Inhibitors include without limitation, Schisandrin B, NU6027, NVP-BEZ235, torin 2, ETP-46464, VE-821, VE-822, AZ20, RP-3500, ART0380, BAY1895344, M4344 and AZD6738, and other known ATR inhibitors "Pharmaceutically acceptable" refers to those compounds, agents, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

"Pharmaceutically acceptable carrier" includes any of the standard pharmaceutical carriers, such as a phosphate buffered saline solution, water, emulsions such as an oil/water or water/oil emulsion, and various types of wetting agents. The term also includes any of the agents approved by a regulatory agency such as the FDA or listed in the US Pharmacopeia for use in animals, including humans.

"Pharmaceutically acceptable salt" refers to salts of compounds that retain the biological activity of the parent compound, and which are not biologically or otherwise undesirable. Salts may be prepared by conventional means from the corresponding free base compound by reacting, for example, the appropriate acid or base with the corresponding free base. Examples of pharmaceutically acceptable salts are described in Remington: The Science and Practice of Pharmacy, (20th ed.) ed. A. R. Gennaro A. R., 2000, Lippencott Williams & Wilkins or in Handbook of Pharmaceutical Salts, Properties, Selection and Use, e.d. P. H. Stahl, C. G. Wermuth, 2002, jointly published by Verlag Helvetica Chimica Acta, Zurich, Switzerland, and Wiley-VCH, Weinheim, Germany.

"Polypeptide" or "protein" refers to any chain or chains of two or more amino acids and encompasses a singular "polypeptide" or "protein" as well as plural "polypeptides" or "proteins". Any other term used to refer to a chain or chains of two or more amino acids, such as "peptide" or "amino acid sequence" are included in the definition of a "polypeptide" or "protein" even though each of these terms can have a more specific meaning. The term additionally includes polypeptides which have undergone post-translational or post-synthesis modifications, including without limitation, glycosylation, acetylation, phosphorylation, amidation, derivatization by known protecting/blocking groups, proteolytic cleavage, or modification by non-naturally occurring amino acids. More specifically, a "peptide" as used herein comprises full length peptides and fragments, variants or derivatives thereof. A "peptide" can be part of a fusion polypeptide comprising additional components and can also be derivatized.

The terms "subject", "individual" or "patient" refer, interchangeably, to a warm-blooded animal such as a mammal. In particular, the term refers to a human. A subject, individual or patient may be afflicted with or suspected of having or being pre-disposed to a disease as described herein. The term also includes animals bred for food, as pets, or for study including horses, cows, sheep, poultry, fish, pigs, cats, dogs, and zoo animals, goats, apes (e.g. gorilla or chimpanzee), and rodents such as rats and mice.

The term "substantially homologous" as used herein in connection with an amino acid or nucleic acid sequence includes sequences having at least 70% or 75%, preferably at least 80%, and even more preferably at least 85%, 90%, 95%, 96%, 97%, 98% or 99%, sequence identity to the amino acid or nucleic acid sequence disclosed. Substantially homologous sequences thus include single or multiple base or amino acid alterations (additions, substitutions, insertions or deletions) to the sequences disclosed herein. In certain embodiments, at the amino acid substantially homologous sequences contain only 1, 2, 3, 4, 5, 6, 7, 8, 9, or 10 substituted amino acids as compared to the reference sequence. Said substitutions can be with conservative or non-conservative amino acids. The term "substantially homologous" also includes modifications or chemical equivalents of the amino acid and nucleotide sequences as described herein that perform substantially the same function as the proteins or nucleic acid molecules in substantially the same way. The term 'TOPBP1', "TOPBP1 polypeptide", or "DNA topoisomerase 2-binding protein 1", is used in accordance with their customary meaning in the art and refers to a protein (including without limitation, fragments, isoforms, homologous proteins, oligopeptides, homodimers, heterodimers, protein variants, modified proteins, derivatives, analogs, and fusion proteins, among others) with TOPBP1 function and/or activity. The proteins include natural or naturally occurring proteins, recombinant proteins, synthetic proteins, or a combination thereof) with TOPBP1 function and/or activity. Exemplary human and mouse TOPBP1 proteins have the following accession numbers: UniProtKB—Q92547 (TOPBP1_HUMAN); NCBI Reference Sequences: NP_008958.2 (human), NP_001350818.1 (human), and NP_795953.2 (mouse); and, GenBank Accession No. AAI26210 (all incorporated by reference). [See also Yamane K., Kawabata M., Tsuruo T. (1997) Eur. J. Biochem. 250, 794-799; Garcia V., Furuya K., Carr A. M. (2005) DNA Repair 4, 1227-1239 and Leung C C, et al, J Biol Chem. 2011 Feb. 11:286(6):4292-301. dal: 10.1074/jbc.M110.189555.] TopBP1 possesses nine BRCT domains (Yamane, K., et al. (1997) Eur. J. Biochem. 250, 794-799 8 and Garcia, V., et al (2005) DNA Repair 4, 1227-1239). BRCT domains are phosphorylated protein-binding modules (Manke, I. A., et al. (2003) Science 302, 636-639 12 and Yu, X., et al (2003) Science 302, 639-642) and the role of tandem BRCT domains in recognizing phosphopeptide motifs is well established. The BRCT7/8 tandem pair of TopBP1 functionally interacts with a distinct phosphorylated region of BACH1 (Gong, Z., et al (2010) Mol. Cell 37, 438-446). TOPBP1 BRCT7/8 domains recognize both Ser (P) and Thr(P) peptides (Leung C C, et al., J Biol Chem. (2011) Feb. 11; 286(6):4292-301. Doi 10.1074/jbc.M110.189555).

The term includes any recombinant or naturally-occurring form of TOPBP1 or variants thereof that maintain TOPBP1 function or activity (e.g. within at least 30%, 40%, 50%, 60%, 70%, 80%, 90%, 95%, or 100% activity compared to wildtype protein). In embodiments, the TOPBP1 is a human TOPBP1. In embodiments, the TOPBP1 has the amino acid sequence of SEQ ID NO. 11.

DETAILED DESCRIPTION

CIP2A-TOPBP1 Inhibitors and BRCT7/8 Agents

The disclosure provides CIP2A-TOPBP1 Inhibitors for use in the methods, compositions, uses, and kits described herein. A CIP2A-TOPBP1 Inhibitor reduces the ability of TOPBP1 to interact with CIP2A and/or destabilizes or disrupts an existing CIP2A-TOPBP1 interaction. In aspects, a CIP2A-TOPBP1 inhibitor is a compound that negatively affects (e.g., decreases) the activity, expression, and/or function of a CIP2A-TOPBP1 complex relative to the activity, expression and/or function of the complex in the absence of the inhibitor (e.g., the CIP2A-TOPBP1 inhibitor binds CIP2A or TOPBP1). In embodiments, a CIP2A-TOPBP1 Inhibitor reduces the activity, expression or function of a CIP2-TOPBP1 complex by direct interaction with CIP2A, TOPBP1 or the CIP2A-TOPBP1 complex. In embodiments, CIP2A-TOPBP1 Inhibitor mimics the protein-protein interface between CIP2A and TOPBP1. In embodiments, a CIP2A-TOPBP1 Inhibitor reduces the activity, expression, function of a CIP2-TOPBP1 complex by indirect interaction (e.g., the inhibitor binds to a protein that inactivates CIP2A, TOPBP1 or CIP2A-TOPBP1 complex). In aspects, a CIP2A-TOPBP1 Inhibitor inhibits HR deficient cancer cells from completing duplication and segregation. In aspects, a CIP2A-TOPBP1 Inhibitor is toxic for, or causes death in HR deficient cancer cells. In aspects, a CIP2A-TOPBP1 Inhibitor inhibits HR mutant cells, in particular BRCA mutant cells, from completing duplication and segregation. In aspects, a CIP2A-TOPBP1 Inhibitor is toxic for, or causes death in HR mutant cells, in particular, BRCA mutant cells.

A CIP2A-TOPBP1 Inhibitor may be a modified CIP2A polypeptide or TOPBP1 polypeptide. Modifications of polypeptides include without limitation, substitutions of amino acids, insertions, deletions or chemical modifications. Techniques known per se for the modification of one or more amino acids are available to those skilled in the art (see for example, Sambrook et al. Molecular Cloning: A Laboratory Manual, Second Edition, Cold Spring Harbor Laboratory Press, 1989 and Third Edition, 2001; Ausubel et al., Current Protocols in Molecular Biology, John Wiley & Sons, New York, 1987 and periodic updates). In aspects, amino acid modifications can be selected by means of computational analysis based on the structural data for the CIPA2-TOPBP1 complex. ProSAII software ("Protein Structure Analysis"; Proceryon Biosciences, Salzburg) may also be used to determine protein stability for the polypeptides.

A modified polypeptide may be identified by its affinity to the binding region of its interacting polypeptide in the CIP2A-TOPBP1 complex. Affinity may be determined by suitable assays known to those skilled in the art. Affinity may also be determined by assessing recruitment to DSB sites. In an aspect, a polypeptide disclosed herein has a quantifiable binding affinity to the domain of its interacting polypeptide of 0.5 to $15 \times 10^{-9}$M, 0.5 to $25 \times 10^{-9}$M, 0.5 to $50 \times 10^{-9}$ M, 0.5 to $100 \times 10^{-9}$ M, 0.5 to $200 \times 10^{-9}$ M, 1 to $200 \times 10^{-9}$ M, 1 to $300 \times 10^{-9}$M, 1 to $400 \times 10^{-9}$M, 1 to $500 \times 10^{-9}$M, 100 to $300 \times 10^{-9}$ M, 100 to $250 \times 10^{-9}$ M, or 200 to $250 \times 10^{-9}$ M.

A CIP2A-TOPBP1 Inhibitor may be a peptide or mimetic based on or derived from the region of CIP2A that binds to TOPBP1, or the region of TOPBP1 that binds to CIP2A. A CIP2A-TOPBP1 Inhibitor may be a peptide or mimetic that mimics the protein-protein interface between CIP2A and TOPBP1.

In an embodiment, the CIP2A-TOPBP1 Inhibitor is a modified peptide or mimetic, wherein the modified peptide or mimetic comprises at least 6, 10, 20 or 50 amino acids in length and comprises a motif having the sequence F-D-V, or a pharmaceutically acceptable salt thereof.

In an embodiment, the CIP2A-TOPBP1 Inhibitor is a modified peptide or mimetic, wherein the modified peptide or mimetic comprises at least 6, 10, 20 or 50 amino acids in length and comprises a motif having the sequence FDVK-DALAAL (SEQ ID NO. 9), or a pharmaceutically acceptable salt thereof.

In an embodiment, the CIP2A-TOPBP1 Inhibitor is an engineered modified peptide or peptidomimetic of CIP2A which mutant: comprises amino acids 1 to 560 of SEQ ID NO. 10 or a sequence substantially homologous thereto, and is capable of binding to TOPBP1, in particular amino acids 830-851, 776-851, 756-891, or 756-1000 of SEQ ID NO. 11; wherein binding of the peptide or peptidomimetic to TOPBP1 reduces the ability of CIP2A to interact with TOPBP1 and/or destabilizes or disrupts an existing CIP2A-TOPBP1 interaction, either directly or indirectly. In embodiments, the sequence of the engineered modified peptide or peptidomimetic of CIP2A comprises one or more mutations compared to the amino acid sequence of a naturally occurring CIP2A, which mutations are selected from a deletion, a substitution and an insertion;

In an embodiment, the CIP2A-TOPBP1 Inhibitor is an engineered modified peptide or peptidomimetic of a TOPBP1 which mutant: comprises amino acids 756 to 1000 of SEQ ID NO. 11 or a sequence substantially homologous thereto and is capable of binding to CIP2A, in particular amino acids 1-560 of SEQ ID NO. 10; wherein binding of the peptide or peptidomimetic to CIP2A reduces the ability of TOPBP1 to interact with CIP2A and/or destabilizes or disrupts an existing CIP2A-TOPBP1 interaction, either directly or indirectly.

In an embodiment, the CIP2A-TOPBP1 Inhibitor is an engineered modified peptide or peptidomimetic of TOPBP1 which mutant: comprises amino acids 830 to 851 of SEQ ID NO. 11 or a sequence substantially homologous thereto and is capable of binding to CIP2A, in particular amino acids 1-560 of SEQ ID NO. 10; wherein binding of the peptide or peptidomimetic to CIP2A reduces the ability of TOPBP1 to interact with CIP2A and/or destabilizes or disrupts an existing CIP2A-TOPBP1 interaction, either directly or indirectly.

In an embodiment, the CIP2A-TOPBP1 Inhibitor is an engineered modified peptide or peptidomimetic of TOPBP1 which mutant: comprises amino acids 776 to 851 of SEQ ID NO. 11 or a sequence substantially homologous thereto and is capable of binding to CIP2A, in particular amino acids 1-560 of SEQ ID NO. 10; wherein binding of the peptide or peptidomimetic to CIP2A reduces the ability of TOPBP1 to interact with CIP2A and/or destabilizes or disrupts an existing CIP2A-TOPBP1 interaction, either directly or indirectly.

In an embodiment, the CIP2A-TOPBP1 Inhibitor is an engineered modified peptide or peptidomimetic of TOPBP1 which mutant: comprises amino acids 756 to 891 of SEQ ID NO. 11 or a sequence substantially homologous thereto and is capable of binding to CIP2A, in particular amino acids 1-560 of SEQ ID NO. 10; wherein binding of the peptide or peptidomimetic to CIP2A reduces the ability of TOPBP1 to interact with CIP2A and/or destabilizes or disrupts an existing CIP2A-TOPBP1 interaction, either directly or indirectly.

In embodiments, the sequence of the engineered modified peptide or peptidomimetic of TOPBP1 comprises one or more mutations compared to the amino acid sequence of a naturally-occurring TOPBP1, which mutations are selected from a deletion, a substitution and an insertion.

In an embodiment, the CIP2A-TOPBP1 Inhibitor is a peptide comprising amino acids 1-560 of SEQ ID NO. 10 or a sequence substantially homologous thereto, or fragments thereof, that destabilizes or disrupts the interaction between CIP2A and TOPBP1.

In an embodiment, the CIP2A-TOPBP1 Inhibitor is a peptide comprising amino acids 830-851 of SEQ ID NO. 11 or a sequence substantially homologous thereto, or fragments thereof, that destabilizes or disrupts the interaction between CIP2A and TOPBP1.

In an embodiment, the CIP2A-TOPBP1 Inhibitor is a peptide comprising amino acids 776-891 of SEQ ID NO. 11 or a sequence substantially homologous thereto, or fragments thereof, that destabilizes or disrupts the interaction between CIP2A and TOPBP1.

In an embodiment, the CIP2A-TOPBP1 Inhibitor is a peptide comprising amino acids 756-891 of SEQ ID NO. 11 or a sequence substantially homologous thereto, or fragments thereof that destabilizes or disrupts the interaction between CIP2A and TOPBP1.

In an embodiment, the CIP2A-TOPBP1 Inhibitor is a peptide comprising amino acids 756-1000 of SEQ ID NO. 11 or a sequence substantially homologous thereto, or fragments thereof, that destabilizes or disrupts the interaction between CIP2A and TOPBP1.

The disclosure provides compounds or agents that reduce or inhibit phosphopeptide recognition of TOPB1 BRCT7/8 domains (i.e., BRCT7/8 Agents) for use in the methods, compositions and uses described herein. In aspects, a BRCT7/8 Agent is a phosphopeptide based on or derived from the region of a phosphopeptide that binds to TOPB1 BRCT7/8. In an aspect, a phosphopeptide that binds to TOPB1 BRCT7/8 is derived from the region of BACH1 that binds to TOPB1 BRCT7/8 (Leung C C, et al., J Biol Chem. 2011 Feb. 11; 286(6):4292-301. Doi 10.1074/jbc.M110.189555). In an embodiment, the BRCT7/8 Agent is Ac-ESIYFpTPELYDPEDTKK-NH$_2$ (SEQ ID NO: 12) or Ac-ESIYFpSPELYDPEDTKK-NH$_2$ (SEQ ID NO: 13).

A modified polypeptide. peptide, peptide mimetic or phosphopeptide may be prepared and purified by means of genetic engineering methods or synthetic approaches known to those skilled in the art and described in the literature (e.g., Sambrook et al., 2001; Stewart and Young, Solid Phase Peptide Synthesis, Pierce Chemical Co., Rockford, Ill., 1984; E. Atherton and R. C. Sheppard, Solid Phase Peptide Synthesis. A Practical Approach, Oxford-IRL Press, New York, 1989). For example, targeted mutagenesis using PCR, chemical mutagenesis or bacterial mutator strains may be used to generate the modified polypeptides. In aspects, the polypeptides may be produced in a prokaryotic host or eukaryotic or cell-free systems. After insertion of a DNA sequence encoding the polypeptides into a suitable expression vector and transformation, transfection or infection of appropriate organisms the polypeptide is synthesized by the transcription/translation system. Alternatively, the gene expression can be achieved without utilizing a cell system. Another way of preparing a modified polypeptide is the synthesis in solution or on a solid support and subsequent isolation and purification. Genetic engineering and synthetic methods may also be combined in any way.

A modified polypeptide may be further modified by targeted and/or random modifications to enhance their affinity, specificity stability, solubility and production level in host cells. In an aspect, the polypeptides may have unmodified side-chains or carry at least one chemical modification at one or more side chains.

The disclosure also provides fusion proteins of polypeptides disclosed herein. Additional amino acids or peptides or substitutions of individual amino acids or peptides may be introduced (in particular at the amino and/or carboxy termini) to obtain fusion proteins by chemical coupling with suitable reagents. Fusion polypeptides may also be prepared by genetic engineering by linking the gene of the polypeptide to that of the fusion partner. Bivalent or bispecific polypeptides may be obtained by linking (for example, via an additionally introduced cysteine or positively or negatively charged amino acids at the carboxy terminal ends of the fusion partners) a polypeptide to a polypeptide of the same or a different specificity in a site-specific and covalent manner. For example, modified polypeptides disclosed herein may be coupled to (reporter) enzymes, toxins or other binding proteins, for example, biotin, digoxigenin, GFP, Flag, fluorescent luminescent substances, His, and/or HaloTag (see, B. N. Giepmans, et al The fluorescent toolbox for assessing protein location and function, Science, 312 (2006), pp. 217-224; K. Terpe, Overview of tag protein fusions: from molecular and biochemical fundamentals to commercial systems, Appl Microbiol Biotechnol, 60 (2003), pp. 523-533; D. S. Waugh, Making the most of affinity tags, Trends Biotechnol, 23 (2005), pp. 316-320; C. G. England, H. Luo, W. Cai, HaloTag technology: a versatile platform for biomedical applications; Bioconjug Chem, 26 (2015), pp. 975-986). In another aspect, the disclosure provides a polynucleotide encoding a CIP2A-TOPBP1 Inhibitor or BRCT7/8 Agent. In an embodiment, the polynucleotide is DNA. In another embodiment, the polynucleotide is RNA. Also provided are vectors containing such polynucleotides, including prokaryotic vectors, viral vectors, or eukaryotic vectors, such as mammalian vectors. Isolated cells or cell lines are also contemplated comprising a CIP2A-TOPBP1 Inhibitor or BRCT7/8 Agent. Cells or cell lines may comprise one or more transcribed and/or translated exogenous sequences that have been stably or transiently introduced into the cells. Examples of cells include bacterial cells such as E. coli cells, insect cells, yeast cells, or mammalian cells.

The present disclosure also features a method of producing a modified polypeptide, peptide or mimetic by culturing the cells in a medium under conditions permitting expression of a polypeptide encoded by the polynucleotide, and purifying the polypeptide from the cultured cell or the medium of the cell.

In aspects of the disclosure, transgenic organisms are provided carrying one or more sequences encoding CIP2A-TOPBP1 Inhibitor polypeptides, peptides or mimetics, BRCT7/8 Agents, and/or one or more exogenous sequences (e.g., sequences inserted via targeted integration). For example, transgenic organisms are contemplated comprising polynucleotides encoding the polypeptides and peptides under the control of an inducible promoter.

Screening

CIP2A-TOPBP1 Inhibitors also include agents identified by screening assays or methods. In aspects, a screening assay or method is provided for identifying agents that disrupt the interaction of CIP2A and TOPBP1 or disrupt the CIP2A-TOPBP1 complex. Detecting a negative effect of a candidate agent on the interaction or CIP2A-TOPBP1 complex activity, function or expression as compared with a control indicates a potential CIP2A-TOPBP1 Inhibitor. A screening assay may be carried out in vitro or in vivo.

An aspect of the disclosure provides a method to screen for an inhibitor of the interaction of CIP2A and TOPBP1 comprising: (1) providing a mixture comprising TOPBP1 and CIP2A; (2) contacting the mixture with a candidate agent; (3) determining the binding or interaction of TOPBP1 to CIP2A; wherein a statistically significant reduction in the binding or interaction of TOPBP1 to CIP2A in the presence of the candidate agent compared to those in the absence of the candidate agent is indicative that the test compound is an inhibitor of the interaction of CIP2A and TOPBP1.

In an embodiment, an assay is provided for measuring the level of binding between TOPBP1 with CIP2A or the level of CIP2A-TOPBP1 complex. In this embodiment, either the TOPBP1 or the CIP2A may be immobilized on a solid support, such as a 96-well plate coated by CIP2A or TOPBP1 (for example, by binding to an antibody against CIP2A or TOPBP1). The binding or interaction of TOPBP1 or CIP2A to the immobilized binding partner, in the presence or absence of a candidate agent may be measured and compared. A decrease in binding is indicative that the agent is a CIP2A-TOPBP1inhibitor.

Routine methods known to persons skilled in the art can be used to assay the interaction of CIP2A1 and TOPBP1 in a sample. For example, CIP2A-TOPBP1 complexes may be isolated using limited proteolysis, co-immunoprecipitation, Bimolecular Fluorescence Complementation (BiFC), Fluorescence Resonance Energy Transfer (FRET), Radio-immunoassay, ELISA, yeast two-hybrid (see Example), and Protein-fragment Complementation Assay (PCA), Affinity Electrophoresis or Gel-mobility shift assay, affinity chromatography, pull-down assay, co-immunoprecipitation, phage display, chemical crosslinking, tandem affinity purification (TAP), Microscale Thermophoresis (MST), Surface Plasmon Resonance (SPR), Fluorescence Anisotropy, Isothermal Titration calorimetry (ITC), Mass Spectrometry, X-ray crystallography, Nuclear Magnetic Resonance (NMR), Electron Microscopy and Protein Docking, and Proximity ligation assays.

In aspects, a LacR/LacO assay may be used to assess the interaction (see FIG. 4B and the Example for details for performing this assay).

In other aspects, a yeast two-hybrid system may be used to assess the protein interaction in vivo. Two-hybrid systems are described, for example, in Jer-Sheng Lin, Erh-Min Lai, Methods Mol Biol. 2017; 1615:177-187, doi: 10.1007/978-1-4939-7033-9_14; Edgar Rodriguez-Negrete et al., Methods Mol Biol. 2014; 1072:241-58 doi: 10.1007/978-1-62703-631-3_18 and publications referenced therein, and the Example below.

It will be appreciated that fusion proteins and recombinant fusion proteins may be used in the screening methods. It will also be appreciated that the CIP2A-TOPBP1 complex may be reconstituted in vitro using recombinant molecules and the effect of a candidate agent may be evaluated in the reconstituted system.

The disclosure also provides a method for identifying a CIP2A-TOPBP1 Inhibitor by evaluating a candidate agent's ability to effect CIP2A-TOPBP1 filaments in HR mutant cells, in particular, BRCA mutant cells. In an aspect, the disclosure provides a method for identifying or evaluating a candidate agent for its ability to decrease or reduce CIP2A-TOPBP1 filaments in a cell, in particular a BRCA mutant cell, comprising (i) assaying in a sample CIP2A-TOPBP1 filaments in the cell in the presence or absence of the agent, and (ii) detecting an increase or decrease in CIP2A-TOPBP1 filaments in the sample compared to a control as an indication of the ability of the agent to inhibit CIP2A-TOPBP1 complexes or complex formation.

A candidate agent used in the screening assays or methods can be any product in isolated form or in a mixture. The candidate agent may be defined by structure or function or it may be undefined. Examples of undefined candidate agents include without limitation tissue samples, biological fluids, cell supernatants, vegetal preparations; etc. Candidate agents may be peptides such as soluble peptides including Ig-tailed fusion peptides, members of random peptide libraries and combinatorial chemistry-derived molecular libraries made of D- and/or L-configuration amino acids, carbohydrates, nucleic acids, antisense molecules, phosphopeptides (including members of random or partially degenerate, directed phosphopeptide libraries), antibodies [e.g. polyclonal, monoclonal, humanized, anti-idiotypic, chimeric, single chain antibodies, fragments, (e.g. Fab, F(ab)$_2$, and Fab expression library fragments, and epitope-binding fragments thereof)], small organic or inorganic molecules, or libraries of compounds. A candidate agent may be an endogenous physiological compound or natural or synthetic compounds.

The methods for identifying CIP2A-TOPBP1 Inhibitors may comprise contacting more than one candidate agent, in parallel. In some aspects, the methods comprise contacting 2, 3, 4, 5, 6, 7, 8, 9, 10, 15, 20, 25, 30, 40, 50, 100, 1000, at least 2, at least 5, at least 10, at least 50, at least 100, or at least 1000 candidate agents in parallel. In some embodiments, high throughput screening of compounds and complete combinatorial libraries are assayed. Methods for performing high throughput screens are well known in the art. The methods can also be automated such that a robot can perform the experiments.

Screening methods may further comprise conducting therapeutic profiling of the identified agents or further analogs thereof, for efficacy and toxicity in animals; optionally formulating a pharmaceutical composition including one or more agents identified as having an acceptable therapeutic profile; and optionally administering the agent to a subject or individual.

A method of the disclosure for screening for a CIP2A-TOPBP1 inhibitor may further comprise administering the CIP2A-TOPBP1 to an individual or subject.

The disclosure also provides a CIP2A-TOPBP1 Inhibitor comprising a modified polypeptide or agent that interacts with or binds CIP2A or TOPBP1 linked to a moiety that recruits the cellular enzyme E3 ubiquitin ligase [i.e., a proteolysis-targeting chimaera (PROTAC)]. Recruitment of the E3 ligase leads to ubiquitination and subsequent proteasome mediated-degradation of the target protein (i.e., CIP2A or TOPBP1). In an aspect, a CIP2A-TOPBP1 Inhibitor is provided comprising a modified polypeptide of the disclosure or agent identified using a method described herein that disrupts the interaction of CIP2A and TOPBP1 by a moiety that binds CIP2A or TOPBP1 which polypeptide or agent is linked to a moiety that recruits an E3 ligase. In an aspect, the CIP2A-TOPBP1 Inhibitor is a PROTAC comprising one moiety that binds to CIP2A linked to a moiety that recruits E3 ubiquitin ligase. In an embodiment, the moiety that binds to CIP2A comprises amino acids 756 to 1000, 776-851, 756-891, or 830 to 851 of SEQ ID NO. 11 or a sequence substantially homologous thereto, or fragments thereof. In an aspect the CIP2A-TOPBP1 Inhibitor is a PROTAC comprising one moiety that binds to TOPBP1 linked to a moiety that recruits E3 ubiquitin ligase. In an embodiment, the moiety that binds to TOPB1 comprises amino acids 1-560 of SEQ ID NO. 10 or a sequence substantially homologous thereto, or fragments thereof. Examples of moieties that recruit the cellular enzyme E3 ubiquitin ligase include without limitation, cereblon (CRBN) E3 ligase binding moiety (thalidomide derivatives such as pomalidomide and lenalidomide) or von Hippel-Landau (VHL) E3 ligase binding moiety (such as HIF-1α-derived (R)-hydroxyproline containing VHL E3 ligase ligands). [See Xin-Zhou et al, PROTAC: A promising technology for cancer treatment. European Journal of Medicinal Chemistry, 203 (1) October 2020, 112539; Xin Li and Yongcheng Song; Proteolysis-targeting chimera (PROTAC) for targeted protein degradation and cancer therapy. Journal of Hematology & Oncology; Yang Wang et al, Degradation of proteins by PROTACs and other strategies. Acta Pharmaceutica Sinica B, 10(2), February 2020, Pages 207-238.]

It is also contemplated that targeted reduction of CIP2A and TOPBP1 and thus the CIP2A-TOPBP1 complex may be accomplished at the transcription level using nucleic acid-based methods [Lundin K E, et al., Oligonucleotide therapies: the past and the present. Hum Gene Ther. 2015; 26(8):475-85. 2], including RNA interference (RNAi) [Wittrup A, Lieberman J. Knocking down disease: a progress report on siRNA therapeutics. Nat Rev Genet. 2015; 16(9):543-52. 3] and CRISPR/Cas9-mediated gene knockout technology [Fellmann C, Gowen B G, Lin P-C, Doudna J A, Corn J E. Cornerstones of CRISPR-Cas in drug discovery and therapy. Nat Rev Drug Discov. 2017; 16(2): 89-100. 4].

The disclosure further provides a kit for performing an assay or method disclosed herein, and a kit comprising at least one effective dose of a CIP2A-TOPBP1 Inhibitor as described herein.

BRCT7/8 Agents include agents identified using assays contemplated herein and those known in the art (Leung C C, et al., J Biol Chem. 2011 Feb. 11; 286(6):4292-301. Doi 10.1074/jbc.M110.189555).

Compositions

The disclosure provides a pharmaceutical composition comprising an effective amount of a CIP2A-TOPBP1 Inhibitor or BRCT7/8 Agent for use in treating an HR Deficient Cancer. In an aspect a pharmaceutical composition is provided for inhibiting, reducing or suppressing the growth or survival of cancer cells with HR deficiencies comprising administering an effective amount of a CIP2A-TOPBP1 Inhibitor or a BRCT7/8 Agent. In another aspect, a pharmaceutical composition of the disclosure is administered to cancer cells with HR deficiencies. In an embodiment, a pharmaceutical composition of the disclosure is administered to HR mutant cells, in particular BRCA mutant cells.

A pharmaceutical composition may optionally comprise a pharmaceutically acceptable carrier. In an embodiment, the disclosure provides a pharmaceutical composition for the treatment of an HR Deficient Cancer characterized in that it comprises an effective amount of a CIP2A-TOPBP1 Inhibitor or a BRCT7/8 Agent together with a pharmaceutically acceptable carrier.

A composition of the disclosure may comprise one or more additional component or it may be administered in combination with another treatment, in particular a component or procedure for treating an HR Deficient Cancer, including but not limited to a chemotherapeutic agent, a non-steroidal anti-inflammatory drug, vaccines with autologous tumor cells, vaccines against tumor-associated antigens, monoclonal antibodies against tumor antigens, gene therapy including gene correction, virus-directed enzyme prodrug treatment, or a treatment such as radiation therapy or surgery.

A pharmaceutical composition of the disclosure may comprise a therapeutically effective amount of a CIP2A-TOPBP1 Inhibitor or a BRCT7/8 Agent and a chemotherapeutic agent. In an aspect the disclosure provides a pharmaceutical composition comprising therapeutically effective amounts of a CIP2A-TOPBP1 Inhibitor or a BRCT7/8 Agent and a chemotherapeutic agent that provide beneficial effects relative to the chemotherapeutic agent alone. The beneficial effects may include reduced toxicity and/or increased antineoplastic activity. In an aspect, the disclosure provides a pharmaceutical formulation comprising a CIP2A-TOPBP1 Inhibitor or a BRCT7/8 Agent, and a chemotherapeutic agent formulated in a pharmaceutically acceptable excipient and suitable for use in humans to treat a HR Deficient Cancer.

The disclosure also contemplates a pharmaceutical composition in separate containers and intended for simultaneous or sequential administration to prevent or treat a HR Deficient Cancer comprising a CIP2A-TOPBP1 Inhibitor or a BRCT7/8 Agent, and a chemotherapeutic agent both optionally together with pharmaceutically acceptable carriers.

In aspects of the compositions of the disclosure the chemotherapeutic agent is a platinum drug. In embodiments, the platinum drug is cisplatin, oxaliplatin, carboplatin, nedaplatin, straplatin, picoplatin, phenanthriplatin or triplatin tetranitrate, preferably cisplatin.

In other aspects, the chemotherapeutic agent is a PARP Inhibitor. In embodiments, the PARP inhibitor is an agent that targets PARP1 and/or PARP2. In embodiments, the PAR Inhibitor is veliparib, rucaparib, niraparib, olaparib, iniparib, talazoparib, JPI-289, CEP-9722, GPI 2016, and INO-1001, or other known PARP inhibitors.

In other aspects, the chemotherapeutic agent is an ATR Inhibitor. In embodiments, the ATR Inhibitor is Schisandrin B, NU6027, NVP-BEZ235, torin 2, ETP-46464, VE-821, VE-822, AZ20, RP-3500, ART0380, BAY1895344, M4344 or AZD6738, or other known ATR inhibitors.

A composition herein is formulated in accordance with routine procedures as a pharmaceutical composition adapted for administration to human subjects.

Treatment

A method for inhibiting, reducing or suppressing the growth or survival of cancer cells with HR deficiencies is provided comprising contacting the cells with an effective amount of a CIP2A-TOPBP1 Inhibitor or a BRCT7/8 Agent, or composition of the disclosure. In an aspect, a method is provided for inhibiting, reducing or suppressing the growth or survival of HR mutant cells, in particular BRCA mutant cells, comprising contacting the cells with an effective amount of a CIP2A-TOPBP1 Inhibitor, a BRCT7/8 Agent, or composition of the disclosure.

The disclosure provides a method of treating a subject on PARP Inhibitor therapy whose cancer or tumor progresses comprising administering to the subject a CIP2A-TOPBP1 Inhibitor or a composition comprising the CIP2A-TOPBP1 Inhibitor. The disclosure also provides a method of treating a subject whose cancer or tumor progresses on PARP Inhibitor therapy comprising administering to the subject a CIP2A-TOPBP1 Inhibitor or a composition comprising the CIP2A-TOPBP1 Inhibitor.

A method is provided for treating a HR Deficient Cancer in an individual comprising administering to the individual an effective amount of a CIP2A-TOPBP1 Inhibitor, a BRCT7/8 Agent, or composition of the disclosure. The disclosure provides methods for treating cancer cells with HR deficiencies in an individual in need of such treatment comprising administering to the individual an effective amount of a CIP2A-TOPBP1 Inhibitor, a BRCT7/8 Agent, or composition of the disclosure. The disclosure also provides a method for treating an individual having a HR Deficient Cancer or suspected of having a HR Deficient Cancer comprising administering to the individual a CIP2A-TOPBP1 Inhibitor or a composition comprising the CIP2A-TOPBP1 Inhibitor, or a BRCT7/8 Agent or a composition comprising the BRCT7/8 Agent.

The disclosure also provides a method of inducing apoptosis in cancer cells with HR Deficiencies, in particular HR mutant cells, in particular, BRCA mutant cells, comprising contacting the cells with a CIP2A-TOPBP1 Inhibitor, a BRCT7/8 Agent, or composition of the disclosure. In this embodiment, a CIP2A-TOPBP1 Inhibitor, a BRCT7/8 Agent, or composition of the disclosure is administered to cancer cells with HR deficiencies, in particular HR mutant cells, in particular BRCA mutant cells, to thereby promote apoptosis.

The disclosure provides a method for treating cancer cells with HR deficiencies, in particular HR mutant cells, in particular BRCA mutant cells, in an individual comprising administering to the individual effective amounts of a CIP2A-TOPBP1 Inhibitor or a composition of the disclosure, and monitoring the response to, or efficacy of the CIP2A-TOPBP1 Inhibitor or composition, using CIP2A, TOPBP1, BRCA1 and/or BRCA2 as biomarkers of drug response.

A treatment method of the disclosure may comprise one or more additional component or treatment, in particular a component or procedure for treating or preventing a HR Deficient Cancer. Thus, the disclosure provides a combination treatment for a HR Deficient Cancer comprising administering to an individual in need thereof an effective amount of an CIP2A-TOPBP1 Inhibitor, a BRCT7/8 Agent, or composition of the disclosure, and one or more additional component or treatment. In an aspect, the disclosure provides methods for treating cancer cells with HR deficiencies in an individual in need of such treatment comprising administering to the patient an effective amount of an CIP2A-TOPBP1 Inhibitor, a BRCT7/8 Agent, or composition of the disclosure, and one or more other component or treatment chosen or selected from the group consisting of a chemotherapeutic agent, a non-steroidal anti-inflammatory drug, immunotherapies such as vaccination with autologous tumor cells, vaccination against tumor-associated antigens, monoclonal antibodies against tumor antigens, gene therapy including gene correction, virus-directed enzyme prodrug treatment, matrix metalloproteinase inhibitors, radiation therapy or surgery. In an aspect, the additional component or treatment is a chemotherapeutic agent, in particular a platinum anti-cancer drug, PARP Inhibitor, or ATR Inhibitor.

In an aspect, the disclosure provides a method for the prevention and/or intervention of a HR Deficient Cancer in an individual comprising administration of at least one CIP2A-TOPBP1 Inhibitor or a composition of the disclosure and at least one PARP Inhibitor. In embodiments, the PARP inhibitor is an agent that targets PARP1 and/or PARP2. In embodiments, the PAR Inhibitor is veliparib, rucaparib, niraparib, olaparib, iniparib, talazoparib, JPI-289, CEP-9722, GPI 2016, and INO-1001, or other known PARP inhibitors.

In an aspect, the disclosure provides a method for the prevention and/or intervention of a HR Deficient Cancer in an individual comprising administration of at least one CIP2A-TOPBP1 Inhibitor, a BRCT7/8 Agent, or a composition of the disclosure and at least one platinum drug. In embodiments, the platinum drug is cisplatin, oxaliplatin, carboplatin, nedaplatin, straplatin, picoplatin, phenanthriplatin or triplatin tetranitrate, preferably cisplatin.

In an aspect, the disclosure provides a method for the prevention and/or intervention of a HR Deficient Cancer in an individual comprising administration of at least one CIP2A-TOPBP1 Inhibitor or a composition of the disclosure and at least one ATR Inhibitor. In embodiments, the ATR inhibitor is Schisandrin B, NU6027, NVP-BEZ235, torin 2, ETP-46464, VE-821, VE-822, AZ20, RP-3500, ART0380, BAY1895344, M4344 and AZD6738, or other known ATR inhibitor(s).

A method is provided for delivering an effective amount of a CIP2A-TOPBP1 Inhibitor or a BRCT7/8 Agent, to an individual with cancer cells with HR deficiencies that increases the sensitivity of the cancer cells to chemotherapy comprising combining a CIP2A-TOPBP1 Inhibitor or a BRCT7/8 Agent, with the chemotherapy and administering the combination to the individual. In embodiments, the chemotherapy is a platinum drug, in particular cisplatin. In an aspect, a method is provided for delivering an effective amount of a CIP2A-TOPBP1 Inhibitor to an individual with cancer cells with HR deficiencies that increases the sensitivity of the cancer cells to a PARP Inhibitor, comprising combining the CIP2A-TOPBP1 Inhibitor with the PARP Inhibitor and administering the combination to the individual. In embodiments, the PARP inhibitor is an agent that targets PARP1 and/or PARP2. In embodiments, the PAR Inhibitor is veliparib, rucaparib, niraparib, olaparib, iniparib, talazoparib, JPI-289, CEP-9722, GPI 2016, and INO-1001, or other known PARP inhibitors. In an aspect, a method is provided for delivering an effective amount of a CIP2A-TOPBP1 Inhibitor to an individual with cancer cells with HR deficiencies that increases the sensitivity of the cancer cells to a ATR Inhibitor, comprising combining the CIP2A-TOPBP1 Inhibitor with the ATR Inhibitor and administering the combination to the individual. In embodiments, the ATR Inhibitor is Schisandrin B, NU6027, NVP-BEZ235, torin 2, ETP-46464, VE-821, VE-822, AZ20, RP-3500, ART0380, BAY1895344, M4344 and AZD6738, or other known ATR inhibitor(s).

In an aspect, a method is provided for reducing dosage levels of a PARP Inhibitor, platinum drug or ATR Inhibitor for administration to an individual with a HR Deficient Cancer which comprises administering a combination of at least one CIP2A-TOPBP1 Inhibitor with the PARP Inhibitor, platinum drug or ATR Inhibitor. In a particular aspect, the disclosure provides a method of substantially reducing dosage levels of a PARP Inhibitor for administration to an individual with a HR Deficient Cancer comprising administering a combination of one or more daily doses of at least one CIP2A-TOPBP1 Inhibitor with one or more daily doses of the PARP Inhibitor.

A method is also provided for increasing the response to a PARP Inhibitor for treating a HR Deficient Cancer in an individual who is a poor responder to the PARP Inhibitor, which comprises administering to the individual a therapeutically effective amount of a CIP2A-TOPBP1 Inhibitor or composition of the disclosure. In an aspect the disclosure provides a method of increasing response to a PARP Inhibitor in an individual with a HR Deficient Cancer who is a poor responder to the PARP Inhibitor, which comprises administering a CIP2A-TOPBP1 Inhibitor in combination with the PARP Inhibitor. In a particular aspect the disclosure provides a method of increasing response to a PAPR Inhibitor in an individual with a HR Deficient Cancer who is a poor responder to the PARP Inhibitor, which comprises administering a combination of one or more daily doses of at least one PARP Inhibitor in combination with one or more daily doses of at least one CIP2A-TOPBP1 Inhibitor.

A method is also provided for increasing the response to an ATR Inhibitor for treating a HR Deficient Cancer in an individual who is a poor responder to the ATR Inhibitor, which comprises administering to the individual a therapeutically effective amount of a CIP2A-TOPBP1 Inhibitor or composition of the disclosure. In an aspect the disclosure provides a method of increasing response to an ATR Inhibitor in an individual with a HR Deficient Cancer who is a poor responder to the ATR Inhibitor, which comprises administering a CIP2A-TOPBP1 Inhibitor in combination with the ATR Inhibitor. In a particular aspect the disclosure provides a method of increasing response to an ATR Inhibitor in an individual with a HR Deficient Cancer who is a poor responder to the ATR Inhibitor, which comprises administering a combination of one or more daily doses of at least one ATR Inhibitor in combination with one or more daily doses of at least one CIP2A-TOPBP1 Inhibitor.

In an embodiment, the disclosure provides a method of promoting treatment of patients having a HR Deficient Cancer comprising packaging, labelling and/or marketing a CIP2A-TOPBP1 Inhibitor or a BRCT7/8 Agent alone, or in combination with an anti-cancer drug, to be used in treating an individual having a HR Deficient Cancer. In an aspect, the disclosure provides a method of promoting treatment of an individual having cancer cells with HR deficiencies comprising packaging, labelling and/or marketing a CIP2A-TOPBP1 Inhibitor to be used in conjoint therapy with a PARP Inhibitor, a platinum drug or ATR Inhibitor for treating the individual.

The disclosure contemplates the use of a composition comprising a CIP2A-TOPBP1 Inhibitor or BRCT7/8 Agent for treating cancer cells with HR deficiencies, in particular HR mutant cells, more particularly BRCA mutant cells, or in the preparation of one or more medicament for treating cancer cells with HR deficiencies. In another aspect, the disclosure relates to the use of a composition comprising a CIP2A-TOPBP1 Inhibitor or BRCT7/8 Agent for the preparation of a medicament which has a protracted profile of action in treating cancer cells with HR deficiencies. The disclosure contemplates the use of a composition comprising a CIP2A-TOPBP1 Inhibitor or BRCT7/8 Agent in the preparation of one or more medicament for treating a HR Deficient Cancer.

The disclosure also contemplates the use of a composition comprising a combination of at least one a CIP2A-TOPBP1 Inhibitor and at least one additional treatment, in particular a chemotherapeutic agent, more particularly a PARP Inhibitor, ATR Inhibitor or platinum drug, for the preparation of one or more medicament for treating cancer cells with HR deficiencies or treating a HR Deficient Cancer. The disclosure further contemplates use of a CIP2A-TOPBP1 Inhibitor in combination with at least one additional treatment, in particular a chemotherapeutic agent, more particularly a PARP Inhibitor or platinum compound, for the manufacture of a medicament for the treatment of a HR Deficient Cancer. Still further the disclosure provides use of a CIP2A-TOPBP1 Inhibitor for the manufacture of a medicament for the treatment of a HR Deficient Cancer used in combination with at least one additional treatment, in particular a chemotherapeutic agent, more particularly a PARP Inhibitor, ATR Inhibitor or platinum compound.

In an aspect, the disclosure relates to the use of synergistically effective amounts of at least one CIP2A-TOPBP1 Inhibitor and at least one additional treatment, in particular a chemotherapeutic agent, more particularly a PARP Inhibitor, ATR Inhibitor or platinum compound, for the preparation of a medicament for preventing or treating cancer cells with HR deficiencies or treating a HR Deficient Cancer. In another aspect, the disclosure relates to the use of a CIP2A-TOPBP1 Inhibitor and at least one additional treatment, in particular a chemotherapeutic agent, more particularly a PARP Inhibitor, ATR Inhibitor or a platinum compound, for the preparation of a medicament which has a protracted profile of action. The disclosure additionally provides uses of a pharmaceutical composition of the disclosure in the preparation of medicaments for the prevention and/or treatment of cancer cells with HR deficiencies or a HR Deficient Cancer.

The disclosure further relates to the use of one or more daily doses of a CIP2A-TOPBP1 Inhibitor in combination with one or more daily doses of a chemotherapeutic agent, in particular a PARP Inhibitor, ATR Inhibitor or platinum drug, for treating a HR Deficient Cancer in an individual wherein the amount of chemotherapeutic agent, in particular PARP Inhibitor or platinum drug, is substantially reduced as compared with the use of the chemotherapeutic agent, in particular PARP Inhibitor, ATR Inhibitor or platinum drug, on its own.

The disclosure further provides for the use of one or more daily doses of a CIP2A-TOPBP1 Inhibitor compound in combination with one or more daily doses of a chemotherapeutic agent, in particular a PARP Inhibitor, ATR Inhibitor or platinum drug, for treating an individual who is a poor responder to the chemotherapeutic agent, in particular PARP Inhibitor, ATR Inhibitor or platinum drug.

Since the present disclosure relates to a method of treatment involving compositions comprising a CIP2A-TOPBP1 Inhibitor or BRCT7/8 Agent, the disclosure also provides a kit comprising a composition of the disclosure in kit form. In an aspect, the disclosure provides a method for treating an individual in need of treatment with a CIP2A-TOPPB1 Inhibitor comprising (a) requesting a test providing the results of an analysis to determine if the individual is sensitive to the CIP2A-TOPBP1 Inhibitor by detecting CIP2A-TOPBP1 complexes or filaments in HR mutant cells, in particular BRCA mutant cells, in a sample from the individual and comparing to a control to determine if the individual is sensitive to the CIP2A-TOPBP1 Inhibitor; and (b) administering the CIP2A-TOPBP1 inhibitor to the individual if the individual is sensitive to the CIP2A-TOPBP1 Inhibitor.

In an aspect of the treatment methods of the invention, the individual has breast cancer. In an aspect of the treatment methods of the invention, the individual has ovarian cancer.

The following non-limiting example is illustrative of the present invention:

Example 1

The following materials and methods were used in the study described in this Example.

Cell Culture

RPE1-hTERT, U2OS and 293T cells were grown at 37° C. and 5% $CO_2$ in DMEM supplemented with 10% FBS (Wisent #080150) and 1% Pen/Strep (Wisent). Parental and $BRCA2^{-/-}$ DLD1 cells were purchased from Horizon and maintained in RPMI-1640 medium (ATCC 30-2001) supplemented with 10% FBS and 1% Pen/Strep. Parental and $BRCA2^{-/-}$ DLD1 Cas9 cells were generated through viral infection with lentiCas9-Blast (Addgene #52962) followed by blasticidin selection. MDA-MB-436 cells were purchased from ATCC and maintained in DMEM supplemented with 10% FBS and 1% Pen/Strep. DLD1 and MDA-MB-436 cell lines were grown at 37° C. in a low-oxygen (3% $O_2$) incubator. The RPE1-hTERT $p53^{-/-}$ $BRCA1^{-/-}$, $BRCA1^{-/-}$ 53 $BP1^{-/-}$, $APEX2^{-/-}$, $CIP2A^{-/-}$ and the U2OS $MDC1^{-/-}$ knockout cell lines were described previously [Alvarez-Quilon, A. et al. *Mol Cell* 78, 1152-1165 e1158, doi:10.1016/j.molcel.2020.05.021 (2020); Hustedt, N. et al. *Open Biol* 9, 190156, doi:10.1098/rsob.190156 (2019); Leimbacher, P. A. et al. *Mol Cell* 74, 571-583 e578, doi:10.1016/j.molcel.2019.02.014 (2019). Noordermeer, S. M. et al. *Nature* 560, 117-121, doi:10.1038/s41586-018-0340-7 (2018)] The $CIP2A^{-/-}$ RPE1-hTERT cell line (i.e. $p53^+$) is described in de Marco Zompit et al. (bioRxiv, 2021, 2002.008.430274, doi:10.1101/2021.02.08.430274 (2021)). The DLD1 $CIP2A^{-/-}$ cell lines were generated by Cas9 RNP transfection with sgCIP2A-2 using Lipofectamine CRISPRmax (Invitrogen), followed by single clone isolation. Cell lines were validated by TIDE/ICE analysis and by immunoblot. 293T (ATCC CRL-3216) and parental U2OS cells (ATCC HTB-96) were also used in this study. Cell lines were routinely monitored to ensure absence of *mycoplasma* contamination; none of the cell lines are listed in the ICLAC database and parental cell lines have been authenticated by STR analysis.

Lentiviral Transduction

Lentiviral particles were produced in 293T cells in 10-cm plates by co-transfection of 10 µg of targeting vector with 3 µg VSV-G, 5 µg pMDLg/RRE and 2.5 µg pRSV-REV (Addgene #14888, #12251, #12253) using calcium phosphate. Viral transductions were performed in the presence of 4 µg/µL polybrene (Sigma-Aldrich) at a multiplicity of infection (MOI)<1. Transduced cells were selected by culturing in the presence of blasticidin (InvivoGen) or nourseothricin (Jena Bioscience) depending on the lentiviral vector used.

Two-Color Competitive Growth Assays

Cells were transduced with sgRNA expression lentiviruses, either expressing NLS-mCherry-sgAAVS1 (control) or an NLS-GFP-sgRNA targeting a specific gene of interest at an MOI of ~0.5. 24 h after transduction, cells were selected for 48 h using 15 µg/mL (RPE1) or 2 µg/mL (DLD1) puromycin (Life Technologies). 96 h after transduction, mCherry- and GFP-expressing cells were mixed 1:1 (2,000 cells each for RPE1; 3,000 cells each for RPE1 $BRCA1^{-/-}$ and DLD1; 9,000 cells each for DLD1 $BRCA2^{-/-}$) and seeded in a 12-well plate. Cells were imaged for GFP and mCherry 24 h after initial plating (t=0) and at the indicated timepoints using a 4× objective InCell Analyzer system (GE Healthcare Life Sciences, Marlborough). Segmentation and counting of GFP- and mCherry-positive cells were performed using an Acapella script (PerkinElmer, Waltham). Efficiency of indel formation was analysed by performing PCR amplification of the region surrounding the sgRNA sequence using DNA isolated from cells collected from 4 to 7 days after transduction and subsequent ICE analysis (https://ice.synthego.com/#/).

Clonogenic Survival Assays

Cells were transduced at low MOI (<1.0) with lentivirus derived from pLentiGuide (RPE1 cells) or pLentiCRISPRv2, which expressed sgRNAs targeting CIP2A, TOPBP1 or AAVS1 (which was used as control). Puromycin-containing medium was added the next day to select for transductants and cells were seeded for clonal growth 48 h later. Cells were seeded in 10-cm dishes (750-5,000 cells per 10 cm plate, depending on cell line and genotype). For drug sensitivity assays, cells were seeded into media containing a range of camptothecin (Sigma) concentrations (for determination of camptothecin sensitivity) or in regular media after several days of AS1 treatment (i.e., after induction of B6L). For clonogenic survival assays performed with $CIP2A^{-/-}$ cells, plates were incubated in atmospheric oxygen. Experiments performed with $BRCA1^{-/-}$ and $BRCA2^{-/-}$ cells and their controls were incubated at 3% $O_2$. Medium was refreshed after 7 d. After 14-20 d, colonies were stained with a crystal violet solution (0.4% (w/v) crystal violet (Sigma), 20% methanol). Colonies were manually counted or counted using a GelCount instrument (Oxford Optronix). Data were plotted as surviving fractions relative to untreated cells or sgAAVS1-transduced controls.

Plasmids

For CRISPR-Cas9 genome editing, sgRNAs were cloned either in lentiCRISPRv2 or in lentiguide-NLS-GFP as in Alvarez-Quilon, A. et al. (Mol Cell 78, 1152-1165 e1158, doi:10.1016/j.molcel.2020.05.021 (2020)). The pcDNA5-FRT/TO-LacR-FLAG-TOPBP1 plasmid was obtained from Addgene (#31313). Point mutants were introduced by site-directed mutagenesis using Quikchange (Agilent). For TOPBP1 rescue experiments, the pLenti-CMVie-IRES-BlastR (pCIB) plasmid was obtained from Addgene (#119863). pCIB-2×HA was generated by cloning a double HA tag with a flanking NotI site in pCIB, using AscI and BamHI restriction sites. The TOPBP1 coding sequence was amplified from pcDNA5-FRT/TO-LacR-FLAG-TopBP1 and mutagenised at Genscript (Piscataway, NJ) to generate an sgRNA-resistant construct with a silent mutation at Thr263 (ACC to ACA). This fragment was then cloned into pCIB-2×HA using NotI and BamHI restriction sites to generate pCIB-2×HA-TOPBP1-sgR. For the inducible expression of the B6L fragment, a cassette was first synthesized coding the FKBP-derived destabilization domain (DD) [Banaszynski, L. A., et al., Cell 126, 995-1004, doi:10.1016/j.cell.2006.07.025 (2006)] along with an EcoRI restriction site and a single FLAG tag (Genscript). This cassette was then cloned into pHIV-NAT-T2A-hCD52 (gift of R. Scully) using the NotI and BamHI restriction sites to generate pHIV-NAT-DD-FLAG. pHIV-NAT-DD-FLAG-B6L was amplified by PCR from pcDNA5-FRT/TO-LacR-FLAG-TOPBP1(756-1000) and cloned into pHIV-NAT-DD-FLAG. The CIP2A coding sequence was amplified from a BirA-CIP2A expression plasmid (gift from A.-C. Gingras) and cloned into the pcDNA5-FRT/TO-FLAG vector using the AscI and EcoRI sites. The mutation making this vector resistant to sgCIP2A-2 (silent mutation in Ala250, GCC to GCA) was introduced by site-directed mutagenesis generating pcDNA5-FRT/TO-Flag-CIP2A-sg2R. Using this vector as a template, FLAG-CIP2A or portions of CIP2A were amplified by PCR and cloned into the pHIV-NAT-T2A-hCD52 using NotI and EcoRI restriction sites. The corresponding control vector, pHIV-NAT-FLAG-T2A-hCD52, and pHIV-NAT-FLAG-CIP2A(560-915) were generated by deletion PCR from pHIV-NAT-FLAG-CIP2A-sg2R. For yeast two hybrid experiments, a fragment corresponding to CIP2A (1-560) was cloned by Genscript into pGADT7 AD (Clontech/Takara) to create a fusion with the GAL4 activating domain using EcoRI and XmaI restriction sites, whereas a TOPBP1 fragment corresponding to residues 2-1523 was amplified from pCDNA5-FRT/TO-LacR-FLAG-TopBP1 and cloned into pGBKT7 (Clontech/Takara) to create a fusion with the GAL4 DNA binding domain using the NdeI and XmaI sites. pGBKT7-GAL4-BD-TOPBP1-Δ756-891 and pGBKT7-GAL4-BD-TOPBP1-3A were derived from pGBKT7-GAL4-BD-TOPBP1, removing the sequence coding residues 756-891 by deletion PCR and mutating the codons for Phe837, Asp838, Val839 to Ala by Quikchange site-directed mutagenesis, respectively. pGBKT7-GAL4-BD-TOPBP1(830-851) was generated by cloning a TOPBP1 fragment corresponding to residues 830-851 into pGBKT7 using the NdeI and XmaI restriction sites. The alanine scanning library of the TOPBP1 830-851 fragment was generated at Genscript and cloned into pGBKT7-GAL4-BD. MBP-TOPBP1 plasmids were derived from pET-His-MBP-TEV-HTa and GST-CIP2A (1-560) was derived from pGEX4T1 (SigmaAldrich).

CRISPR Screens

The CRISPR screens were carried out using known protocols [Alvarez-Quilon, A. et al. (Mol Cell 78, 1152-1165 e1158, doi:10.1016/j.molcel.2020.05.021 (2020); Zimmermann, M. et al. Nature 559, 285-289, doi:10.1038/s41586-018-0291-z (2018); Hart, T. et al. Cell 163, 1515-1526, doi:10.1016/j.cell.2015.11.015 (2015)]. Synthetic lethality screens are basically undertaken as two parallel screens with a parental cell line and an isogenic variant with one genetic alteration, in this case BRCA1 or BRCA2 loss-of-function mutations. For the BRCA2 and CIP2A screens, DLD1 parental and BRCA2-/- cells, or RPE1-hTERT p53$^{-/-}$ Flag-Cas9 parental and CIP2A$^{-/-}$ cells were transduced with the lentiviral TKOv3 sgRNA library [Hart, T. et al. Cell 163, 1515-1526, doi:10.1016/j.cell.2015.11.015 (2015); Hart, T. et al. G3 (Bethesda) 7, 2719-2727, doi:10.1534/g3.117.041277 (2017)] at a low MOI (~0.3) and media containing puromycin (Life Technologies) was added the next day to select for transductants. The following day, cells were trypsinized and replated in the same plates while maintaining puromycin selection. 3 days after infection, which was considered the initial time point (t0), cells were pooled together and divided into 2 sets of technical replicates. Cells were grown for a period of 18-30 days and cell pellets were collected every 3 days. Each screen was performed as a technical duplicate with a theoretical library coverage of ≥400 cells per sgRNA maintained at every step. Genomic DNA was isolated using the QIAamp Blood Maxi Kit (Qiagen) and genome-integrated sgRNA sequences were amplified by PCR using NEBNext Ultra II Q5 Master Mix (New England Biolabs). i5 and i7 multiplexing barcodes were added in a second round of PCR and final gel-purified products were sequenced on an Illumina NextSeq500 system at the LTRI NBCC facility (https://nbcc.lunenfeld.ca/) to determine sgRNA representation in each sample. Screens were analyzed using BAGEL2 (Kim, E and Hart T, Genome Med 13, 2, doi 10.1186/s13073-020-00809-3 (2021)) and CRISPRCount Analysis (CCA) (see below).

CRISPRCount Analysis (CCA)

CCA is a scoring approach optimized for isogenic CRISPR screens that provides gene-level scores and ranking of genes according to the impact of their targeting sgRNAs between test and control samples. CCA also aims to prioritize sgRNAs that are selectively deleterious to fitness in the test samples. CCA is available on Docker. To download the Docker image of CCA, install Docker and then in a terminal window, execute: "docker pull tohsumirepare/cca". The CCA Docker image source is located at and the documentation for CCA, such the input file format and method of execution, is in the doc folder.

CCA employs non-parametric statistics. Implementation of CCA was based on MolBioLib [Ohsumi, T. K. & Borowsky, M. L., Bioinformatics 28, 2412-2416, doi: 10.1093/bioinformatics/bts458 (2012)] and includes the Mann-Whitney U test from ALGLIB C++. The input of CCA is a matrix of samples versus sgRNAs where the entries are the sgRNA readcounts in that sample. The CCA score is computed as follows: (1) normalization of the readcount file so that each sample's count over all sgRNAs is 10 million; (2) removal of sgRNAs with readcounts at T0 is <30 to avoid false positives due to low readcounts; (3) computing a depletion matrix of samples versus sgRNAs where the depletion=1−(count at final time)/(count at initial time)=1−foldchange. The depletion is such that it is maximum, 1, if the test sample has no viable cells at the final timepoint. The depletion may be negative if there is proliferation of cells at the final timepoint. By default, the minimum value of the depletion of all control samples is limited to 0 (doing otherwise can create false positive hits if sgRNAs cause proliferation in control samples).

For a given gene, the vector of depletion values over all test samples is denoted t and over all control samples is denoted c. For vector v, let Q3(v) be the third quantile of v. The CCA score for that gene is:

$$\text{Score} = \{A^* \text{median}(t) + B^* Q3(t) + C^*(\text{median}(t) - \text{median}(c)) + D^*(Q3(t) - Q3(c))\}^* \{1-(\text{likelihood } t<\text{non-essential})^E\}^* \{1-(\text{likelihood } c>\text{essential})^F\}^* \{1-(\text{likelihood } t=c)^G\}^* \{1-(\text{likelihood } t<c)^H\}$$

where $A \cong 2$, $B \cong 0.017$, $C \cong 0.02$, $D=1$, $E \cong 8.8$, $G \cong 7.1$, and $H \cong 0.22$. Likelihoods are computed using Mann-Whitney U test where the inequality is tested by taking either the right or left tail and the equality is tested by taking both tails. For comparison with essential and non-essential genes, the gene sets described in Hart, T. & Moffat, J., *BMC Bioinformatics* 17, 164, doi:10.1186/s12859-016-1015-8 (2016) were used. For essential genes, depletion values of all samples of all sgRNAs associated with an essential gene were used. For isogenic screens, 10,000 was subtracted from all genes whose median(t) is less than zero. The top 3000 CCA scores are modeled using a beta distribution fitted using the fitdistrplus package [Delignette-Muller, M. L. & Dutang., 2015 64, 34, doi:10.18637/jss.v064.i04 (2015)] in R. The top genes with p<0.05, were stratified into 4 Jenks classes using the classInt package in R. The values of the parameters, A through H except D, were determined by using a derivative-free optimization method, BiteOpt, to minimize:

$$Penalty = 1 / \left( \begin{array}{c} \frac{1}{4} * numInTop300 + numInTop200 + 2 * numInTop100 + \\ 4 * numInTop50 + 8 * numInTop25 + 16 * numInTop10 + \\ 32 * numInTop5 + 1 \end{array} \right)$$

where numInTopN is the number of positive control synthetic lethal genes found in the top N genes as ranked by CCA's scoring method over all training screens that have positive controls. D is always set to 1, as the other variables, A, B, and C, may be scaled. For the purpose of screens presented in this work, a gene was considered a hit if it is present in the top two Jenks classes.

Public Cancer Dependency Data

Cell line panel estimates of gene dependency based on CRISPR screens were used in the analysis. CERES scores were downloaded from the 2020 Q1 release of the Broad Cancer Dependency Map. Copy Number Bias Corrected Fold Change Values were downloaded from the April 2019 release of the Sanger Project Score.

Antibodies

The antibodies listed below were used for immunoblotting (IB) or immunofluorescence (IF). Primary antibodies: mouse anti-CIP2A (clone 2G10-3B5, Santa Cruz sc80659, 1:500 IF, 1:1000 IB), rabbit anti-CIP2A (Cell Signalling Technologies #14805, 1:5000 IB), rabbit anti-phospho-Histone H2A.X (Ser139) (Cell Signalling Technologies #2577, 1:500 IF), mouse anti-phospho-Histone H2A.X (Ser139) (clone JBW301, Millipore Sigma #05-636, 1:5000 IF), mouse anti-CHK1 (Santa Cruz sc8408, 1:500 IB), rabbit anti-phospho-CHK1 (Ser345) (Cell Signalling Technologies #2348, 1:1000 IB), rabbit anti-KAP1 (Bethyl A300-274A, 1:10000 IB), HRP-conjugated mouse anti-FLAG M2 (Sigma A8592, 1:1000-5000 IB), mouse anti-FLAG M2 (Sigma G1804, IB), rat anti-FLAG (BioLegend #637301, 1:1000 IF), rabbit anti-TOPBP1 (Abcam ab2402, 1:2000 IF, 1:5000 IB or 1:1500 IB using yeast extracts), rabbit anti-TOPBP1 (ABE1463, Millipore, 1:300 IF), mouse anti-alpha-tubulin (Calbiochem CP06, 1:2000 IB), rat anti-HA (Roche 11867423001, 1:200 IB and IF or 1:500 IB using yeast extracts), mouse anti-CENPA (Abcam ab13939, 1:2000 IF), sheep anti-MDC1 (Serotec/Bio-Rad AHP799, 1:1000 IF), rabbit anti-MDC1 (Abcam ab11171, 1:1000 IF), rabbit anti-GAL4 DNA Binding Domain (Upstate 08283, 1:5000 IB), rat anti-Tubulin (YOL1/34) (Abcam ab6161, 1:2000 IB).

Secondary antibodies for immunoblots: IRDye 800CW goat anti-mouse IgG and IRDye 680RD goat anti-rabbit IgG (LiCOR 926-32210 and 926-68071, 1:5000 or 1:50000 using yeast extracts), HRP-conjugated sheep anti-mouse IgG (GE Healthcare NA931, 1:5000), HRP-conjugated goat anti-rabbit IgG (Cedarlane #111-035-144, 1:5000), and HRP-conjugated goat anti-rat IgG (Cedarlane 112-035-003, 1:5000 or 1:50000 using yeast extracts). Secondary antibodies for immunofluorescence: AlexaFluor 488-donkey anti-rat IgG (Thermo Fisher Scientific A21208, 1:2000), AlexaFluor 647-donkey anti-mouse IgG (Thermo Fisher Scientific A31571, 1:2000), AlexaFluor 488-goat anti-mouse IgG (Thermo Fisher Scientific A11029, 1:2000 or 1:1000 for high content microscopy), AlexaFluor 555-goat anti-mouse IgG (Thermo Fisher Scientific A21424, 1:2000), AlexaFluor 647-goat anti-mouse IgG (ThermoFisher Scientific A21236, 1:2000), AlexaFluor 647-goat anti-rabbit IgG (ThermoFisher Scientific A21244, 1:2000 IF), AlexaFluor 488-goat anti-rabbit IgG (Thermo Fisher Scientific A11034, 1:2000), AlexaFluor 555-donkey anti-sheep IgG (Thermo Fisher Scientific A21436, 1:2000), AlexaFluor 568-goat anti-rabbit IgG (Thermo Fisher Scientific A11011, 1:1000).

Short Interfering RNAs

The following siRNAs were used in this study: Dharmacon siGENOME Non-Targeting siRNA non-targeting siRNA #2 D-001210-02-20 and #3 D-001210-03-20, ON-TARGET Plus PPP2R5A (PPP2A B56α) SMARTpool L-009352-00-0005, ON-TARGET Plus PPP2R5C (PP2A B56γ) SMARTpool L-009433-00-0005, ON-TARGET Plus KIAA1524 (CIP2A) SMARTpool L-014135-01-0005, siGENOME MDC1 SMARTpool M-003506-04-0005, siGENOME TOPBP1 SMARTpool M-012358-01-0005).

Fine Chemicals

The study used: camptothecin (CPT, Sigma-Millipore), hydroxyurea (Sigma), nocodazole (Sigma), Shield-1 (Takara Bio USA, Inc), Aqua-Shield-1 (AS1; CheminPharma) Celastrol (SelleckChem, S1290), TD-52 (Axon Medchem, #2700), olaparib (SelleckChem, S1060), RO-3306 (SelleckChem, S7747), AZD6738 (SelleckChem, S7693), and aphidicolin (Focus Biochemicals, 10-2058). Concentration and duration of treatment is indicated in the legends of the corresponding figures.

High Content Imaging

To analyze γH2AX focus formation, cells were seeded in 96-well plates (7,500 cells/well), cultured for 24 h, incubated in medium containing 20 mM EdU (5-ethynyl-2-deoxyuridine, Life Technologies) for the final 30 min and then washed with PBS and fixed with 4% paraformaldehyde (PFA) in PBS for 10 min at room temperature (RT). Cells were then processed for gH2AX staining. Prior to the click reaction, immunocomplexes were fixed again using 4% PFA/PBS for 5 min. Cells were rinsed with PBS and incubated with EdU staining buffer (150 mM Tris/HCl pH 8.8, 1 mM CuSO4, 100 mM ascorbic acid and 10 mM AlexaFluor 647 Azide (Life Technologies)) for 30 min. After rinsing with PBS, images were acquired on an IN Cell Analyzer 6000 automated microscope (GE Life Sciences) with a 60× objective. Image analysis was performed using Columbus (PerkinElmer). Cell cycle profiling and analysis was evaluated based on EdU and DAPI staining.

Immunofluorescence

Cells were grown and fixed on glass coverslips with 2-4% PFA, permeabilized with 0.3% Triton X-100 in PBS, and blocked with 5% BSA in PBS+0.2% Tween-20. For RPA staining, cells were pre-extracted with 0.5% Triton-X-100 in CSK buffer (10 mM PIPES pH 7.0, 100 mM NaCl, 300 mM sucrose, 3 mM $MgCl_2$) for 10 min on ice, washed once with CSK and once with PBS before PFA fixation. To analyze RAD51 foci, cells were incubated for 10 min on ice in nuclear pre-extraction buffer (20 mM HEPES pH 7.4, 20 mM NaCl, 5 mM $MgCl_2$, 0.5% NP-40, 1 mM DTT, and 1× cOmplete EDTA-free protease inhibitor cocktail (Roche)) and washed once with PBS before fixing with 3% PFA. Cells were then blocked with 5% BSA in PBS+0.2% Tween-20 and stained for 2 h with primary antibodies in blocking buffer, washed with PBS+0.2% Tween-20, incubated for 1 h with appropriate secondary antibodies plus 0.8 μg/ml DAPI, then washed twice with PBS+0.2% Tween-20 and a final wash with PBS. For EdU staining, cells went through a second round of fixation with 3% PFA for 5 min, and processed for click chemistry with Alexa Fluor azide (Thermo-Fisher) according to the manufacturer's instructions. Coverslips were mounted onto glass slides with ProLong Gold mounting reagent (Invitrogen). Images were acquired using a Zeiss LSM780 laser-scanning microscope (Oberkochen, Germany). Foci were manually counted.

For assessing the colocalization of MDC1, TOPBP1 and CIP2A, U2OS cells were reverse transfected with a final concentration of 10 nM siRNA using Lipofectamine RNAiMAX (Invitrogen) on coverslips in 6-well plates. Nocodazole was added to the media at a final concentration of 100 ng/mL 16 h before collection. 48 h after transfection, cells were irradiated with 2 Gy of ionizing radiation using a Faxitron X-ray cabinet (Faxitron, Tucson, AZ) and allowed to recover for 1 h prior to fixation as described for immunofluorescence. Foci were counted manually and at least 50 mitotic cells per condition were imaged in each experiment.

For the experiments relating to the mitotic structures labelled by CIP2A and TOPBP1, U2OS wild-type and $MDC1^{-/-}$ cell lines were seeded on coverslips and either treated with 400 nM aphidicolin for 16 h (overnight) or left untreated. In order to perform immunofluorescence, cells were quickly washed once with cold PBS and then fixed with ice-cold methanol for 10 min on ice. Methanol was discarded and cells were washed two times with PBS before incubation with blocking buffer (10% FBS in PBS) for at least 1 h. Incubation with primary antibodies diluted in 5% FBS-PBS was performed overnight at 4° C. in a humidity chamber. Coverslips were then washed 3×10 min with blocking buffer and incubated with AlexaFluor-conjugated secondary antibodies for 1 h at room temperature in the dark. After washing 3×10 min with PBS, coverslips were mounted on glass microscopy slides (Thermo Scientific, 630-1985, dimensions L76×W26 mm) with VECTASHIELD mounting medium containing 0.5 μg/mL (DAPI) (Vector Laboratories, H-1200).

Confocal images were acquired using a Leica SP8 inverse confocal laser scanning microscope with a 63×, 1.4-NA Plan-Apochromat oil-immersion objective. The sequential scanning mode was applied, and the number of overexposed pixels was kept at a minimum. Images were recorded using optimal pixel size based on Nyquist criterion. At least 10 fields per condition with 10 to 15 z-sections were acquired, with 8-bit depth. Quantification of the foci was performed manually based on maximum intensity projections. Representative grayscale images were pseudocolored and adjusted for brightness and contrast in Adobe Photoshop CC 2020 by using adjustment layers.

Immunoblotting

Cell pellets were boiled for 5-10 min in 2×SDS sample buffer (20% (v/v) glycerol, 2% (w/v) SDS, 0.01% (w/v) bromophenol blue, 167 mM Tris-Cl pH 6.8, 20 mM DTT) and separated by SDS-PAGE on gradient gels (Invitrogen). Proteins were transferred to nitrocellulose membranes (GE Healthcare), then blocked with 5% FBS or 5% milk in TBST and probed for 2 h with primary antibodies. Membranes were washed three times for 5 min with TBST, then probed with appropriate secondary antibodies for 1 h, and washed again with TBST, three times for 5 min. Secondary antibody detection was achieved using an Odyssey Scanner (LiCOR) or enhanced chemiluminescence (ECL, Thermo Fisher Scientific #34579).

Cytogenetic Analyses

To monitor chromosome aberrations, $0.5×10^6$ puromycin-selected RPE1-hTERT cells of the indicated genotypes were seeded in 10-cm dishes 3 d after transduction with virus particles expressing NLS-GFP-sgAAVS1 (control) or an NLS-GFP-sgRNA targeting a specific gene of interest. 4 d later 100 ng/mL KaryoMAX colcemid (Gibco/Thermo Fisher) was added for 2 h, and cells were harvested. To analyze sister chromatid exchange, $0.75×10^6$ RPE1-hTERT cells of the indicated genotypes were seeded in 10-cm dishes. 24 h after seeding, BrdU (final concentration 10 μM) was added to the media and cells were grown for 48 h; 100 ng/mL KaryoMAX colcemid (Gibco/Thermo Fisher) was added for the final 2 h. For cell harvesting, growth medium was stored in a conical tube. Cells were gently washed and treated twice for 5 min with 1 mL of trypsin. The growth medium and the 2 mL of trypsinization incubations were centrifuged (1000 rpm, 5 min, 4° C.). Cells were then washed with PBS and resuspended in 75 mM KCl for 15 min at 37° C. Cells were centrifuged again, the supernatant was removed and cells were fixed by drop-wise addition of 1 mL fixative (ice-cold methanol:acetic acid, 3:1) while gently vortexing. An additional 9 mL of fixative was then added, and cells were incubated at 4° C. for at least 16 h. Once fixed, metaphases were dropped on glass slides and air-dried overnight, protected from light.

To visualize chromosomal aberrations, slides were dehydrated in a 70%, 95% and 100% ethanol series (5 min each), air-dried and mounted in DAPI-containing ProLong Gold mounting medium (Molecular Probes/Thermo Fisher). To visualize sister chromatid exchanges (SCE) slides were rehydrated in PBS for 5 min and stained with 2 μg/mL Hoechst 33342 (Thermo Fisher) in 2×SSC (final concentration 300 mM NaCl, 30 mM sodium citrate, pH 7.0) for 15 min. Stained slides were placed in a plastic tray, covered with a thin layer of 2×SSC and irradiated with 254 nM UV light (~5400 $J/m^2$). Slides were subsequently dehydrated in a 70%, 95% and 100% ethanol series (5 min each), air-dried and mounted in DAPI-containing ProLong Gold mounting medium (Molecular Probes/Thermo Fisher). Images were captured on a Zeiss LSM780 laser-scanning confocal microscope.

LacR/LacO Assays

For monitoring recruitment of endogenous CIP2A to FLAG-tagged TOPBP1 foci we used U2OS-FokI cells, which contain an integrated LacO array. These cells, which are known also as U2OS-DSB [Tang, J. et al., *Nature structural & molecular biology*, doi:10.1038/nsmb.2499 (2013)], are referred to in the text as U2OS-lacO$_{256}$ cells because they were without any induction of FokI. $1.8×10^5$ cells were seeded in 6-well plates containing glass coverslips. 24 h after seeding, cells were transfected using 1 μg of pcDNA5-LacR-FLAG or pcDNA5-LacR-FLAG-TopBP1 (full length, fragments, or mutants) using Lipofectamine 2000. Cells were fixed with 4% PFA 48 h after transfection and stained for immunofluorescence. For monitoring recruitment of Flag-CIP2A, U2OS-FokI cells were transduced with pHIV-NAT constructs. After 0.1 mg/mL nourseothricin selection and cell expansion, 2×10$^5$ cells were seeded in 6-well plates. The next day, cells were transfected using 1 µg of pcDNA5-LacR-TOPBP1. 24 h later, cells were seeded in a 96-well plate (~20,000 cells per well), cultured for 24 h and fixed with 2% PFA and stained for immunofluorescence. Images were acquired on an IN Cell Analyzer 6000 automated microscope (GE Life Sciences) with a 60× objective.

Cell Proliferation (IncuCyte) Assays

MDA-MB-436, DLD1 wild-type and DLD1 BRCA2$^{-/-}$ cells were infected with an empty virus containing the destabilization domain (DD) alone (pHIV-NAT-DD-FLAG) or virus containing an expression cassette for DD-tagged B6L (pHIV-NAT-DD-FLAG-TOPBP1-756-891). After nourseothricin selection (0.1 mg/mL for MDA-MB-436, 0.2 mg/mL for DLD1) and cell expansion, cells were seeded in 96-well plates (500-4,000 cells depending on cell line and genotype) and treated with 1 µM of Shield-1 or Aqua-Shield-1. The following day, plates were transferred into an IncuCyte Live-Cell Analysis Imager (Essen/Sartorius). Cell confluency was monitored every 4 h up to 10 d post-seeding.

Micronuclei (MNi) Assay

For TOPBP1 rescue experiments, DLD1 wild-type and BRCA2$^{-/-}$ cells stably expressing 2×HA-TOPBP1 were generated by viral transduction and selection with blasticidin (7.5 µg/mL for parental cells, 10 µg/mL for BRCA2$^{-/-}$ cells). 3 days after transduction with sgRNA viral particles (as described in the clonogenic survival assays), cells were seeded in a 96-well plate (1,500 for wild-type cells; 4,000 for BRCA2$^{-/-}$ cells) and cultured for 4 additional days. For inducible B6L expression experiments, DLD1 and MDA-MB-436 cells were seeded in a 96-well plate (1,500 for DLD1 wild-type cells; 4,000 for DLD1 BRCA2$^{-/-}$ cells; 14,000 for MDA-MB-436) and cultured for up to 4 days in the presence of Aqua-Shield-1.

For detection of micronuclei, cells were fixed with 2% PFA, washed 3 times with PBS, permeabilized with 0.3% Triton X-100 in PBS for 5 min, washed 3 times with PBS, incubated for 1 h with PBS+DAPI (0.5 µg/mL). Alternatively, cells were stained for immunofluorescence (CENPA detection). After the last wash with PBS, images were acquired on an IN Cell Analyzer 6000 automated microscope (GE Life Sciences) with a 40× objective. Micronuclei were automatically detected and counted using the Columbus analysis tool (PerkinElmer).

Yeast Assays

Yeast two-hybrid assay was conducted using Matchmaker GAL4 two-hybrid system 3 (Clontech/Takara, USA). Bait and prey vectors were co-transformed into the yeast strain AH109 (Clontech/Takara, USA), using a standard high-efficiency transformation protocol, and plated onto media lacking tryptophan and leucine (SD-Trp-Leu) for 3 days to select for cells harboring the two plasmids. Single colonies were isolated and the interaction between bait and prey was assessed by a serial deletion assay based on the ability to grow on selective media lacking leucine, tryptophan, histidine and adenine (SD-Leu-Trp-His-Ade). Viability assays were performed using yeast cultures grown overnight at 30° C. in SD-Trp-Leu to maintain plasmid selection. Ten-fold serial dilutions of cells were spotted on SD-Trp-Leu and SD-Leu-Trp-His-Ade containing 5 mM 3-amino-1,2,4-triazole (3-AT). Plates were imaged after 4 days of incubation at 30° C.

Yeast Protein Extracts

For protein extracts, the cellular pellet of 20 mL of cell suspension (1×10$^7$ cells/mL) was washed twice with 1 mL of 20% trichloroacetic acid (TCA) and suspended in 50 µL of 20% TCA. Cells were broken with acid-washed glass beads (Sigma G8772) by vortexing for 3 minutes at maximum speed. After addition of 100 µL of 5% TCA, precipitated proteins were transferred into a new 1.5 mL tube and centrifuged at 3000 rpm for 10 min at room temperature. The supernatant was removed, and the pellets of proteins suspended in 100 µL of 2×SDS sample buffer (20% (v/v) glycerol, 2% (w/v) SDS, 0.01% (w/v) bromophenol blue, 167 mM Tris-Cl pH 6.8, 20 mM DTT)). The pH was neutralized with 60 µl of 2M Tris base. The protein extract was boiled for 5 minutes at 95° C. and centrifuged for 2 minutes at top speed at room temperature. The supernatant was collected, and the protein extract was subjected to SDS-PAGE analysis.

Co-Immunoprecipitation Studies

Confluent 293T cells, either untreated or treated with 100 ng/mL nocodazole (Sigma) for 16 h, were used for each co-immunoprecipitation experiment. Cells were scraped directly into PBS, pelleted by centrifugation at 1000×g for 5 minutes, and lysed by incubation in lysis buffer (50 mM Tris-HCl pH 8, 100 mM NaCl, 2 mM EDTA, 10 mM NaF, 0.5% NP-40, 10 mM MgCl$_2$, 1× cOmplete EDTA-free Mini EDTA-free protease inhibitor tablet (Sigma), 1× Phosphatase inhibitor cocktail 3 (Sigma) and 5 U/mL benzonase (Sigma)) for 30 min on ice. Lysates were then cleared by centrifugation at 21,000×g for 10 min. 1 µg of either mouse anti-CIP2A (2G10-3B5, Santa Cruz sc-80659) or normal mouse IgG (EMD Millipore 12-371) were added to the lysate and incubated with rotation at 4° C. for 1 h. Subsequently, 20 µL of a slurry of protein G Dynabeads (Invitrogen) were added to the lysates and incubated for an additional 1 h at 4° C. Beads were collected using a magnetic rack and washed 4×5 min with 500 µL lysis buffer, then boiled in 25 µL 2×SDS sample buffer. The presence of co-immunoprecipitated proteins were detected by immunoblotting.

Recombinant Protein Purifications and Interaction Assays

MBP and GST proteins expressed in *Escherichia coli* were purified on amylose (New England Biolabs) or glutathione sepharose 4B (GE Healthcare) resins according to the batch method described by the manufacturer and stored in 20 mM Tris-HCl pH 8.0, 150 mM NaCl, 1 mM DTT, 5% glycerol. Pulldown assays were carried out by coupling equimolar amounts of GST or GST-CIP2A (1-560) to glutathione sepharose 4B resin for 1 h at 4° C. in 100 µL of pulldown buffer (PDB: 20 mM Tris-HCl, pH 8.0, 150 mM NaCl, 1 mM DTT, 0.1% Tween-20. 0.1% BSA). After washing with PDB, MBP or MBP-TOPBP1 proteins were added at a three-fold molar excess and incubated for 2 h at 4° C. Beads were extensively washed prior to analysis by immunoblotting.

Yeast two-hybrid assays were conducted using the Matchmaker GAL4 two-hybrid system 3 (Clontech/Takara, USA) as per the manufacturer's instructions. Plates were imaged after 4 d of incubation at 30° C.

For co-immunoprecipitation studies, pre-cleared whole-cell lysates were incubated with 1 µg of either mouse anti-CIP2A (2G10-3B5, Santa Cruz sc-80659) or normal mouse IgG (EMD Millipore 12-371) with rotation at 4° C. for 1 h. Subsequently, 20 µL of a slurry of protein G Dynabeads (Invitrogen) were added to the lysates and incubated for an additional 1 h at 4° C. Beads were collected using a magnetic rack and washed 4 with lysis buffer (50 mM Tris-HCl pH 8, 100 mM NaCl, 2 mM EDTA, 10 mM NaF, 0.5% NP-40, 10 mM MgCl$_2$, 1× cOmplete EDTA-free Mini EDTA-free protease inhibitor tablet (Sigma), 1× Phosphatase inhibitor cocktail 3 (Sigma) and 5 U/mL benzonase (Sigma)), then boiled in SDS sample buffer. The presence of co-immunoprecipitated proteins was detected by immunoblotting.

Pharmacokinetic Measurements

Whole blood was collected over a period of 8 hr from conscious mice by tail snip, volumetrically transferred to tubes containing 0.1 M citrate (3:1 ratio blood/citrate) and frozen (−80° C.). The determination of the total blood concentration was performed by protein precipitation extraction, followed by reversed-phase liquid chromatography and electrospray mass spectrometry (LC-MS/MS). Blood concentration versus time data was converted to plasma concentrations using an in vitro measurement of the blood to plasma ratio. The data were expressed as free plasma concentration using the fraction unbound which was assessed by equilibrium dialysis of AS1 in mouse plasma over a period of 6 h. PK profiles over a 24-hour period were estimated using Phoenix WinNonlin 8.3.1.

Animals

Experiments were conducted in female NOD-SCID mice, n=8 per group (5-7 weeks old, Charles River, St. Constant, Canada). Mice were group-housed on autoclaved corncob bedding in individual HEPA ventilated cages (Innocage® IVC, Innovive, San Diego, CA, USA) in a temperature-controlled environment (22±1.5° C., 30-80% relative humidity, 12-h light/dark). Mice were acclimatized in the animal facility for at least 5 d prior to use. Studies were conducted under a protocol (Protocol number PRN-044) approved by an Animal Care Committee. Animals were housed and experiments were performed at Neomed (Montreal, Canada), which has accreditation from the Canadian Council on Animal Care. Experiments were performed during the light phase of the cycle. Animals had irradiated food (Harlan Teklad, Montreal, Canada) and filtered water ad libitum. The number of animals used was the minimum necessary to achieve an 80% statistical power to detect a 40% change.

Cancer Cell Implantation and Measurement

DLD1 BRCA2$^{-/-}$ EV and B6L-expressing cells were harvested during exponential growth and re-suspended with high glucose RPMI1640 media (#30-2001, ATCC). Mice received a subcutaneous (SC) injection of 10×10$^6$ DLD1 BRCA2$^{-/-}$ cells EV or B6L-expressing cells, in a volume of 0.1 µl, into the right flank. Tumor volume (TV) and body weight (BW) were measured 2-3 times per week. When tumors reached the target size of 150-200 mm$^3$ mice were randomized into several groups (n=8) and treatment with AS1 was initiated. Randomization was done to establish similar tumor volume mean and standard deviation in each group. AS1 was administered intraperitoneal (IP) twice daily (BID) in a volume of 5 mL/kg in phosphate buffered saline (PBS). TV were measured using a digital caliper and calculated using the formula $0.52 \times L \times W^2$. Response to treatment was evaluated for tumor growth inhibition (% TGI) calculated by the formula: % TGI=(($TV_{vehicle/last} - TV_{vehicle/day0}) - (TV_{treated/last} - TV_{treated/day0}))/(TV_{vehicle/last} - TV_{vehicle/day0}) \times 100$. Change in BW was calculated using the formula: % BW change=($BW_{last}/BW_{day0}) \times 100$. The animals enrolled in the study were euthanized (isoflurane/CO$_2$ asphyxiation) when clinical endpoints of BW loss of greater than 20% or a TV of greater than 2000 mm$^3$ were reached.

Statistical Analyses

No statistical methods were used to pre-determine sample sizes but the sample sizes were similar to those reported in previous publications (for example, Noordermeer S. M. et al, Nature 560, 117-121, doi:10.1038/s41586-018-0340-7 (2018)). No data were excluded in the analysis, the experiments were not randomized, and the investigators were not blinded to allocation during experiments and outcome assessment. For sets of experiments with similar types of data, a standard test was selected and used throughout all to keep analysis consistent and to avoid any bias. All tests were two-tailed, unless explicitly stated otherwise. Normality of data was assessed by the Kolmogorov-Smirnov and Shapiro-Wilks' tests, however, for circumstances with continuous data where the number of samples were too low (e.g., n=3), normality of data was assumed to be true. Comparison between two groups was performed by using the t-test with Welch's correction for continuous data and Mann-Whitney test for discrete data. For multiple comparisons, one- or two-way ANOVA tests were used with the following post hoc tests as indicated in parenthesis: Dunn's multiple comparison test (for non-parametric Kruskal-Wallis One-Way ANOVA test), Dunnet's multiple comparison test (for parametric ordinary one-way ANOVA and two-way ANOVA tests). For tests with repeated measures, the extra sum-of-squares F test was used to assess whether a single curve or individual curves best fits the data, and when the non-linear fit was poor or not possible, due to parameter instability, Šidák's multiple comparison tests were used (for parametric repeated measures two-way ANOVA). GraphPad v9.0.2 was used to compute all the statistics.

The following is a detailed description of the study and results.

To identify a complement of genes that is essential for the viability of HR-deficient cells, genome-scale dropout CRISPR-based synthetic lethal screens were carried out in isogenic pairs of BRCA1- and BRCA2-mutated cells in the human RPE1-hTERT (immortalized retinal epithelium) and DLD1 (colon adenocarcinoma) backgrounds, respectively (FIG. 6A).

Figure 6B:
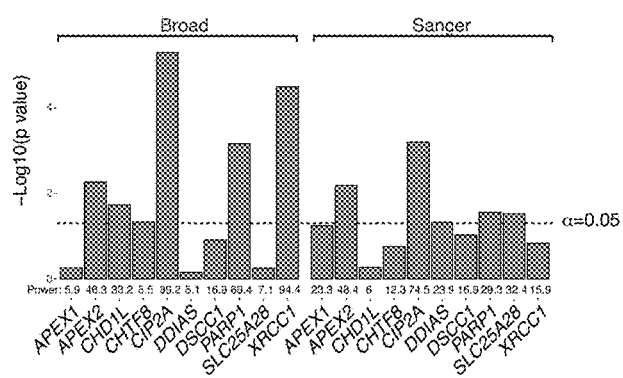
Figure 6C:
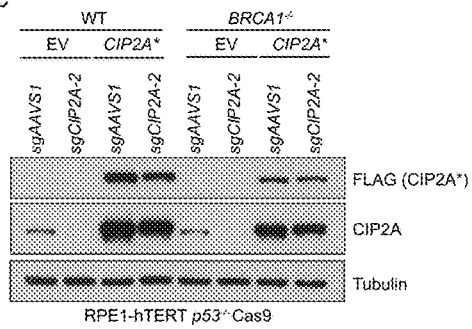
Figure 6D:
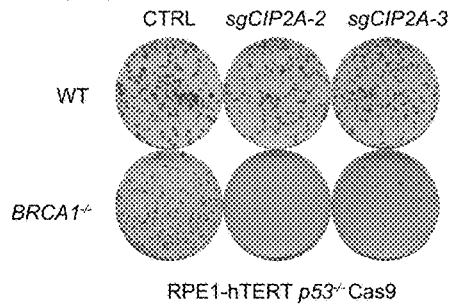
Figure 6E:
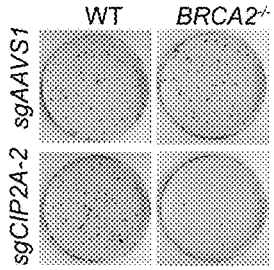

The screens were carried out with the TKOv2 (BRCA1 screen) or TKOv3 (BRCA2 screen) single-guide (sg) RNA libraries and were analyzed with a custom-built analysis pipeline, called CRISPR Count Analysis (CCA), dedicated to the identification of synthetic-lethal genetic interactions (see above methods), defined here as genes essential for the fitness of a mutated cell line (in this case BRCA1$^{-/-}$ or BRCA2$^{-/-}$) but not of their isogenic wild type counterparts. CCA identified 55 and 50 genes that selectively impaired fitness in the BRCA1- or BRCA2-mutated cells, respectively (FIG. 1A,). The top 10 genes common to both screens were APEX1, APEX2, CHD1L, CHTF18, C1P2A, DSCC1, DDIAS, PARP1, SLC25A28 and XRCC1 (FIG. 1A). Of these, PARP1 and APEX2 are known to display robust synthetic lethal interaction with HR deficiency when depleted or inhibited [Mengwasser, K. E. et al. Mol Cell, doi:10.1016/j.molcel.2018.12.008 (2019) Alvarez-Quilon, A. et al. Mol Cell 78, 1152-1165 e1158, doi:10.1016/j.molcel.2020.05.021 (2020); Farmer, H. et al. Nature 434, 917-921 (2005); and Bryant, H. E. et al. Nature 434, 913-917 (2005)]. Other genes with known synthetic lethal interaction with BRCA1/2 such as POLQ [Mateos-Gomez, P. A. et al. Nature 518, 254-257, doi:10.1038/nature14157 (2015) and Ceccaldi, R. et al. Nature 518, 258-262, doi:10.1038/nature14184 (2015)] or the RNase H2-coding genes [Alvarez-Quilon, A. et al. Mol Cell 78, 1152-1165 e1158, oi:10.1016/j.molcel.2020.05.021 (2020) and Zimmermann, M. et al. Nature 559, 285-289, doi:10.1038/s41586-018-0291-z (2018)] were hits in only one of the two cell lines To identify genetic interactions with highest relevance to the tumor setting, the results were analyzed of two large-scale studies of genetic dependencies in cancer cells lines;

the DepMap project [Dempster, J. M. et al. Extracting Biological Insights from the Project Achilles Genome-Scale CRISPR Screens in Cancer Cell Lines. *bioRxiv*, 720243, doi:10.1101/720243 (2019); and Behan, F. M. et al. *Nature*, doi:10.1038/s41586-019-1103-9 (2019)]. Cell lines were grouped according to whether they harbor or not biallelic damaging alterations in BRCA1 or BRCA2, and then the distribution was plotted of their gene-level depletion scores (where lower numbers indicate negative impact on cell fitness) Despite both datasets having only a few annotated biallelic BRCA1 or BRCA2-mutated cell lines, C1P2A targeting had the most penetrant, significant and profound impact on the fitness of BRCA1/2-deficient cancer cells in both datasets, with APEX2 also showing good separation between the BRCA+ and BRCA-deficient groups (FIG. 1B, FIG. 1C, and FIG. 6B). Since these studies highlighted C1P2A as having a particularly strong genetic interaction with BRCA1/2, clonogenic survival assays were then used to confirm the synthetic lethality conferred by the loss of CIP2A in the engineered BRCA1$^{-/-}$ and BRCA2$^{-/-}$ cell lines (FIG. 1D-FIG. 1G and FIG. 6A-FIG. 6E). Re-introduction of an sgRNA-resistant CIP2A transgene into BRCA1$^{-/-}$ and BRCA2$^{-/-}$ cells rescued the synthetic-lethality phenotype (FIG. 1E and FIG. 1G). Lastly, a "reverse" CRISPR-based synthetic lethality screen was performed with a CIP2A knockout query cell line (in the RPE1-hTERT p53$^{-/-}$ Cas9 background [Hustedt, N. et al. *Open Biol* 9, 190156, doi:10.1098/rsob.190156 (2019)]), that further confirmed synthetic lethality between CIP2A and HR genes, as BRCA1, BRCA2, PALB2, and FANCM were among the top synthetic-lethal hits, as determined by CCA and BAGEL2 [Kim, E. & Hart, T. *bioRxiv*, 2020.2005.2030.125526, doi: 10.1101/2020.05.30.125526 (2020)] (FIG. 1H). Thus, CIP2A is essential in a broad range of engineered and tumor-derived HR-deficient cell lines.

Figure 7A:
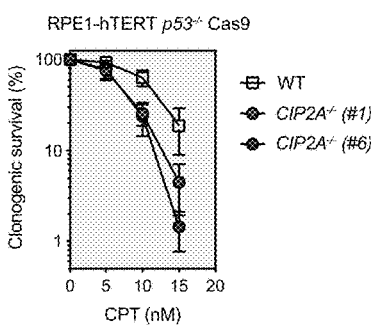
FIG. 7A-FIG. 7F show loss of CIP2A does not cause DNA lesions requiring HR for their repair.
Figure 7B:
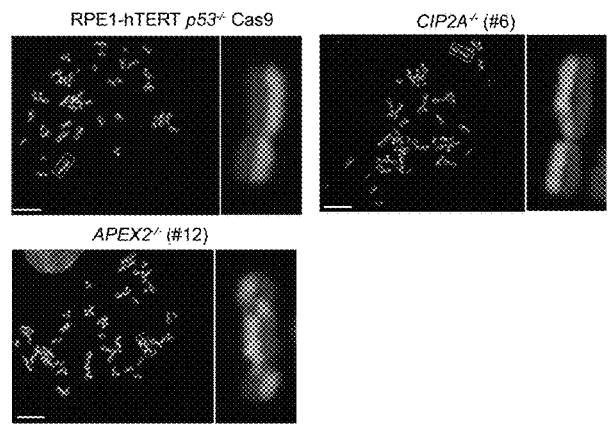

CIP2A encodes a protein of 905 amino acid residues that can be broadly split in two regions: a highly structured N-terminal half consisting of an armadillo (arm) repeat core (residues 1-560) [Wang, J. et al. *EMBO Rep* 18, 437-450, doi:10.15252/embr.201642788 (2017)] followed by a C-terminal half predicted to form a coiled-coil [Wang, J. et al. supra (2017)] (FIG. 11). The exact molecular function of CIP2A is unknown although it is a reported inhibitor of the PP2A phosphatase and is overexpressed in multiple tumor types [Junttila, M. R. et al. *Cell* 130, 51-62, doi:10.1016/j.cell.2007.04.044 (2007) and Khanna, A., et al. *Cancer Res* 73, 6548-6553, doi:10.1158/0008-5472. CAN-13-1994 (2013)]. Mice homozygous for a near-null Cip2a allele produced by gene-trapping have a typical lifespan and develop normally with the exception of a mild spermatogenesis defect [Ventela, S. et al. *PLoS One* 7, e33209, doi:10.1371/journal.pone.0033209 (2012)]. CIP2A levels were examined in BRCA1- or BRCA2-deficient cells to assess whether HR-deficient cells have increased CIP2A dosage but CIP2A expression was found to be unchanged in those cells A direct role for CIP2A in DNA repair or replication has not been reported. Loss of CIP2A has been associated with sensitivity to ATR inhibitors [Hustedt, N. et al. supra (2019)] and to a few other genotoxins [Olivieri, M. et al. *Cell* 182, 481-496 e421, doi:10.1016/j.cell.2020.05.040 (2020)], including the TOP1 poison camptothecin (FIG. 7A). These initial observations suggested that CIP2A may repair or prevent accumulation of replication-borne DNA lesions that require HR for their repair, as this is the basis for the PARP1-BRCA and APEX2-BRCA synthetic lethality. To test this possibility, spontaneous sister-chromatid exchanges (SCEs), reflective of replication-associated DNA lesions that are repaired by HR [Wilson, D. M., 3rd & Thompson, L. H. *Mutat Res* 616, 11-23, doi:10.1016/j.mrfmmm.2006.11.017 (2007)] were investigated. In contrast to APEX2 sgRNAs or PARP inhibition [Ito, S., Murphy, C. G., et al. *PLoS One* 11, e0159341, doi:10.1371/journal.pone.0159341 (2016)], CIP2A-depleted cells experience near-basal levels of spontaneous SCEs, indicating that CIP2A loss does not greatly increase the load of DNA lesions that engage the HR pathway (FIG. 2A and FIG. 7B). In support of this, CIP2A$^{-/-}$ cells have similar levels of spontaneous DSBs marked by g-H2AX than its parental cell line (FIG. 2B). Together, these results indicate that the CIP2A-BRCA synthetic lethality is not due to an increased load of DNA lesions that are normally processed by HR.

Figure 7C:
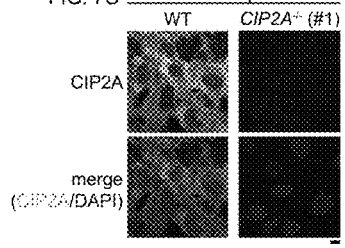
Figure 7D:
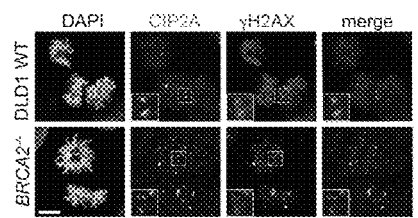

A lack of direct involvement of CIP2A in DNA repair or DNA replication is further supported by the subcellular localization of CIP2A. As previously noted [Kim, J. S., Kim, E. J., Oh, J. S., Park, I. C. & Hwang, S. G. *Cancer Res* 73, 6667-6678, doi:10.1158/0008-5472. CAN-13-0888 (2013)], CIP2A is cytoplasmic in interphase cells as determined by immunofluorescence microscopy (FIG. 7C). DNA damage caused by ionizing radiation (IR) did not promote CIP2A translocation from the cytoplasm to the nucleoplasm but rather led to a striking formation of IR-induced foci by CIP2A in mitotic, but not interphase, cells (FIG. 2C-FIG. 2F). Increased frequency of mitotic CIP2A foci was observed in BRCA2$^{-/-}$ cells over their BRCA+ counterparts (FIG. 2F and FIG. 7D), indicating that CIP2A responds to DNA damage only during M phase and the response is likely relevant to the CIP2A-BRCA synthetic lethality.

Figure 7E:
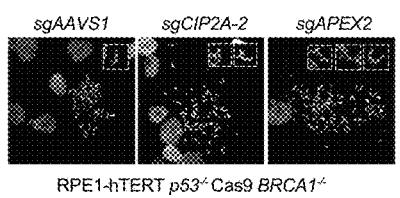
Figure 7F:
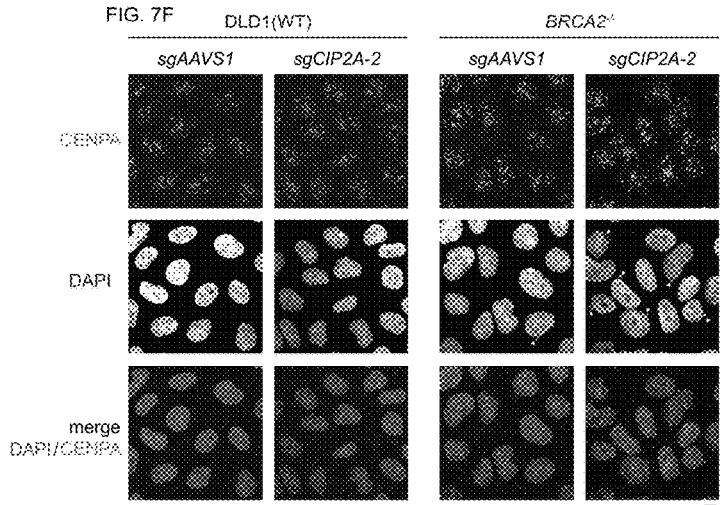

The metaphases of HR-deficient cells treated with PARP inhibitors or depleted of APE2 display increased numbers of radial chromosomes [Alvarez-Quilon, A. et al. supra (2020); Bunting, S. F. et al. *Cell* 141, 243-254, doi:S0092-8674(10) 00285-0 [pii] 10.1016/j.cell.2010.03.012 (2010)], which are likely caused by the unscheduled action of non-homologous end-joining on DNA lesions that are normally repaired by HR. Depletion of CIP2A in BRCA1$^{-/-}$ cells did not increase radial chromosome formation but an increase in chromatid breaks was detected (FIG. 2H and FIG. 7E). Together with the near-normal SCE frequency of CIP2A$^{-/-}$ cells, these results further indicate that CIP2A must support the viability of HR-deficient cells via a mechanism distinct from PARP or APE2. A clue to this mechanism emerged when it was observed that depletion of CIP2A led to a striking increase in the frequency of micronuclei (MNi) formed in BRCA2$^{-/-}$ cells (FIG. 2I and FIG. 7F). These micronuclei were largely CENPA-negative, indicating that they originate from the mis-segregation of acentric (i.e., broken) chromosomes (FIG. 2I). The lesions causing micronucleation in CIP2A-deficient cells are likely to be originating from defective DNA replication since inducing DNA replication stress in DLD1 cells either with a low dose of the DNA polymerase inhibitor aphidicolin, or the ATR inhibitor AZD6738, led to a similar accumulation of acentric micronuclei in two independent CIP2A$^{-/-}$ clonal cell lines. Thus, CIP2A may promote the viability of HR-deficient cells by guarding against the formation and/or mis-segregation of acentric chromosomes arising as a consequence of replication-associated DNA damage; these types of lesions are frequently found in BRCA-deficient cells (Feng, W & Jasin, Nat Commun 8, 525, doi:10.1038/s41467-017-00634-0 (2017)).

The acentric micronucleation caused by loss of CIP2A in HR-deficient cells was revealing in light of work showing that MDC1 and TOPBP1 form mitotic IR-induced foci that promote segregation of broken chromsosomes [Leimbacher, P. A. et al. *Mol Cell* 74, 571-583 e578, doi:10.1016/j.molcel.2019.02.014 (2019)]. Analysis of DepMap data [Dempster, J. M. et al. supra (2019)] also showed essentiality profiles for MDC1 and TOPBP1 that are highly correlated to those of C1P2A (FIG. 3A). Similarly, genotoxin sensitivity profiles generated from a DNA damage chemogenomic dataset [Olivieri, M. et al. supra (2020)] also links C1P2A to MDC1 (FIG. 8A). CIP2A may thus collaborate with MDC1 and TOPBP1 to promote the accurate segregation of damaged chromosomes. CIP2A, MDC1 and TOPBP1 colocalized at IR-induced mitotic foci in nocodazole-treated cells (FIG. 3B). Protein depletion studies with siRNAs further showed that MDC1 was acting upstream of TOPBP1 and CIP2A, and that the localization of TOPBP1 and CIP2A to mitotic broken chromosomes was dependent on each other (FIG. 3C and FIG. 8B).

The above data suggest that CIP2A acts downstream of MDC1 in promoting the segregation of MDC1-marked broken chromosomes. However, loss of MDC1 does not cause lethality in BRCA2-deficient cells (FIG. 3C). This observation suggested that the MDC1-dependent modulation of DSBs in mitosis may not be relevant to the CIP2A-BRCA synthetic lethality.

However, TOPBP1 is known to have MDC1-independent roles in promoting genome integrity during mitosis [Leimbacher, P. A. et al. *Mol Cell* 74, 571-583 e578, doi:10.1016/j.molcel.2019.02.014 (2019); Bagge, J., et al., *Semin Cell Dev Biol, doi:*10.1016/j.semcdb.2020.08.009 (2020); Broderick, R., et al. *Nat Commun* 6, 6572, doi:10.1038/ncomms7572 (2015)]. Analysis of TOPBP1 and CIP2A localization on mitotic chromosomes of wild type or MDC1$^{-/-}$ U2OS cells showed that TOPBP1 and CIP2A colocalized in a number of mitotic structures in the absence of IR treatment in a manner that was stimulated by low-dose treatment (400 nM) with aphidicolin, a DNA polymerase inhibitor (FIG. 3D-FIG. 3F and FIG. 8D). These structures included centrosomes, a known site of TOPBP1 and CIP2A localization [Bang, S. W. et al. *Exp Cell Res* 317, 994-1004, doi:10.1016/j.yexcr.2011.01.022 (2011) and Jeong, A. L. et al. *J Biol Chem* 289, 28-40, doi:10.1074/jbc.M113.507954 (2014)] (FIG. 3D, inset I), small foci often found in pairs (FIG. 3D, inset ii) as well as filament-like structures (FIG. 3E and FIG. 8D). Centrosomal localization is seen in every cell irrespective of treatment whereas the foci and filaments were rare in untreated HR-proficient cells, but their frequency could be increased by aphidicolin treatment in a manner that was mostly independent of MDC1 (FIG. 3F and FIG. 8E). Remarkably, in the tumor-derived cell line MDA-MB-436, which is defective in BRCA1 [Elstrodt, F. et al. *Cancer Res* 66, 41-45, doi:10.1158/0008-5472. CAN-05-2853 (2006)], CIP2A-TOPBP1 filaments were present in nearly all mitotic cells examined (91±2.7%, n=3; FIG. 3G and FIG. 8F). These data suggest that CIP2A can colocalize with TOPBP1 independently of MDC1 on replication-associated DNA lesions that are transmitted to mitosis. In further support of this, 28% of the spontaneous CIP2A foci and 100% of the CIP2A filament-like structures in DLD BRCA2$^{-/-}$ prophase cells were found to be resistant to MDC1 depletion. Furthermore, analysis of spontaneous RPA foci in BRCA2$^{-/-}$ prophase cells to mark under-replicated DNA (Farmer H. et al, Nature 434, 917-921 (2005)), found that 82% of them co-localized with CIP2A, confirming that CIP2A responds to DNA lesions originating from defective DNA replication. Spontaneous CIP2A foci are much more frequent than RPA foci in DLD BRCA2$^{-/-}$ prophase cells, further indicating that CIP2A responds to various types of DNA lesions in mitotic cells that include, but are not limited to, under-replicated DNA. These results also point to under-replicated DNA and/or replication-originating lesions as being ultimately responsible for the CIP2A-BRCA synthetic lethality.

CIP2A-TOPBP1 mitotic structures were also observed in the tumor-derived cell line MDA-MB-436, which is defective in BRCA1 (Elstrodt F, et al, Cancer Res. 66, 41-45, doi:10.1158/0008-5472. CAN-05-2853 (2006)). In MDA-MB-436 cells, the CIP2A-TOPBP1 filaments appear to be seeded from chromosomal loci in mitosis but seem to elongate over time and could sometimes be observed as detached from the chromatin mass in some dividing cells (FIG. 8F). The data suggest they are initially formed as a consequence of unresolved replication-associated DNA lesions and are thus likely relevant to the CIP2A-BRCA synthetic lethality. The data also suggest that higher-order assembly of the CIP2A-TOPBP1 complex may be important for its role in genome maintenance. In support, conserved coiled-coil region of CIP2A were found both necessary for the localization of the CIP2A-TOPBP1 complex to spontaneous mitotic DNA lesions and for the viability of BRCA2$^{-/-}$ cells, suggesting that higher-order assembly by this complex is central feature of its function.

Figure 9H:
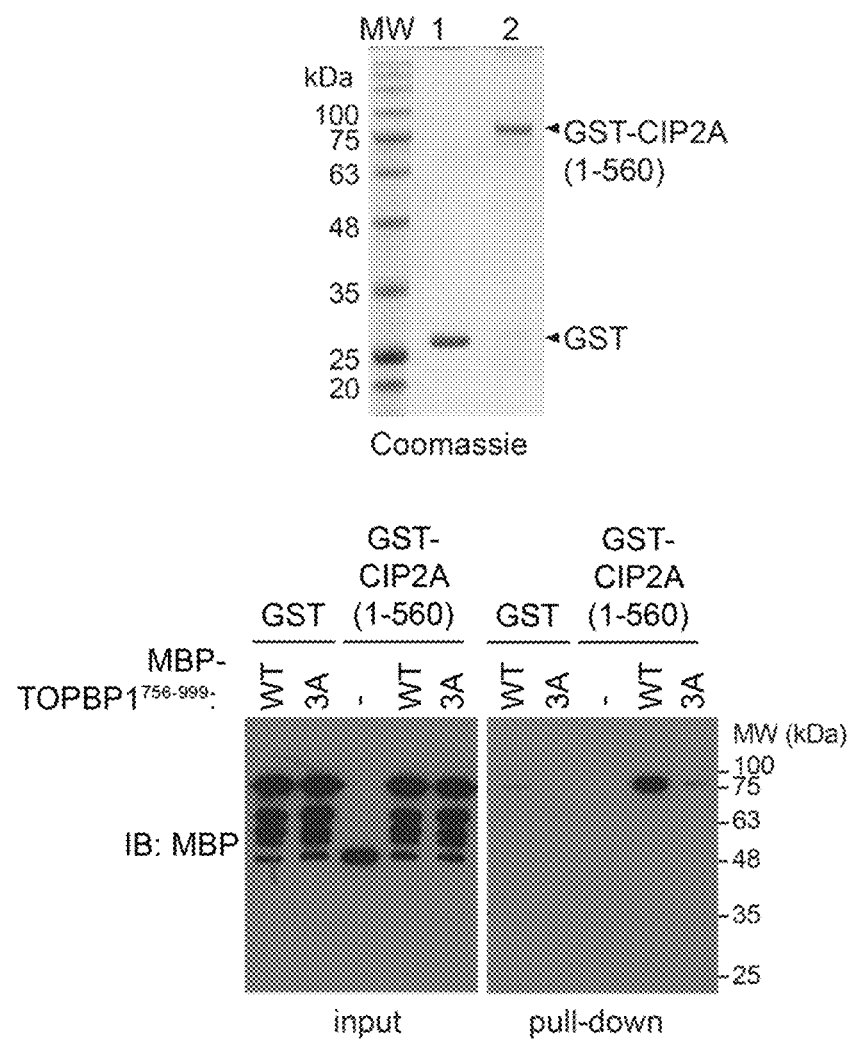

The intimate and interdependent localization of CIP2A and TOPBP1 on mitotic structures hinted that they may interact with each other. Indeed, CIP2A retrieves TOPBP1 in co-immunoprecipitation assays (FIG. 4A) and does so in an MDC1-independent manner. The two proteins were also found to interact in a cellular co-localization assay where TOPBP1 fused to the LacR DNA-binding domain is targeted to a chromosomal site with ~256 copies of the LacO sequence integrated (FIG. 4B—FIG. 4D). The LacR/LacO assay was conducted with interphase cells, suggesting that some CIP2A can shuttle in and out of the nucleus. The TOPBP1-binding region on CIP2A mapped to the highly structured arm-repeat core (residues 1-560; FIG. 4D), a finding which was confirmed by yeast two-hybrid, which also suggested that the interaction is direct (FIG. 4E). The CIP2A-interacting region of TOPBP1 was mapped to a region located between BRCT5 and BRCT6, in a segment encompassing residues 830-851 (by yeast two-hybrid; FIG. 4e) or residues 776-851 (with LacR/LacO; FIG. 4F and FIG. 9A, FIG. 9B). Deletion of a segment of TOPBP1 comprising this region, in TOPBP1-D756-891, completely abolished the CIP2A-TOPBP1 interaction as monitored by the LacR/LacO system or yeast two-hybrid (FIG. 4E and FIG. 4F). The yeast two-hybrid system was used to identify point mutants that disrupt binding between CIP2A and TOPBP1 (FIG. 9C). These studies identified a highly conserved three-residue segment on TOPBP1, F837-D838-V839 (FIG. 4G), as critical for interaction with CIP2A in the context of the TOPBP1 830-851 fragment. Mutation of these residues to alanine in the context of full-length TOPBP1 generated the TOPBP1$^3$A mutant, which has impaired interaction with CIP2A in both yeast and mammalian cells (FIG. 4E and FIG. 4F). Finally, the CIP2A-TOPBP1 interaction was reconstituted using bacterially produced proteins, confirming that the interaction is direct and dependent on the FDV residues (FIG. 9H).

The identification of TOPBP1 variants defective in CIP2A binding enabled testing whether the TOPBP1-CIP2A interaction was essential for the viability of BRCA-deficient cells. DLD1 BRCA2$^{-/-}$ cell lines stably transduced with sgRNA-resistant lentiviruses that express TOPBP1, TOPBP1$^3$A and TOPBP1-D756-891 were generated (FIG. 9D) and then the endogenous chromosomal copies of TOPBP1 were inactivated by Cas9-mediated mutagenesis.

As hinted by the depletion studies, cells expressing TOPBP1-D756-891 and TOPBP1³A failed to form mitotic CIP2A IR-induced foci (FIG. 4H and FIG. 9E) and displayed rapid loss of fitness selectively in the BRCA2$^{-/-}$ background upon removal of endogenous TOPBP1 (FIG. 4I and FIG. 9F). The lethality of TOPBP1-D756-891 and TOPBP1³A in BRCA2$^{-/-}$ cells was also accompanied with an increase in micronucleation suggesting lethal chromosome instability (FIG. 4J and FIG. 9G). Thus, CIP2A-TOPBP1 interaction is essential for the viability of HR-deficient cells.

Disrupting the CIP2A-TOPBP1 interaction is an attractive therapeutic strategy. To model this approach, a fragment was identified of TOPBP1 corresponding to residues 756-1000 (FIG. 5A), referred to as "B6L" (for BRCT6-long) that is highly effective at disrupting mitotic CIP2A foci when expressed from a lentiviral vector (FIG. 5B and FIG. 10A). B6L expression is under the control of a FKBP12-derived destabilization domain (DD), [Banaszynski, L. A., et al., Cell 126, 995-1004, doi:10.1016/j.cell.2006.07.025 (2006)] which enables tight induction of B6L expression upon addition of the Shield1 or water-soluble AS1 (Aqua-Shield1) compounds (FIG. 10B). Incucyte imaging of BRCA2$^{-/-}$ cells following induction of B6L, showed a near-complete cessation of proliferation in DLD1 BRCA2$^{-/-}$ cells within 3 days of induction whereas it was innocuous to its BRCA+ parental cell line (FIG. 5C and FIG. 5D). Induction of B6L for 2 days followed by a washout of AS1 (FIG. 5E) led to an irreversible cessation of growth as determined by clonogenic survival (FIG. 5F and FIG. 10O) and was accompanied by rapid and high levels micronucleation, further suggesting that segregation of acentric fragments is a plausible cause of cell death in BRCA-deficient cells (FIG. 5G). The micronucleation was caused by DNA lesions that originate in interphase since holding BRCA2$^{-/-}$ cells in G2 with the CDK1 inhibitor RO-3306 prior to release in mitosis completely suppressed B6L-induced micronucleation. Furthermore, analysis of DLD1 BRCA2$^{-/-}$ cells in late anaphase showed a selective increase in lagging acentric chromosomes upon B6L expression, confirming that the loss of the CIP2A-TOPBP1 interaction causes mis-segregation of acentric fragments. Disruption of the CIP2A-TOPBP1 with B6L did not impair ATR signaling, ruling out that the impact of B6L is due to ATR misregulation (FIG. 10D). B6L expression also impaired the proliferation of the tumor-derived MDA-MB-436 cell line indicating its ability to stunt proliferation of BRCA-deficient cells is not limited to engineered backgrounds (FIG. 5H, FIG. 5I, and FIG. 10e). Together these results indicate that inhibition of the CIP2A-TOPBP1 interaction could provide a therapeutic strategy for HR-deficient cancers.

Figure 11A:
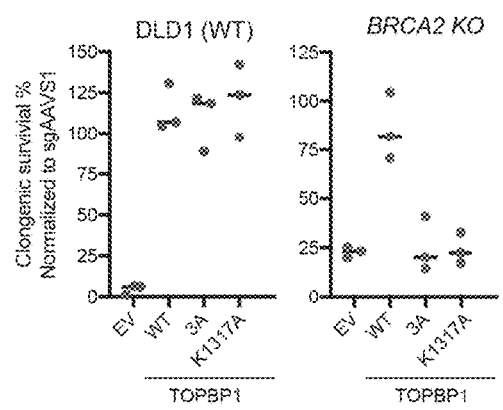
FIG. 11A-FIG. 11B show the phosphopeptide-binding activity of the TOPBP1 BRCT7/8 domains is essential for viability in BRCA2-deficient cells.
Figure 11B:
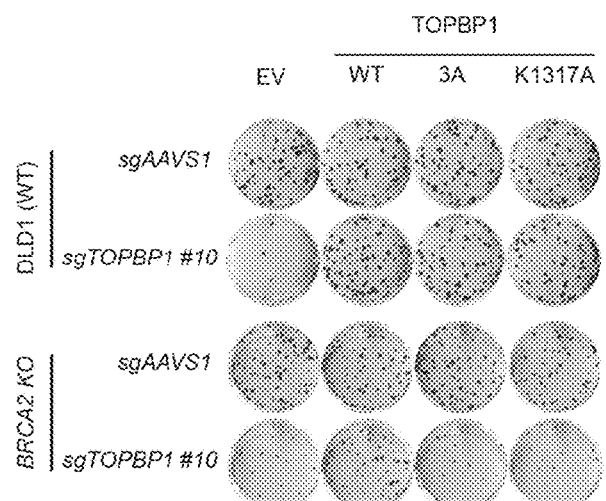

The ability to acutely disrupt the CIP2A-TOPBP1 interaction also allowed investigation of the reported inhibition of PP2A by CIP2A (Junttila M R et al, Cell 130, 51062, doi:10.1016/j.cell.2007.04.044 (2007)) and if it was part of the mechanism by which CIP2A and TOPBP1 promote genome stability and viability of BRCA-deficient cells. CIP2A inhibits PP2A by binding to two PP2A regulatory subunits, B56α and B56γ (Wang, J et al, EMBO Rep 18, 437-450, doi:10.15252/embr.201642788 (2017); Junttila 2007 Supra). If the root cause of the BRCA-CIP2A synthetic lethality was hyperactivity of PP2A, then depletion of the CIP2A-binding B56α/γ subunits should suppress the genome instability (i.e., micronucleation) caused by B6L expression. Support for this possibility was not found as the depletion of B56α/γ by siRNA had no impact on the micronucleation caused by disruption of the CIP2A-TOPBP1 interaction in DLD1 BRCA2$^{-/-}$ cells. Furthermore, recruitment of either HA-tagged B56α or B56γ to the TOPBP1/CIP2A complex was not detected using the LacR/LacO assay. Together, these results suggest that the reported modulation of PP2A activity by CIP2A is unlikely to be relevant for understanding the CIP2A-BRCA synthetic lethality. The K1317A mutation in the BRCT7/8 domain of TOPBP1 causes cell lethality in BRCA2$^{-/-}$ cells and recapitulates the phenotypes caused by CIP2A loss or by the inhibition of the CIP2A-TOPBP1 interaction (via the 3A mutation) (FIG. 11A and FIG. 11B). The BRCT7/8 recognizes phosphopeptides and this data indicates that inhibiting phosphopeptide recognition of BRCT7/8 would kill BRCA-deficient cells.

To test whether disrupting the CIP2A-TOPBP1 interaction could inhibit tumor growth, tumors from DLD1 BRCA2$^{-/-}$ cells transduced with either a control (EV) or B6L-expressing lentivirus in NOD-SCID mice were established. The periodic stabilization of B6L in BRCA2$^{-/-}$ tumors was sufficient to cause striking tumor growth inhibition over the course of a 7-day treatment, reaching 85%. Furthermore, tumor growth inhibition was maintained until the completion of the experiment, 8 days after administration of the last dose of AS1. It was concluded that not only is the inhibition of the CIP2A-TOPBP1 interaction providing an attractive therapeutic strategy for HR-deficient cancers, but the complete and sustained inhibition of the CIP2A-TOPBP1 interaction may not be necessary for achieving BRCA-deficient tumor control.

BRCA-deficient tumors acquire resistance to therapy through multiple mechanisms (Janysek, et al, 2021, Supra) and the identification of strategies to overcome treatment resistance is a high unmet need. Therefore, whether targeting CIP2A or the CIP2A-TOPBP1 interaction also impairs viability of some treatment-resistant BRCA1-deficient cells was investigated. A model of PARP inhibitor resistance, BRCA1$^{-/-}$53 BP1$^{-/-}$ cells (Bunting S. F. et al, Cell 141, 243-254, doi:S0092-8674(10)00285-0 [pii] 0.1016/j.cell.2010.03.012 (2010)) was employed. Using a competitive growth assay, it was observed that genetic ablation of CIP2A with sgRNAs impaired growth of BRCA1$^{-/-}$53 BP1$^{-/-}$ cells nearly as much as BRCA1$^{-/-}$ cells (FIG. 8B). These results suggest that inhibitors of the CIP2A-TOPBP1 interaction may also prove effective in subsets of patients whose tumors progress on PARP inhibitor therapy.

The growth inhibitory properties of two reported inhibitors of CIP2A, celastrol (Liu Z. et al, Carcinogenesis 35, 905-914, doi:10.1093/carcin/bgt395 (2014).) and TD-52, (Yu, H. C. et al, Cell Death Dis 5, e1359, doi:10.1038/cddis.2014.325 (2014)) were tested on DLD1 parental, CIP2A$^{-/-}$ and BRCA2$^{-/-}$ cell lines. Both compounds inhibit growth of all cell lines, to the same extent, irrespective of genotype. These results indicate that the growth inhibitory properties of these compounds are independent of CIP2A and are not selective inhibitors of CIP2A or the CIP2A-TOPBP1 interaction.

The observation that acute inactivation of BRCA1 and BRCA2 causes cellular lethality is in line with a model where BRCA1/2-deficient tumors acquire genetic and/or non-genetic adaptive mechanisms that enable these cells to proliferate in the face of HR deficiency. While p53 inactivation is one genetic means by which cells acquire the ability to tolerate HR-deficiency cells [Banaszynski, L. A., et al., Cell 126, 995-1004, doi:10.1016/j.cell.2006.07.025 (2006); Hakem, R., et al., Nat Genet 16, 298-302, doi: 10.1038/ng0797-298 (1997) and Ludwig, T., et al. Genes & development 11, 1226-1241 (1997), the findings suggest that a dependency on the CIP2A-TOPBP1 complex provides another way to endow HR-deficient cells with the ability to proliferate. The results of this study indicate a role for the CIP2A-TOPBP1 complex in promoting the segregation of chromosomes that did not fully complete DNA replication, or that have experienced DSBs during mitosis. CIP2A either participates in the resolution of incompletely replicated chromosomes or, more likely, that it participates in physically bridging acentric fragments to their centromere-bearing counterpart following the mitotic processing of incompletely replicated chromosomes. In support of this, the conserved coiled-coil region of CIP2A was found to be both necessary for the localization of CIP2A-TOPBP1 complex to spontaneous mitotic DNA lesions and for the viability of BRCA2$^{-/-}$ cells, suggesting that higher-order assembly by this complex is central feature of its function. This role of CIP2A-TOPBP1 will be distinct from other mitotic DNA damage tolerance pathways [Ozer, O. & Hickson, I. D. *Open Biol* 8, doi:10.1098/rsob.180018 (2018)] since the genes coding for proteins known to have central roles in these processes, such as RAD52 (MiDAS) or PICH/ERCC6L (for ultrafine bridge resolution), were not synthetic-lethal with BRCA1/2 in either of the CRISPR screens undertaken.

In conclusion, the CIP2A-TOPBP1 interaction is a therapeutic target for the treatment of HR-deficient tumors. The results described herein also indicate that CIP2A could be an attractive target for overriding acquired therapeutic resistance in some BRCA-deficient tumors, such as BRCA1-mutated cancers with loss of the 53BP1 pathway. Since the loss of CIP2A does not cause high loads of DNA damage in HR-proficient cells, and since Cip2a-deficient mice develop normally with typical lifespan, inhibiting the CIP2A-TOPBP1 interaction should have non-overlapping toxicity with PARP inhibitors, and thus could enable a greater range of therapeutic combinations. Furthermore, CIP2A loss was found to impair fitness in a model of PARP inhibitor resistance, BRCA1$^{-/-}$53 BP1$^{-/-}$ cells (FIG. 10F), therefore, inhibitors of the CIP2A-TOPBP1 interaction may also be effective in subsets of patients that progress on PARP inhibitor therapy. The noted hypersensitivity of CIP2A-deficient cells to ATR inhibitors (Husteddt, N et al, Open Biol 9, 190156, doi:10.1098/rsob.190156 (2019)), also indicates that targeting CIP2A is an additional strategy to enhance the efficacy of ATR inhibitors.

The present invention is not to be limited in scope by the specific embodiments described herein, since such embodiments are intended as but single illustrations of one aspect of the invention and any functionally equivalent embodiments are within the scope of this invention. Indeed, various modifications of the invention in addition to those shown and described herein will become apparent to those skilled in the art from the foregoing description and accompanying drawings. Such modifications are intended to fall within the scope of the appended claims.

All publications, patents and patent applications referred to herein are incorporated by reference in their entirety to the same extent as if each individual publication, patent or patent application was specifically and individually indicated to be incorporated by reference in its entirety. The citation of any reference herein is not an admission that such reference is available as prior art to the instant invention.

FULL CITATIONS FOR PUBLICATIONS

1 Roy, R., Chun, J. & Powell, S. N. BRCA1 and BRCA2: different roles in a common pathway of genome protection. *Nat Rev Cancer* 12, 68-78, doi:10.1038/nrc3181 nrc3181 [pii] (2011).

2 Feng, W. & Jasin, M. BRCA2 suppresses replication stress-induced mitotic and G1 abnormalities through homologous recombination. *Nat Commun* 8, 525, doi:10.1038/s41467-017-00634-0 (2017).

3 Gowen, L. C., Johnson, B. L., Latour, A. M., Sulik, K. K. & Koller, B. H. Brca1 deficiency results in early embryonic lethality characterized by neuroepithelial abnormalities. *Nat Genet* 12, 191-194, doi:10.1038/ng0296-191 (1996).

4 Lord, C. J. & Ashworth, A. PARP inhibitors: Synthetic lethality in the clinic. *Science* 355, 1152-1158, doi:10.1126/science.aam7344 (2017).

5 Mengwasser, K. E. et al. Genetic Screens Reveal FEN1 and APEX2 as BRCA2 Synthetic Lethal Targets. *Mol Cell*, doi:10.1016/j.molcel.2018.12.008 (2019).

6 Alvarez-Quilon, A. et al. Endogenous DNA 3' Blocks Are Vulnerabilities for BRCA1 and BRCA2 Deficiency and Are Reversed by the APE2 Nuclease. *Mol Cell* 78, 1152-1165 e1158, doi:10.1016/j.molcel.2020.05.021 (2020).

7 Farmer, H. et al. Targeting the DNA repair defect in BRCA mutant cells as a therapeutic strategy. *Nature* 434, 917-921 (2005).

8 Bryant, H. E. et al. Specific killing of BRCA2-deficient tumours with inhibitors of poly(ADP-ribose) polymerase. *Nature* 434, 913-917 (2005).

9 Mateos-Gomez, P. A. et al. Mammalian polymerase theta promotes alternative NHEJ and suppresses recombination. *Nature* 518, 254-257, doi:10.1038/nature14157 (2015).

10 Ceccaldi, R. et al. Homologous-recombination-deficient tumours are dependent on Poltheta-mediated repair. *Nature* 518, 258-262, doi:10.1038/nature14184 (2015).

11 Zimmermann, M. et al. CRISPR screens identify genomic ribonucleotides as a source of PARP-trapping lesions. *Nature* 559, 285-289, doi:10.1038/s41586-018-0291-z (2018).

12 Dempster, J. M. et al. Extracting Biological Insights from the Project Achilles Genome-Scale CRISPR Screens in Cancer Cell Lines. *bioRxiv*, 720243, doi:10.1101/720243 (2019).

13 Behan, F. M. et al. Prioritization of cancer therapeutic targets using CRISPR-Cas9 screens. *Nature*, doi:10.1038/s41586-019-1103-9 (2019).

14 Hustedt, N. et al. A consensus set of genetic vulnerabilities to ATR inhibition. *Open Biol* 9, 190156, doi:10.1098/rsob.190156 (2019).

15 Kim, E. & Hart, T. Improved analysis of CRISPR fitness screens and reduced off-target effects with the BAGEL2 gene essentiality classifier. *bioRxiv*, 2020.2005.2030.125526, doi:10.1101/2020.05.30.125526 (2020).

16 Wang, J. et al. Oncoprotein CIP2A is stabilized via interaction with tumor suppressor PP2A/B56. *EMBO Rep* 18, 437-450, doi:10.15252/embr.201642788 (2017).

17 Junttila, M. R. et al. CIP2A inhibits PP2A in human malignancies. *Cell* 130, 51-62, doi:10.1016/j.cell.2007.04.044 (2007).

18 Khanna, A., Pimanda, J. E. & Westermarck, J. Cancerous inhibitor of protein phosphatase 2A, an emerging human oncoprotein and a potential cancer therapy target. *Cancer Res* 73, 6548-6553, doi:10.1158/0008-5472. CAN-13-1994 (2013).

19 Ventela, S. et al. CIP2A promotes proliferation of spermatogonial progenitor cells and spermatogenesis in mice. *PLoS One* 7, e33209, doi:10.1371/journal.pone.0033209 (2012).

20 Olivieri, M. et al. A Genetic Map of the Response to DNA Damage in Human Cells. *Cell* 182, 481-496 e421, doi:10.1016/j.cell.2020.05.040 (2020).
21 Wilson, D. M., 3rd & Thompson, L. H. Molecular mechanisms of sister-chromatid exchange. *Mutat Res* 616, 11-23, doi:10.1016/j.mrfmmm.2006.11.017 (2007).
22 Ito, S., Murphy, C. G., Doubrovina, E., Jasin, M. & Moynahan, M. E. PARP Inhibitors in Clinical Use Induce Genomic Instability in Normal Human Cells. *PLoS One* 11, e0159341, doi:10.1371/journal.pone.0159341 (2016).
23 Kim, J. S., Kim, E. J., Oh, J. S., Park, I. C. & Hwang, S. G. CIP2A modulates cell-cycle progression in human cancer cells by regulating the stability and activity of Plk1. *Cancer Res* 73, 6667-6678, doi:10.1158/0008-5472.CAN-13-0888 (2013).
24 Bunting, S. F. et al. 53BP1 inhibits homologous recombination in Brca1-deficient cells by blocking resection of DNA breaks. *Cell* 141, 243-254, doi:S0092-8674(10)00285-0 [pii] 10.1016/j.cell.2010.03.012 (2010).
25 Leimbacher, P. A. et al. MDC1 Interacts with TOPBP1 to Maintain Chromosomal Stability during Mitosis. *Mol Cell* 74, 571-583 e578, doi:10.1016/j.molcel.2019.02.014 (2019).
26 Bagge, J., Oestergaard, V. H. & Lisby, M. Functions of TopBP1 in preserving genome integrity during mitosis. *Semin Cell Dev Biol*, doi:10.1016/j.semcdb.2020.08.009 (2020).
27 Broderick, R., Nieminuszczy, J., Blackford, A. N., Winczura, A. & Niedzwiedz, W. TOPBP1 recruits TOP2A to ultra-fine anaphase bridges to aid in their resolution. *Nat Commun* 6, 6572, doi:10.1038/ncomms7572 (2015).
28 Bang, S. W. et al. Human TopBP1 localization to the mitotic centrosome mediates mitotic progression. *Exp Cell Res* 317, 994-1004, doi:10.1016/j.yexcr.2011.01.022 (2011).
29 Jeong, A. L. et al. Cancerous inhibitor of protein phosphatase 2A (CIP2A) protein is involved in centrosome separation through the regulation of NIMA (never in mitosis gene A)-related kinase 2 (NEK2) protein activity. *J Biol Chem* 289, 28-40, doi:10.1074/jbc.M113.507954 (2014).
30 Elstrodt, F. et al. BRCA1 mutation analysis of 41 human breast cancer cell lines reveals three new deleterious mutants. *Cancer Res* 66, 41-45, doi:10.1158/0008-5472.CAN-05-2853 (2006).
31 Banaszynski, L. A., Chen, L. C., Maynard-Smith, L. A., Ooi, A. G. & Wandless, T. J. A rapid, reversible, and tunable method to regulate protein function in living cells using synthetic small molecules. *Cell* 126, 995-1004, doi:10.1016/j.cell.2006.07.025 (2006).
32 Hakem, R., de la Pompa, J. L., Elia, A., Potter, J. & Mak, T. W. Partial rescue of Brca1 (5-6) early embryonic lethality by p53 or p21 null mutation. *Nat Genet* 16, 298-302, doi:10.1038/ng0797-298 (1997).
33 Ludwig, T., Chapman, D. L., Papaioannou, V. E. & Efstratiadis, A. Targeted mutations of breast cancer susceptibility gene homologs in mice: lethal phenotypes of Brca1, Brca2, Brca1/Brca2, Brca1/p53, and Brca2/p53 nullizygous embryos. *Genes & development* 11, 1226-1241 (1997).
34 Ozer, O. & Hickson, I. D. Pathways for maintenance of telomeres and common fragile sites during DNA replication stress. *Open Biol* 8, doi:10.1098/rsob.180018 (2018).
35 Noordermeer, S. M. et al. The shieldin complex mediates 53BP1-dependent DNA repair. *Nature* 560, 117-121, doi:10.1038/s41586-018-0340-7 (2018).
36 Hart, T. et al. High-Resolution CRISPR Screens Reveal Fitness Genes and Genotype-Specific Cancer Liabilities. *Cell* 163, 1515-1526, doi:10.1016/j.cell.2015.11.015 (2015).
37 Hart, T. et al. Evaluation and Design of Genome-Wide CRISPR/SpCas9 Knockout Screens. *G3* (*Bethesda*) 7, 2719-2727, doi:10.1534/g3.117.041277 (2017).
38 Ohsumi, T. K. & Borowsky, M. L. MolBioLib: a C++ 11 framework for rapid development and deployment of bioinformatics tasks. *Bioinformatics* 28, 2412-2416, doi:10.1093/bioinformatics/bts458 (2012).
39 Hart, T. & Moffat, J. BAGEL: a computational framework for identifying essential genes from pooled library screens. *BMC Bioinformatics* 17, 164, doi:10.1186/s12859-016-1015-8 (2016).
40 Delignette-Muller, M. L. & Dutang, C. fitdistrplus: An R Package for Fitting Distributions. 2015 64, 34, doi:10.18637/jss.v064.i04 (2015).
41 Tang, J. et al. Acetylation limits 53BP1 association with damaged chromatin to promote homologous recombination. *Nature structural & molecular biology*, doi:10.1038/nsmb.2499 (2013).

What is claimed is:

1. A method for inhibiting, reducing or suppressing the growth or survival of cancer cells with homologous recombination (HR) deficiencies comprising
   i) contacting the cancer cells with an effective amount of a compound or agent that reduces or inhibits phosphopeptide recognition of TOPBP1 BRCT7/8 domains, wherein the compound or agent comprises a peptide of TOPBP1 comprising residues 756 to 1000, 756 to 891, 776-851, or 830 to 851 of SEQ ID NO: 11, or a sequence having 95% identity thereto, and binds CIP2A or a fragment thereof; wherein binding of the peptide to CIP2A reduces the ability of TOPBP1 to interact with CIP2A or destabilizes or inhibits an existing CIP2A-TOPBP1 interaction, either directly or indirectly.

2. The method of claim 1, wherein the cancer cells have a defect or mutation associated with HR deficiency in one or more of BRCA1, BRCA2, dual BRCA1/BRCA2, PALB2, BARD1, BRIP1, RAD51C and RAD51D.

3. The method of claim 2, wherein the cancer cells have a defect or mutation in BRCA1, BRCA2, or both.

4. The method of claim 1, wherein the cancer cells are ovarian cancer cells.

5. A method of treating a cancer associated with or characterized by a homologous recombination deficiency comprising administering to an individual in need thereof an effective amount of a CIP2A-TOPBP1 inhibitor comprising a peptide of TOPBP1 comprising residues 756 to 1000, 756 to 891, 776 to 851, or 830 to 851 of SEQ ID NO: 11, or a sequence having 95% identity thereto, and binds CIP2A or a fragment thereof; wherein binding of the peptide to CIP2A reduces the ability of TOPBP1 to interact with CIP2A or destabilizes or inhibits an existing CIP2A-TOPBP1 interaction, either directly or indirectly.

* * * * *